(12) United States Patent
Vanderhoydonck et al.

(10) Patent No.: US 12,378,202 B2
(45) Date of Patent: Aug. 5, 2025

(54) TETRAHYDROBENZOAZEPINONES AND RELATED ANALOGS FOR INHIBITING YAP/TAZ-TEAD

(71) Applicants: THE KATHOLIEKE UNIVERSITEIT LEUVEN, Vlaams-Brabant Leuven (BE); SpringWorks Therapeutics, Inc., Stamford, CT (US); VIB vzw, Ghent (BE)

(72) Inventors: Bart Vanderhoydonck, Diest (BE); Arnaud Marchand, Bierbeek (BE); Aurélie Candi, Werchter (BE); Matthias Versele, Kessel-Lo (BE)

(73) Assignees: SPRINGWORKS THERAPEUTICS, INC., Stamford, CT (US); KATHOLIEKE UNIVERSITEIT LEUVEN, Vlaams-Brabant Leuven (BE); VIB VZW, Ghent (BE)

( * ) Notice: Subject to any disclaimer, the term of this patent is extended or adjusted under 35 U.S.C. 154(b) by 0 days.

(21) Appl. No.: 18/145,902

(22) Filed: Dec. 23, 2022

(65) Prior Publication Data

US 2023/0278962 A1    Sep. 7, 2023

Related U.S. Application Data

(60) Provisional application No. 63/293,536, filed on Dec. 23, 2021.

(51) Int. Cl.
| | |
|---|---|
| C07D 223/16 | (2006.01) |
| A61K 31/4375 | (2006.01) |
| A61K 31/4704 | (2006.01) |
| A61K 31/55 | (2006.01) |
| A61K 45/06 | (2006.01) |
| A61P 35/00 | (2006.01) |
| C07D 215/227 | (2006.01) |
| C07D 471/04 | (2006.01) |

(52) U.S. Cl.
CPC ........ *C07D 223/16* (2013.01); *A61K 31/4375* (2013.01); *A61K 31/4704* (2013.01); *A61K 31/55* (2013.01); *A61K 45/06* (2013.01); *A61P 35/00* (2018.01); *C07D 215/227* (2013.01); *C07D 471/04* (2013.01)

(58) Field of Classification Search
CPC ............ A61K 31/4375; A61K 31/4704; A61K 31/55; A61P 35/00; C07D 215/227; C07D 215/38; C07D 223/16; C07D 471/04
See application file for complete search history.

(56) References Cited

U.S. PATENT DOCUMENTS

2019/0002479 A1 *   1/2019   Kim ................... C07D 519/00
2020/0317689 A1   10/2020   Chu et al.

FOREIGN PATENT DOCUMENTS

| WO | WO-2014009495 A1 * | 1/2014 | ............. A61K 31/55 |
| WO | 2017064277 A1 | 4/2017 | |
| WO | 2020190774 A1 | 9/2020 | |
| WO | WO-2020243423 A1 * | 12/2020 | ............. A61K 31/09 |
| WO | WO-2022072741 A1 * | 4/2022 | ............. A61P 35/00 |

OTHER PUBLICATIONS

International Search Report issued in PCT/US2022/082325 on Jun. 7, 2023.
Konnerth, et al., "Selective hydrogenation of N-heterocyclic compounds using Ru nanocatalysts in ionic liquids", Green Chemistry, Mar. 28, 2017, vol. 19, p. 2762-2767; p. 2763, right col., Table 1.

* cited by examiner

*Primary Examiner* — Sarah Pihonak
*Assistant Examiner* — Padmaja S Rao
(74) *Attorney, Agent, or Firm* — Blank Rome LLP

(57) ABSTRACT

The present disclosure relates to novel compounds, to said compounds for use as a medicine, more in particular for the prevention or treatment of diseases mediated by activity of YAP/TAZ-TEAD transcription, yet more in particular for the prevention or treatment of cancer or fibrosis. The present disclosure also relates to a method for the prevention or treatment of said diseases comprising the use of the novel compounds.

19 Claims, No Drawings

TETRAHYDROBENZOAZEPINONES AND RELATED ANALOGS FOR INHIBITING YAP/TAZ-TEAD

REFERENCE TO RELATED APPLICATIONS

The present application claims benefit of U.S. Provisional Application No. 63/293,536, filed Dec. 23, 2021, which is hereby incorporated by reference in its entirety.

FIELD

The present disclosure relates to novel compounds. The present disclosure also relates to the compounds for use as a medicine, more in particular for the prevention or treatment of diseases mediated by activity of YAP/TAZ-TEAD transcription, such as for the prevention or treatment of cancer or fibrosis. Methods for the prevention or treatment of the diseases comprising the use of the novel compounds are also disclosed herein.

The present disclosure furthermore relates to pharmaceutical compositions or combination preparations of the novel compounds, as well as to the compositions or preparations for use as a medicine, for example for the prevention or treatment of diseases mediated by activity of YAP/TAZ-TEAD transcription such as the prevention or treatment of cancer or fibrosis. Processes for the preparation of the compounds are also disclosed herein.

BACKGROUND

Hippo signaling is critical to restrict organ size through inactivation of the YAP/TAZ-TEAD transcriptional complex. In several aggressive solid cancers, Hippo signaling is inactivated through loss-of-function mutations or deletions in the genes encoding the upstream regulators (e.g. NF2, MST1/2 or LATS1/2), unleashing constitutive YAP/TAZ-TEAD transcriptional activity leading to unbridled tumor growth and metastasis. Knock-out, knockdown or pharmacologic inactivation of YAP/TAZ-TEAD is sufficient to impair YAP/TAZ-dependent tumorigenesis. The YAP/TAZ-TEAD complex can be pharmacologically inactivated through targeted disruption of the YAP/TAZ-TEAD protein-protein interaction interface, or through an allosteric autopalmitoylation pocket in TEAD.

The main physiologic function of the Hippo pathway is to restrict tissue growth in adult tissue and modulate cell proliferation, differentiation and migration in developing organs. The core of the Hippo pathway consists of a kinase cascade, transcription coactivators and DNA-binding partners. In mammals, the Ste20-like kinases, MST1/2 (homologs of *Drosophila* Hippo) phosphorylate and activate Large Tumor Suppressor 1/2 (LATS1/2). NF2 is a scaffold for the core Hippo kinases, promoting LATS1/2 activation by tethering MST1/2 to LATS1/2 (Lallemand et al., 2003, Genes Dev 17, 1090-1100; Yin et al., 2013, Dev Cell 19, 27-38). The LATS kinases will in turn phosphorylate and inactivate two highly homologous transcriptional co-activators: Yes-associated Protein (YAP) and Transcriptional co-activator with PDZ-binding motif (TAZ) by cytoplasmic sequestration via 14-3-3 and by ubiquitin-mediated degradation induced by β-TRCP E3 ligase. When the Hippo pathway is inactive, YAP and TAZ translocate in the nucleus to bind to the TEAD transcription factor family to induce expression of a specific signature promoting matrix remodeling, cell proliferation, survival and migration. TEAD1-4 can also bind to VGLL4 in the nucleus and act as a transcriptional repressor. VGLL4 is not structurally related to YAP/TAZ, but competes with YAP/TAZ based on a partially overlapping binding site on TEAD (Johnson and Halder, 2014, Nat Rev Drug Discov 13, 63-79).

TEADs are evolutionarily conserved proteins required for cardiogenesis, myogenesis, and for the development of the neural crest, notochord, and trophoectoderm. In mammals, there are four genes encoding four homologous members of the TEAD family named TEAD1-4. Each TEAD gene has a distinct but not mutually exclusive expression pattern. All TEAD family members are controlled by YAP/TAZ.

In fruit flies, loss of function of Hippo or Warts kinases (MST1/2 or LATS1/2 in mammals), or overexpression of Yorkie (the *Drosophila* homolog of YAP and TAZ), results in a dramatic overgrowth of the cuticle, as a result of dysregulated cell proliferation and resistance to apoptosis, leading to increased organ size. In mice, YAP overexpression, loss of MST1/2 or LATS1/2 kinase activities, or loss of NF2 leads to TEAD target gene up-regulation and progenitor cell expansion, resulting in liver and cardiac overgrowth and ultimately cancer formation in the liver, the small intestine and in skin. In contrast, a serine to alanine mutation at position 94 in YAP, that is unable to bind to TEAD, is not oncogenic (Zhao et al., 2008, Genes Dev 22, 1962-1971). Likewise, a dominant-negative TEAD mutant that is unable to bind DNA, overcomes YAP-driven liver tumorigenesis. In addition, NF2 mutant liver carcinoma was greatly suppressed by heterozogous loss of Yap (Zhang et al., 2010, Dev Cell 19, 27-38). Finally, verteporfin, a small molecule that inhibits YAP-TEAD association significantly suppressed the oncogenic activity of YAP in these models (Liu-Chittenden et al., 2012, Genes Dev 26, 1300-1305).

Gene amplification of YAP1 (encoding for YAP) and WWTR1 (encoding for TAZ) as well as constitutive nuclear localization of YAP/TAZ have been reported in many human solid malignancies, including liver, lung, breast, skin, colon and ovarian cancer and YAP/TAZ promote the acquisition of several important cancer cell phenotypes, such as proliferation, resistance to apoptosis, invasion, and immune-suppression (e.g. by attracting myeloid derived suppressor cells (Wang et al., 2016, Cancer Discov 6, 80-95)). In addition, gene fusions with YAP1 have been identified in several cancer types including ependymomas, vascular cancers, cervical carcinomas and porocarcinomas, which results in constitutive activation of YAP-TEAD, and are oncogenic in mice (Szulzewsky et al., 2020, Genes Dev 34: 1-14). In addition, several germline or somatic mutations in components of the Hippo pathway associated with various cancer types have been discovered in targeted and whole-genome sequencing studies. The best studied example is the NF2 locus, mutated with a high frequency in neurofibromatosis. Loss of NF2 and LATS2 are also frequently observed in schwannomas. Another tumor type that is commonly (in about 70% of all cases) associated with constitutive YAP-TEAD activation through genetic inactivation of NF2, LATS1/2, MST1/2 or SAV1, is malignant mesothelioma (Bueno et al., 2016, Nat Genet 48, 407-416.). Recent studies have shown that several mesothelioma cell lines with NF2 loss-of-function mutations exhibit a decrease in YAP phosphorylation and an increase in YAP-TEAD reporter activity. The YAP-TEAD transcription and viability of NF2 mutant mesothelioma cell lines (but not WT mesothelioma) are sensitive to YAP siRNA (an effect which can be rescued by overexpression of siRNA resistant YAP) and to treatment with verteporfin, a YAP antagonist (Zhang et al., 2017, J Cell Mol Med 21: 2663-2676).

Nuclear YAP has also emerged as a critical mediator of WNT dependent colorectal tumorigenesis. YAP-TEAD mediated transcription of genes involved in proliferation and stem cell renewal cooperate with WNT driven beta-catenin, and YAP is required for formation of adenomas following APC (adenomatous polyposis coli) inactivation (Azzolin et al., 2014 Cell 158, 157-170; Gregorieff et al., 2015 Nature 526, 715-718.). Recently, TIAM1, was identified as a suppressor of aggressive, metastatic colorectal cancer (CRC) by antagonizing YAP-TEAD transcription, again highlighting the role of YAP-TEAD in CRC (Diamantopoulou et al., 2017 Cancer Cell 31, 621-634).

In summary, YAP/TAZ activation has been shown to drive tumorigenesis and YAP/TAZ is hyperactivated in many different types of cancer in humans (often through loss-of-function mutations in upstream negative regulators). Genetic deletion or pharmacologic inhibition of YAP/TAZ has been shown to suppress tumor development and progression in different types of cancer. Therefore, it is believed that deregulation of the Hippo tumor suppressor pathway is a major event in the development of a wide range of cancer types and malignancies. Hence, pharmacological targeting of the Hippo cascade through inhibition of YAP, TAZ, TEAD, and/or the YAP/TAZ-TEAD protein-protein interaction would be a valuable approach for the treatment of cancers that harbor functional alterations of this pathway.

YAP/TAZ-TEAD activation has also been shown to play an important role in other diseases than cancer, namely such as in fibrosis and certain congenital disorders. A hallmark of fibrosis is the excessive deposition of extracellular matrix (ECM), including cross-linked collagen fibres, which results in the stiffening of tissues and eventually in dysfunctioning of affected organs. ECM stiffening promotes the nuclear activity of YAP/TAZ in cancer-associated fibroblasts, and fibroblasts of the liver, kidney, lung and skin (Mannaerts et al., 2015, J. Hepatol. 63, 679-688; Piersma et al., 2015, Am. J. Pathol. 185, 3326-3337). Nuclear YAP/TAZ promotes fibrotic cellular phenotypes, such as myofibroblast differentiation and increased matrix remodeling. Several genes that encode key secreted factors implicated in fibrosis are direct YAP/TAZ-TEAD targets. These genes include well-characterized pro-fibrotic factors, such as connective tissue growth factor (CTGF), plasminogen activator inhibitor 1 (PAI-1) and the lysyl oxidase (LOX) family of collagen cross-linking enzymes. Several lines of evidence support YAP/TAZ as contributors to fibrotic disease in vivo. These include reports of elevated YAP/TAZ levels and transcriptional activity in fibroblasts as well as in alveolar and respiratory epithelium of patients with idiopathic pulmonary fibrosis (Gokey et al., 2018 JCI Insight 3: e98738). Increased nuclear YAP has also been observed in patients with primary sclerosing cholangitis and primary biliary cirrhosis, which are chronic fibrotic disorders of liver injury. Expression of YAP or TAZ in the duct cells of the liver drives fibrosis progression that parallels fibrosis in nonalcoholic fatty liver disease (Machado et al., 2015, J. Hepatol 63, 962-970). Collectively, these studies suggest that targeting aberrant YAP/TAZ activity in fibrotic diseases may hold promise for therapy.

Neurofibromatosis type 2 is characterized by nervous system tumors including schwannomas, meningiomas, and ependymomas. Neurofibromatosis type 2 is an inheritable disorder caused by the inactivation of NF2 (Striedinger et al., 2008, Neoplasia 10, 1204-1210). Loss of NF2 leads to constitutive activation of YAP/TAZ-TEAD. The Sturge-Weber syndrome is a congenital eurocutaneous disorder characterized by a port-wine stain affecting the skin in the distribution of the ophthalmic branch of the trigeminal nerve, abnormal capillary venous vessels in the leptomeninges of the brain and choroid, glaucoma, seizures, stroke, and intellectual disability. The Sturge-Weber syndrome and port-wine stains are caused by a somatic activating mutation in GNAQ which leads to activation of YAP/TAZ-TEAD transcription (Shirley et al., 2013, NEJM, 368, 1971-1979). Therefore, several congenital disorders, characterized by constitutive YAP/TAZ-TEAD activation could be treated with inhibitors of YAP/TAZ-TEAD.

A few publications describe inhibitors of the YAP-TEAD transcriptional activation. Inventiva highlighted YAP-TEAD protein-protein interaction inhibitors in WO2020/070181, WO2018/185266, and WO2017/064277. The General Hospital Corporation, Boston described autopalmitoylation inhibitors in WO2017/053706. Vivace Therapeutics, Inc. disclosed non-fused tricyclic (WO2018/204532), benzosulfonyl (WO2019/040380), benzocarbonyl (WO2019/113236), oxadiazole (WO2019/222431), and bicyclic (WO2020/097389) compounds that modulate the interaction between YAP/TAZ and TEAD. The Regents of the University of California and Vivace Therapeutics, Inc. described tricyclic compounds that inhibit the Hippo-YAP signaling pathway in WO2013/188138 and WO2017/058716, respectively. Kyowa Hakko Kirin Co., Ltd. revealed alpha,beta-unsaturated amide compounds that display anti-cancer activity in WO2018/235926 and US2019/0010136. Genentech, Inc. disclosed carboxamide and sulfonamide derivatives useful as inhibitors of the YAP-TEAD protein-protein interaction in WO2019/232216 and WO2020/051099. Dana-Farber Cancer Institute, Inc. highlighted inhibitors of TEAD transcription factors in WO2020/081572. The Trustees of Indiana University described small-molecules that bind within the hydrophobic palmitate-binding pocket of TEADs in WO2020/087063. Wenchao Lu, et al. published vinylsulfonamides as covalent TEAD autopalmitoylation inhibitors (2019, European Journal of Medicinal Chemistry, 184, p. 111767). Korean Research Institute of Chemical Technology disclosed benzo[cd]indol-2(1H)-one derivatives that inhibit YAP-TEAD binding.

However, there is still a great need for novel, alternative or better therapeutics for the prevention or treatment of diseases mediated by the YAP/TAZ-TEAD activation, such as cancer and fibrosis among potentially other indications. Therapeutics with better potency, less side-effects, a higher activity, a lower toxicity or better pharmacokinetic or -dynamic properties or combinations thereof would be very welcome.

The present disclosure provides a class of novel compounds which can be used as inhibitors of the YAP/TAZ-TEAD activation mediated diseases.

SUMMARY OF THE DISCLOSURE

The present disclosure is based on the finding that at least one of the above-mentioned problems can be solved by the below described class of compounds.

The present disclosure provides new compounds which have been shown to possess inhibitory activity on the YAP/TAZ-TEAD transcription. The present disclosure furthermore demonstrates that these compounds efficiently inhibit the activity of YAP/TAZ-TEAD transcription. Therefore, these compounds constitute a useful class of new potent compounds that can be used in the treatment and/or prevention of Hippo mediated disorders in animals, mammals and humans, more specifically for the treatment and/or prevention of (i) cancer, more specifically lung cancer, breast cancer, head and neck cancer, oesophageal cancer, kidney cancer, bladder cancer, colon cancer, ovarian cancer, cervical cancer, endometrial cancer, liver cancer (including but not limited to cholangiocarcinoma), skin cancer, pancreatic cancer, gastric cancer, brain cancer and prostate cancer, mesotheliomas, and/or sarcomas (ii) fibrosis, and (iii) YAP/TAZ-TEAD activation related congenital disorders, among others.

In some aspects, the compounds described herein can be used in the treatment and/or prevention of Hippo mediated disorders in animals, mammals and humans, more specifically for the treatment and/or prevention of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bronchogenic carcinoma, chondrosarcoma, chordoma, choriocarcinoma, chronic leukemia, chronic lymphocytic leukemia, chronic myelocytic (granulocytic) leukemia, chronic myelogenous leukemia, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, papillary adenocarcinomas, papillary carcinoma, pinealoma, polycythemia vera, rectal cancer, renal cell carcinoma, retinoblastoma, rhabdomyosarcoma, sarcoma, sebaceous gland carcinoma, seminoma, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

The present disclosure furthermore relates for the use of such compounds as medicines and to their use for the manufacture of medicaments, more in particular for treating and/or preventing YAP/TAZ-TEAD activation mediated diseases, in particular (i) cancer, more specifically lung cancer, breast cancer, head and neck cancer, oesophageal cancer, kidney cancer, bladder cancer, colon cancer, ovarian cancer, cervical cancer, endometrial cancer, liver cancer (including but not limited to cholangiocarcinoma), skin cancer, pancreatic cancer, gastric cancer, brain cancer and prostate cancer, mesotheliomas, and/or sarcomas and (ii) fibrosis in animals or mammals, more in particular in humans. The disclosure also relates to methods for the preparation of all such compounds and to pharmaceutical compositions comprising them in an effective amount.

In some embodiments, the disclosure relates to the compounds of the invention for use as a medicine, to the use of such compounds as medicines and to their use for the manufacture of medicaments, more in particular for treating and/or preventing YAP/TAZ-TEAD activation mediated diseases more specifically for the treatment and/or prevention of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bronchogenic carcinoma, chondrosarcoma, chordoma, choriocarcinoma, chronic leukemia, chronic lymphocytic leukemia, chronic myelocytic (granulocytic) leukemia, chronic myelogenous leukemia, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, papillary adenocarcinomas, papillary carcinoma, pinealoma, polycythemia vera, rectal cancer, renal cell carcinoma, retinoblastoma, rhabdomyosarcoma, sarcoma, sebaceous gland carcinoma, seminoma, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

The present disclosure also relates to a method of treatment or prevention of TEAD activation mediated disorders in humans by the administration of one or more such compounds, optionally in combination with one or more other medicines, to a patient in need thereof. The present disclosure also relates to methods of preparing the compounds disclosed herein comprising the steps for synthesis of the compounds described herein.

DETAILED DESCRIPTION

Definitions

The term "YAP/TAZ-TEAD activation mediated diseases" refers to diseases in which hippo signaling is inactivated and whereby YAP/TAZ-TEAD activation is contributing, driving, sustaining, enabling or the like such disease. This might be through loss-of-function mutations or deletions in the genes encoding the upstream regulators of YAP/TAZ-TEAD (e.g. NF2, MST1/2, LATS1/2, FAT1 or SAV1), unleashing constitutive YAP-TEAD transcriptional activity leading to unbridled tumor growth and metastasis of some cancers. This might also be through YAP1 or WWTR1 (TAZ) gene amplifications, gene fusions or activating mutations, or YAP/TAZ overexpression or hyperactivity, among others. YAP/TAZ-TEAD activation mediated diseases therefore refers to cancer, but also includes fibrosis and certain congenital disorders. Cancers that are included in YAP/TAZ-TEAD mediated diseases are, without being limited thereto, lung cancer, breast cancer, head and neck cancer, oesophageal cancer, kidney cancer, bladder cancer, colon cancer, ovarian cancer, cervical cancer, endometrial cancer, liver cancer (including but not limited to cholangiocarcinoma), skin cancer, pancreatic cancer, gastric cancer, brain cancer and prostate cancer, mesotheliomas, and/or sarcomas. Also included are (i) squamous cell carcinomas of the lung, cervix, ovaries, head and neck, oesophagus, and/or skin, or (ii) cancers that originate from neuroectoderm-derived tissues, such as ependymomas, meningiomas, schwannomas, peripheral nerve-sheet tumors and/or neuroblastomas, or (iii) vascular cancers, such as epithelioid haemangioendotheliomas. Fibrotic diseases or fibrosis that is included in YAP/TAZ-TEAD mediated diseases are, without being limited thereto, liver fibrosis, lung fibrosis and heart fibrosis. Congenital disorders that are included in YAP/TAZ-TEAD mediated diseases are, without being limited thereto, Sturge-Weber syndrome and Neurofibromatosis type 2.

YAP/TAZ-TEAD mediated diseases also includes cancers that have developed resistance to prior treatments such has EGFR inhibitors, MEK inhibitors, AXL inhibitors, B-RAF inhibitors, RAS inhibitors and others.

The term "treat" or "treating" as used herein is intended to refer to administration of a compound or composition to a subject for the purpose of effecting a therapeutic benefit or prophylactic benefit through inhibition of the YAP/TAZ-TEAD transcription. Treating includes reversing, ameliorating, alleviating, inhibiting the progress of, lessening the severity of, or preventing a disease, disorder, or condition, or one or more symptoms of such disease, disorder or condition mediated through YAP/TAZ-TEAD transcription. By "therapeutic benefit" is meant eradication, amelioration, reversing, alleviating, inhibiting the progress of or lessening the severity of the underlying disorder being treated. Also, a therapeutic benefit is achieved with the eradication or amelioration of one or more of the physiological symptoms associated with the underlying disorder such that an improvement is observed in the patient, notwithstanding that the patient is afflicted with the underlying disorder in some embodiments. For prophylactic benefit, in some embodiments, the compositions are administered to a patient at risk of developing a particular disease, or to a patient reporting one or more of the physiological symptoms of a disease, even though a diagnosis of this disease has not been made.

The term "subject" as used herein, refers to an animal, for example a mammal, such as a human, a patient, who has been the object of treatment, observation or experiment or who is in need of such treatment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation or partial alleviation of the symptoms of the disease or disorder being treated.

The term "composition" as used herein is intended to encompass a product comprising the specified ingredients in the therapeutically effective amounts, as well as any product which results, directly or indirectly, from combinations of the specified ingredients in the specified amounts.

The term "antagonist" or "inhibitor" as used herein in reference to inhibitors of the YAP/TAZ-TEAD activation, refers to a compound capable of producing, depending on the circumstances, a functional antagonism of YAP/TAZ-TEAD activation.

It is to be noticed that the term "comprising", used in the claims, should not be interpreted as being restricted to the means listed thereafter; it does not exclude other elements or steps.

Reference throughout this specification to "one embodiment" or "an embodiment" means that a particular feature, structure or characteristic described in connection with the embodiment is included in at least one embodiment of the present disclosure. Furthermore, the particular features, structures or characteristics may be combined in any suitable manner, as would be apparent to one of ordinary skill in the art from this disclosure, in one or more embodiments. Where an indefinite or definite article is used when referring to a singular noun e.g. "a" or "an", "the", this includes a plural of that noun unless something else is specifically stated.

Similarly it should be appreciated that in the description of exemplary embodiments of the disclosure, various features of the disclosure are sometimes grouped together in a single embodiment, figure, or description thereof for the purpose of streamlining the disclosure and aiding in the understanding of one or more of the various inventive aspects.

In each of the following definitions, the number of carbon atoms represents the maximum number of carbon atoms generally optimally present in the substituent or linker; it is understood that where otherwise indicated in the present application, the number of carbon atoms represents the optimal maximum number of carbon atoms for that particular substituent or linker.

The term "leaving group" or "LG" as used herein means a chemical group which is susceptible to be displaced by a nucleophile or cleaved off or hydrolyzed in basic or acidic conditions. In a particular embodiment, a leaving group is selected from a halogen atom (e.g., Cl, Br, I) or a sulfonate (e.g., mesylate, tosylate, triflate).

The term "protecting group" refers to a moiety of a compound that masks or alters the properties of a functional group or the properties of the compound as a whole. The chemical substructure of a protecting group varies widely. One function of a protecting group is to serve as intermediates in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

The term "alkyl" or "$C_{1-18}$alkyl" as used herein means $C_1$-$C_{18}$ normal, secondary, or tertiary, linear, branched or straight hydrocarbon with no site of unsaturation. Examples are methyl, ethyl, 1-propyl (n-propyl), 2-propyl (iPr), 1-butyl, 2-methyl-1-propyl(i-Bu), 2-butyl (s-Bu), 2-dimethyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-icosyl. In particular embodiments, the term alkyl refers to $C_{1-12}$alkyl ($C_{1-12}$ hydrocarbons), yet more in particular to $C_{1-9}$alkyl ($C_{1-9}$ hydrocarbons), yet more in particular to $C_{1-6}$alkyl ($C_{1-6}$ hydrocarbons) as further defined herein above.

The term "haloalkyl" as a group or part of a group, refers to an alkyl group having the meaning as defined above wherein one, two, or three hydrogen atoms are each replaced with a halogen as defined herein. Non-limiting examples of such haloalkyl groups include chloromethyl, 1-bromoethyl, fluoromethyl, difluoromethyl, trifluoromethyl, 1,1,1-trifluoroethyl and the like.

The term "alkoxy" or "alkyloxy", as a group or part of a group, refers to a group having the formula —$OR^b$ wherein $R^b$ is $C_{1-6}$alkyl as defined herein above. Non-limiting examples of suitable $C_{1-6}$alkoxy include methoxy, ethoxy, propoxy, isopropoxy, butoxy, isobutoxy, sec-butoxy, tert-butoxy, pentyloxy and hexyloxy.

The term "haloalkoxy", as a group or part of a group, refers to a group of formula —O—$R^o$, wherein $R^o$ is haloalkyl as defined herein. Non-limiting examples of suitable haloalkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy, trichloromethoxy, 2-bromoethoxy, pentafluoroethyl, 3,3,3-trichloropropoxy, 4,4,4-trichlorobutoxy.

The term "cycloalkyl" or "$C_{3-18}$ cycloalkyl" as used herein and unless otherwise stated means a saturated hydrocarbon monovalent group having from 3 to 18 carbon atoms consisting of or comprising a $C_{3-10}$ monocyclic or $C_{7-18}$ polycyclic saturated hydrocarbon, such as for instance cyclopropyl, cyclobutyl, cyclopentyl, cyclopropylethylene, methylcyclopropylene, cyclohexyl, cycloheptyl, cyclooctyl, cyclooctylmethylene, norbornyl, fenchyl, trimethyltricycloheptyl, decalinyl, adamantyl and the like. In particular embodiments, the term cycloalkyl refers to $C_{3-12}$cycloalkyl (saturated cyclic $C_{3-12}$ hydrocarbons), yet more in particular to $C_{3-9}$cycloalkyl (saturated cyclic $C_{3-9}$ hydrocarbons), still more in particular to $C_{3-6}$cycloalkyl (saturated cyclic $C_3$-6 hydrocarbons) as further defined herein above. For the avoidance of doubt, fused systems of a cycloalkyl ring with a heterocyclic ring are considered as heterocycle irrespective of the ring that is bound to the core structure. Fused systems of a cycloalkyl ring with an aryl ring are considered as aryl irrespective of the ring that is bound to the core structure. Fused systems of a cycloalkyl ring with a heteroaryl ring are considered as heteroaryl irrespective of the ring that is bound to the core structure.

The term "alkenyl" or "$C_{2-18}$alkenyl" as used herein is $C_2$-$C_{18}$ normal, secondary or tertiary, linear, branched or straight hydrocarbon with at least one site (usually 1 to 3, preferably 1) of unsaturation, namely a carbon-carbon, sp2 double bond. Examples include, but are not limited to: ethylene or vinyl (—CH=$CH_2$), allyl (—$CH_2$CH=$CH_2$), and 5-hexenyl (—$CH_2CH_2CH_2CH_2$CH=$CH_2$). The double bond may be in the cis or trans configuration. In particular embodiments, the term alkenyl refers to $C_{2-12}$alkenyl ($C_{2-12}$ hydrocarbons), yet more in particular to $C_{2-9}$ alkenyl ($C_{2-9}$ hydrocarbons), still more in particular to $C_{2-6}$ alkenyl ($C_{2-6}$ hydrocarbons) as further defined herein above with at least one site (usually 1 to 3, preferably 1) of unsaturation, namely a carbon-carbon, sp2 double bond.

The term "alkenyloxy", as a group or part of a group, refers to a group having the formula —$OR^d$ wherein $R^d$ is alkenyl as defined herein above.

The term "cycloalkenyl" as used herein refers to a non-aromatic hydrocarbon group having from 5 to 18 carbon atoms with at least one site (usually 1 to 3, preferably 1) of unsaturation, namely a carbon-carbon, sp2 double bond and consisting of or comprising a $C_{5-10}$ monocyclic or $C_{7-18}$ polycyclic hydrocarbon. Examples include, but are not limited to: cyclopentenyl (—$C_5H_7$), cyclopentenylpropylene, methylcyclohexenylene and cyclohexenyl (—$C_6H_9$). The double bond may be in the cis or trans configuration. In particular embodiments, the term cycloalkenyl refers to $C_{5-12}$ cycloalkenyl (cyclic $C_{5-12}$ hydrocarbons), yet more in particular to $C_{5-9}$ cycloalkenyl (cyclic $C_{5-9}$ hydrocarbons), still more in particular to $C_{5-6}$ cycloalkenyl (cyclic $C_{5-6}$ hydrocarbons) as further defined herein above with at least one site of unsaturation, namely a carbon-carbon, sp2 double bond. For the avoidance of doubt, fused systems of a cycloalkenyl ring with a heterocyclic ring are considered as heterocycle irrespective of the ring that is bound to the core structure. Fused systems of a cycloalkenyl ring with an aryl ring are considered as aryl irrespective of the ring that is bound to the core structure. Fused systems of a cycloalkenyl ring with a heteroaryl ring are considered as heteroaryl irrespective of the ring that is bound to the core structure.

The term "alkynyl" or "$C_{2-18}$alkynyl" as used herein refers to $C_2$-$C_{18}$ normal, secondary, tertiary, linear, branched or straight hydrocarbon with at least one site (usually 1 to 3, preferably 1) of unsaturation, namely a carbon-carbon, sp triple bond. Examples include, but are not limited to: ethynyl (—C≡CH), 3-ethyl-cyclohept-1-ynylene, and 1-propynyl (propargyl, —$CH_2$C≡CH). In particular embodiments, the term alkynyl refers to $C_{2-12}$ alkynyl ($C_{2-12}$ hydrocarbons), yet more in particular to $C_{2-9}$ alkynyl ($C_{2-9}$ hydrocarbons) yet more in particular to $C_{2-6}$ alkynyl ($C_{2-6}$ hydrocarbons) as further defined herein above with at least one site (usually 1 to 3, preferably 1) of unsaturation, namely a carbon-carbon, sp triple bond.

The term "alkynyloxy", as a group or part of a group, refers to a group having the formula —$OR^e$ wherein $R^e$ is alkynyl as defined herein above.

The term "cycloalkynyl" as used herein refers to a non-aromatic hydrocarbon group having from 5 to 18 carbon atoms with at least one site (usually 1 to 3, preferably 1) of unsaturation, namely a carbon-carbon, sp triple bond and consisting of or comprising a $C_{5-10}$ monocyclic or $C_{7-18}$ polycyclic hydrocarbon. Examples include, but are not limited to: cyclohept-1-yne, 3-ethyl-cyclohept-1-ynylene, 4-cyclohept-1-yn-methylene and ethylene-cyclohept-1-yne. In particular embodiments, the term cycloalkynyl refers to $C_{5-10}$ cycloalkynyl (cyclic $C_{5-10}$ hydrocarbons), yet more in particular to $C_{5-9}$ cycloalkynyl (cyclic $C_{5-9}$ hydrocarbons), still more in particular to $C_{5-6}$ cycloalkynyl (cyclic $C_{5-6}$ hydrocarbons) as further defined herein above with at least one site (usually 1 to 3, preferably 1) of unsaturation, namely a carbon-carbon, sp triple bond. For the avoidance of doubt, fused systems of a cycloalkynyl ring with a heterocyclic ring are considered as heterocycle irrespective of the ring that is bound to the core structure. Fused systems of a cycloalkynyl ring with an aryl ring are considered as aryl irrespective of the ring that is bound to the core structure. Fused systems of a cycloalkynyl ring with a heteroaryl ring are considered as heteroaryl irrespective of the ring that is bound to the core structure.

The term "alkylene" as used herein each refer to a saturated, branched or straight chain hydrocarbon group of 1-18 carbon atoms (more in particular $C_{1-12}$, $C_{1-9}$ or $C_{1-6}$ carbon atoms), and having two monovalent group centers derived by the removal of two hydrogen atoms from the same or two different carbon atoms of a parent alkane. Typical alkylene include, but are not limited to: methylene (—CH$_2$—), 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

The term "alkenylene" as used herein each refer to a branched or straight chain hydrocarbon of 2-18 carbon atoms (more in particular $C_{2-12}$, $C_{2-9}$ or $C_{2-6}$ carbon atoms) with at least one site (usually 1 to 3, preferably 1) of unsaturation, namely a carbon-carbon, sp2 double bond, and having two monovalent centers derived by the removal of two hydrogen atoms from the same or two different carbon atoms of a parent alkene.

The term "alkynylene" as used herein each refer to a branched or straight chain hydrocarbon of 2-18 carbon atoms (more in particular $C_{2-12}$, $C_{2-9}$ or $C_{2-6}$ carbon atoms) with at least one site (usually 1 to 3, preferably 1) of unsaturation, namely a carbon-carbon, sp triple bond, and having two monovalent centers derived by the removal of two hydrogen atoms from the same or two different carbon atoms of a parent alkyne.

The term "heteroalkyl" as used herein refers to an alkyl wherein one or more carbon atoms are replaced by one or more atoms selected from the group comprising oxygen, nitrogen or sulphur atom. The term heteroalkyl thus comprises —O—R$^b$, —NR$^o$—R$^b$, —R$^a$—O—R$^b$, and —S—R$^b$, wherein R$^a$ is alkylene, R$^b$ is alkyl, and R$^o$ is hydrogen or alky as defined herein. In particular embodiments, the term refers to $C_{1-12}$ heteroalkyl, $C_{1-9}$ heteroalkyl or $C_{1-6}$ heteroalkyl. In some embodiments heteroalkyl is selected from the group comprising alkyloxy, alkyl-oxy-alkyl, (mono or di)alkylamino, (mono or di-)alkyl-amino-alkyl, alkylthio, and alkyl-thio-alkyl.

The term "heteroalkenyl" as used herein refers to an acyclic alkenyl wherein one or more carbon atoms are replaced by one or more atoms selected from oxygen, nitrogen or sulphur atom. The term heteroalkenyl thus comprises —O—R$^d$, —NH—(R$^d$), —N(R$^d$)$_2$, —N(R$^b$)(R$^d$), and —S—R$^d$ wherein R$^b$ is alkyl and R$^d$ is alkenyl as defined herein. In particular embodiments, the term refers to $C_{2-12}$ heteroalkenyl, $C_{2-9}$ heteroalkenyl or $C_{2-6}$ heteroalkenyl. In some embodiments heteroalkenyl is selected from the group comprising alkenyloxy, alkenyl-oxy-alkenyl, (mono or di-)alkenylamino, (mono or di-)alkenyl-amino-alkenyl, alkenylthio, and alkenyl-thio-alkenyl, The term "heteroalkynyl" as used herein refers to an acyclic alkynyl wherein one or more carbon atoms are replaced by an oxygen, nitrogen or sulphur atom. The term heteroalkynyl thus comprises but is not limited to —O—R$^d$, —N(R$^d$)$_2$, NHR$^d$, —N(R$^b$)(R$^e$), —N(R$^d$)(R$^e$), and —S—R$^d$ wherein R$^b$ is alkyl, R$^e$ is alkynyl and R$^d$ is alkenyl as defined herein. In particular embodiments, the term refers to $C_{2-12}$ heteroalkynyl, $C_{2-9}$ heteroalkynyl or $C_{2-6}$ heteroalkynyl. In some embodiments the term heteroalkynyl is selected from the group comprising alkynyloxy, alkynyl-oxy-alkynyl, (mono or di-)alkynylamino, (mono or di-)alkynyl-amino-alkynyl, alkynylthio, alkynyl-thio-alkynyl, The term "heteroalkylene" as used herein refers to an alkylene wherein one or more carbon atoms are replaced by one or more oxygen, nitrogen or sulphur atoms.

The term "heteroalkenylene" as used herein refers to an alkenylene wherein one or more carbon atoms are replaced by one or more oxygen, nitrogen or sulphur atoms.

The term "heteroalkynylene" as used herein refers to an alkynylene wherein one or more carbon atoms are replaced by one or more oxygen, nitrogen or sulphur atom.

The term "aryl" as used herein means an aromatic hydrocarbon of 6-20 carbon atoms derived by the removal of hydrogen from a carbon atom of a parent aromatic ring system. Typical aryl groups include, but are not limited to 1 ring, or 2 or 3 rings fused together, derived from benzene, naphthalene, anthracene, biphenyl, and the like. In particular embodiments, the term aryl refers to a 6-14 carbon atoms membered aromatic cycle, yet more in particular refers to a 6-10 carbon atoms membered aromatic cycle. Fused systems of an aryl ring with a cycloalkyl ring, or a cycloalkenyl ring, or a cycloalkynyl ring, are considered as aryl irrespective of the ring that is bound to the core structure. Fused systems of an aryl ring with a heterocycle are considered as heterocycle irrespective of the ring that is bound to the core structure. Thus, indoline, dihydrobenzofurane, dihydrobenzothiophene and the like are considered as heterocycle according to the disclosure. Fused systems of an aryl ring with a heteroaryl ring are considered as heteroaryl irrespective of the ring that is bound to the core structure.

The term "aryloxy", as a group or part of a group, refers to a group having the formula —OR$^g$ wherein R$^g$ is aryl as defined herein above.

The term "arylalkyl" or "arylalkyl-" as used herein refers to an alkyl in which one of the hydrogen atoms bonded to a carbon atom, typically a terminal or sp3 carbon atom, is replaced with an aryl. Typical arylalkyl groups include, but are not limited to, benzyl, 2-phenylethan-1-yl, 2-phenylethen-1-yl, naphthylmethyl, 2-naphthylethyl, and the like. The arylalkyl group comprises 6 to 20 carbon atoms, e.g. the alkyl moiety of the arylalkyl group is 1 to 6 carbon atoms and the aryl moiety is 6 to 14 carbon atoms.

The term "arylalkyloxy", as a group or part of a group, refers to a group having the formula —O—R$^a$—R$^g$ wherein R$^g$ is aryl, and R$^a$ is alkylene as defined herein above.

The term "arylalkenyl" or "arylalkenyl-" as used herein refers to an alkenyl in which one of the hydrogen atoms bonded to a carbon atom, is replaced with an aryl. The arylalkenyl group comprises 6 to 20 carbon atoms, e.g. the alkenyl moiety of the arylalkenyl group is 1 to 6 carbon atoms and the aryl moiety is 6 to 14 carbon atoms.

The term "arylalkynyl" or "arylalkynyl-" as used herein refers to an alkynyl in which one of the hydrogen atoms bonded to a carbon atom, is replaced with an aryl. The arylalkynyl group comprises 6 to 20 carbon atoms, e.g. the alkynyl moiety of the arylalkynyl group is 1 to 6 carbon atoms and the aryl moiety is 6 to 14 carbon atoms.

The term "arylheteroalkyl" or "arylheteroalkyl-" as used herein refers to a heteroalkyl in which one of the hydrogen atoms bonded to a carbon atom, typically a terminal or sp3 carbon atom, is replaced with aryl. The arylheteroalkyl group comprises 6 to 20 carbon atoms, e.g. the heteroalkyl moiety of the arylheteroalkyl group is 1 to 6 carbon atoms and the aryl moiety is 6 to 14 carbon atoms. In some embodiments arylheteroalkyl is selected from the group comprising aryl-O-alkyl, arylalkyl-O-alkyl, aryl-NH-alkyl, aryl-N(alkyl)$_2$, arylalkyl-NH-alkyl, arylalkyl-N-(alkyl)$_2$, aryl-S-alkyl, and arylalkyl-S-alkyl.

The term "arylheteroalkenyl" or "arylheteroalkenyl-" as used herein refers to a heteroalkenyl in which one of the hydrogen atoms bonded to a carbon atom, is replaced with an aryl. The arylheteroalkenyl group comprises 6 to 20 carbon atoms, e.g. the heteroalkenyl moiety of the arylheteroalkenyl group is 1 to 6 carbon atoms and the aryl moiety is 6 to 14 carbon atoms. In some embodiments arylheteroalkenyl is selected from the group comprising aryl-O-alkenyl, arylalkenyl-O-alkenyl, aryl-NH-alkenyl, aryl-N(alkenyl)$_2$, arylalkenyl-NH-alkenyl, arylalkenyl-N-(alkenyl)$_2$, aryl-S-alkenyl, and arylalkenyl-S-alkenyl.

The term "arylheteroalkynyl" or "arylheteroalkynyl-" as used herein refers to a heteroalkynyl in which one of the hydrogen atoms bonded to a carbon atom, is replaced with an aryl. The arylheteroalkynyl group comprises 6 to 20 carbon atoms, e.g. the heteroalkynyl moiety of the arylheteroalkynyl group is 1 to 6 carbon atoms and the aryl moiety is 6 to 14 carbon atoms. In some embodiments arylheteroalkynyl is selected from the group comprising aryl-O-alkynyl, arylalkynyl-O-alkynyl, aryl-NH-alkynyl, aryl-N(alkynyl)$_2$, arylalkynyl-NH-alkynyl, arylalkynyl-N-(alkynyl)$_2$, aryl-S-alkynyl, and arylalkynyl-S-alkynyl.

The term "heterocycle" or "heterocyclyl" as used herein refer to non-aromatic, fully saturated or partially unsaturated ring system of 3 to 18 atoms including at least one N, O, S, or P (for example, 3 to 7 member monocyclic, 7 to 11 member bicyclic, or comprising a total of 3 to 10 ring atoms). Each ring of the heterocycle or heterocyclyl may have 1, 2, 3 or 4 heteroatoms selected from N, O and/or S, where the N and S heteroatoms may optionally be oxidized and the N heteroatoms may optionally be quaternized; and wherein at least one carbon atom of heterocyclyl can be oxidized to form at least one C=O. The heterocycle may be attached at any heteroatom or carbon atom of the ring or ring system, where valence allows. The rings of multi-ring heterocyclyls or heterocycles may be fused, bridged and/or joined through one or more spiro atoms. Fused systems of a heterocycle or heterocyclyl with an aryl ring are considered as heterocycle or heterocyclyl irrespective of the ring that is bound to the core structure. Fused systems of a heterocycle or heterocyclyl with a heteroaryl ring are considered as heteroaryl irrespective of the ring that is bound to the core structure.

Non limiting exemplary heterocycles or heterocyclic groups include piperidinyl, piperazinyl, homopiperazinyl, morpholinyl, tetrahydropyranyl, tetrahydrofuranyl, pyrrolidinyl, aziridinyl, oxiranyl, thiiranyl, azetidinyl, oxetanyl, thietanyl, 2-imidazolinyl, pyrazolidinyl imidazolidinyl, isoxazolinyl, oxazolidinyl, isoxazolidinyl, thiazolidinyl, isothiazolidinyl, succinimidyl, 3H-indolyl, indolinyl, isoindolinyl, chromanyl (also known as 3,4-dihydrobenzo[b]pyranyl), 2H-pyrrolyl, 1-pyrrolinyl, 2-pyrrolinyl, 3-pyrrolinyl, 4H-quinolizinyl, 2-oxopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, indolinyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl. The term "aziridinyl" as used herein includes aziridin-1-yl and aziridin-2-yl. The term "oxyranyl" as used herein includes oxyranyl-2-yl. The term "thiiranyl" as used herein includes thiiran-2-yl. The term "azetidinyl" as used herein includes azetidin-1-yl, azetidin-2-yl and azetidin-3-yl. The term "oxetanyl" as used herein includes oxetan-2-yl and oxetan-3-yl. The term "thietanyl" as used herein includes thietan-2-yl and thietan-3-yl. The term "pyrrolidinyl" as used herein includes pyrrolidin-1-yl, pyrrolidin-2-yl and pyrrolidin-3-yl. The term "tetrahydrofuranyl" as used herein includes tetrahydrofuran-2-yl and tetrahydrofuran-3-yl. The term "tetrahydrothiophenyl" as used herein includes tetrahydrothiophen-2-yl and tetrahydrothiophen-3-yl. The term "succinimidyl" as used herein includes succinimid-1-yl and succinimid-3-yl. The term "dihydropyrrolyl" as used herein includes 2,3-dihydropyrrol-1-yl, 2,3-dihydro-1H-pyrrol-2-yl, 2,3-dihydro-1H-pyrrol-3-yl, 2,5-dihydropyrrol-1-yl, 2,5-dihydro-1H-pyrrol-3-yl and 2,5-dihydropyrrol-5-yl. The term "2H-pyrrolyl" as used herein includes 2H-pyrrol-2-yl, 2H-pyrrol-3-yl, 2H-pyrrol-4-yl and 2H-pyrrol-5-yl. The term "3H-pyrrolyl" as used herein includes 3H-pyrrol-2-yl, 3H-pyrrol-3-yl, 3H-pyrrol-4-yl and 3H-pyrrol-5-yl. The term "dihydrofuranyl" as used herein includes 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,5-dihydrofuran-4-yl and 2,5-dihydrofuran-5-yl. The term "dihydrothiophenyl" as used herein includes 2,3-dihydrothiophen-2-yl, 2,3-dihydrothiophen-3-yl, 2,3-dihydrothiophen-4-yl, 2,3-dihydrothiophen-5-yl, 2,5-dihydrothiophen-2-yl, 2,5-dihydrothiophen-3-yl, 2,5-dihydrothiophen-4-yl and 2,5-dihydrothiophen-5-yl. The term "imidazolidinyl" as used herein includes imidazolidin-1-yl, imidazolidin-2-yl and imidazolidin-4-yl. The term "pyrazolidinyl" as used herein includes pyrazolidin-1-yl, pyrazolidin-3-yl and pyrazolidin-4-yl. The term "imidazolinyl" as used herein includes imidazolin-1-yl, imidazolin-2-yl, imidazolin-4-yl and imidazolin-5-yl. The term "pyrazolinyl" as used herein includes 1-pyrazolin-3-yl, 1-pyrazolin-4-yl, 2-pyrazolin-1-yl, 2-pyrazolin-3-yl, 2-pyrazolin-4-yl, 2-pyrazolin-5-yl, 3-pyrazolin-1-yl, 3-pyrazolin-2-yl, 3-pyrazolin-3-yl, 3-pyrazolin-4-yl and 3-pyrazolin-5-yl. The term "dioxolanyl" also known as "1,3-dioxolanyl" as used herein includes dioxolan-2-yl, dioxolan-4-yl and dioxolan-5-yl. The term "dioxolyl" also known as "1,3-dioxolyl" as used herein includes dioxol-2-yl, dioxol-4-yl and dioxol-5-yl. The term "oxazolidinyl" as used herein includes oxazolidin-2-yl, oxazolidin-3-yl, oxazolidin-4-yl and oxazolidin-5-yl. The term "isoxazolidinyl" as used herein includes isoxazolidin-2-yl, isoxazolidin-3-yl, isoxazolidin-4-yl and isoxazolidin-5-yl. The term "oxazolinyl" as used herein includes 2-oxazolinyl-2-yl, 2-oxazolinyl-4-yl, 2-oxazolinyl-5-yl, 3-oxazolinyl-2-yl, 3-oxazolinyl-4-yl, 3-oxazolinyl-5-yl, 4-oxazolinyl-2-yl, 4-oxazolinyl-3-yl, 4-oxazolinyl-4-yl and 4-oxazolinyl-5-yl. The term "isoxazolinyl" as used herein includes 2-isoxazolinyl-3-yl, 2-isoxazolinyl-4-yl, 2-isoxazolinyl-5-yl, 3-isoxazolinyl-3-yl, 3-isoxazolinyl-4-yl, 3-isoxazolinyl-5-yl, 4-isoxazolinyl-2-yl, 4-isoxazolinyl-3-yl, 4-isoxazolinyl-4-yl and 4-isoxazolinyl-5-yl. The term "thiazolidinyl" as used herein includes thiazolidin-2-yl, thiazolidin-3-yl, thiazolidin-4-yl and thiazolidin-5-yl. The term "isothiazolidinyl" as used herein includes isothiazolidin-2-yl, isothiazolidin-3-yl, isothiazolidin-4-yl and isothiazolidin-5-yl. The term "thiazolinyl" as used herein includes 2-thiazolinyl-2-yl, 2-thiazolinyl-4-yl, 2-thiazolinyl-5-yl, 3-thiazolinyl-2-yl, 3-thiazolinyl-4-yl, 3-thiazolinyl-5-yl, 4-thiazolinyl-2-yl, 4-thiazolinyl-3-yl, 4-thiazolinyl-4-yl and 4-thiazolinyl-5-yl. The term "isothiazolinyl" as used herein includes 2-isothiazolinyl-3-yl, 2-isothiazolinyl-4-yl, 2-isothiazolinyl-5-yl, 3-isothiazolinyl-3-yl, 3-isothiazolinyl-4-yl, 3-isothiazolinyl-5-yl, 4-isothiazolinyl-2-yl, 4-isothiazolinyl-3-yl, 4-isothiazolinyl-4-yl and 4-isothiazolinyl-5-yl. The term "piperidyl" also known as "piperidinyl" as used herein includes piperid-1-yl, piperid-2-yl, piperid-3-yl and piperid-4-yl. The term "dihydropyridinyl" as used herein includes 1,2-dihydropyridin-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,4-dihydropyridin-1-yl, 1,4-dihydropyridin-2-yl, 1,4-dihydropyridin-3-yl, 1,4-dihydropyridin-4-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 3,4-dihydropyridin-2-yl, 3,4-dihydropyridin-3-yl, 3,4-dihydropyridin-4-yl, 3,4-dihydropyridin-5-yl and 3,4-dihydropyridin-6-yl. The term "tetrahydropyridinyl" as used herein includes 1,2,3,4-tetrahydropyridin-1-yl, 1,2,3,4-tetrahydropyridin-2-yl, 1,2,3,4-tetrahydropyridin-3-yl, 1,2,3,4-tetrahydropyridin-4-yl, 1,2,3,4-tetrahydropyridin-5-yl, 1,2,3,4-tetrahydropyridin-6-yl, 1,2,3,6-tetrahydropyridin-1-yl, 1,2,3,6-tetrahydropyridin-2-yl, 1,2,3,6-tetrahydropyridin-3-yl, 1,2,3,6-tetrahydropyridin-4-yl, 1,2,3,6-tetrahydropyridin-5-yl, 1,2,3,6-tetrahydropyridin-6-yl, 2,3,4,5-tetrahydropyridin-2-yl, 2,3,4,5-tetrahydropyridin-3-yl, 2,3,4,5-tetrahydropyridin-3-yl, 2,3,4,5-tetrahydropyridin-4-yl, 2,3,4,5-tetrahydropyridin-5-yl and 2,3,4,5-tetrahydropyridin-6-yl. The term "tetrahydropyranyl" also known as "oxanyl" or "tetrahydro-2H-pyranyl", as used herein includes tetrahydropyran-2-yl, tetrahydropyran-3-yl and tetrahydropyran-4-yl. The term "2H-pyranyl" as used herein includes 2H-pyran-2-yl, 2H-pyran-3-yl, 2H-pyran-4-yl, 2H-pyran-5-yl and 2H-pyran-6-yl. The term "4H-pyranyl" as used herein includes 4H-pyran-2-yl, 4H-pyran-3-yl and 4H-pyran-4-yl. The term "3,4-dihydro-2H-pyranyl" as used herein includes 3,4-dihydro-2H-pyran-2-yl, 3,4-dihydro-2H-pyran-3-yl, 3,4-dihydro-2H-pyran-4-yl, 3,4-dihydro-2H-pyran-5-yl and 3,4-dihydro-2H-pyran-6-yl. The term "3,6-dihydro-2H-pyranyl" as used herein includes 3,6-dihydro-2H-pyran-2-yl, 3,6-dihydro-2H-pyran-3-yl, 3,6-dihydro-2H-pyran-4-yl, 3,6-dihydro-2H-pyran-5-yl and 3,6-dihydro-2H-pyran-6-yl. The term "tetrahydrothiophenyl", as used herein includes tetrahydrothiophen-2-yl, tetrahydrothiophenyl-3-yl and tetrahydrothiophenyl-4-yl. The term "2H-thiopyranyl" as used herein includes 2H-thiopyran-2-yl, 2H-thiopyran-3-yl, 2H-thiopyran-4-yl, 2H-thiopyran-5-yl and 2H-thiopyran-6-yl. The term "4H-thiopyranyl" as used herein includes 4H-thiopyran-2-yl, 4H-thiopyran-3-yl and 4H-thiopyran-4-yl. The term "3,4-dihydro-2H-thiopyranyl" as used herein includes 3,4-dihydro-2H-thiopyran-2-yl, 3,4-dihydro-2H-thiopyran-3-yl, 3,4-dihydro-2H-thiopyran-4-yl, 3,4-dihydro-2H-thiopyran-5-yl and 3,4-dihydro-2H-thiopyran-6-yl. The term "3,6-dihydro-2H-thiopyranyl" as used herein includes 3,6-dihydro-2H-thiopyran-2-yl, 3,6-dihydro-2H-thiopyran-3-yl, 3,6-dihydro-2H-thiopyran-4-yl, 3,6-dihydro-2H-thiopyran-5-yl and 3,6-dihydro-2H-thiopyran-6-yl. The term "piperazinyl" also known as "piperazidinyl" as used herein includes piperazin-1-yl and piperazin-2-yl. The term "morpholinyl" as used herein includes morpholin-2-yl, morpholin-3-yl and morpholin-4-yl. The term "thiomorpholinyl" as used herein includes thiomorpholin-2-yl, thiomorpholin-3-yl and thiomorpholin-4-yl. The term "dioxanyl" as used herein includes 1,2-dioxan-3-yl, 1,2-dioxan-4-yl, 1,3-dioxan-2-yl, 1,3-dioxan-4-yl, 1,3-dioxan-5-yl and 1,4-dioxan-2-yl. The term "dithianyl" as used herein includes 1,2-dithian-3-yl, 1,2-dithian-4-yl, 1,3-dithian-2-yl, 1,3-dithian-4-yl, 1,3-dithian-5-yl and 1,4-dithian-2-yl. The term "oxathianyl" as used herein includes oxathian-2-yl and oxathian-3-yl. The term "trioxanyl" as used herein includes 1,2,3-trioxan-4-yl, 1,2,3-trioxan-5-yl, 1,2,4-trioxan-3-yl, 1,2,4-trioxan-5-yl, 1,2,4-trioxan-6-yl and 1,3,4-trioxan-2-yl. The term "azepanyl" as used herein includes azepan-1-yl, azepan-2-yl, azepan-3-yl and azepan-4-yl. The term "homopiperazinyl" as used herein includes homopiperazin-1-yl, homopiperazin-2-yl, homopiperazin-3-yl and homopiperazin-4-yl. The term "indolinyl" as used herein includes indolin-1-yl, indolin-2-yl, indolin-3-yl, indolin-4-yl, indolin-5-yl, indolin-6-yl, and indolin-7-yl. The term "quinolizinyl" as used herein includes quinolizidin-1-yl, quinolizidin-2-yl, quinolizidin-3-yl and quinolizidin-4-yl. The term "isoindolinyl" as used herein includes isoindolin-1-yl, isoindolin-2-yl, isoindolin-3-yl, isoindolin-4-yl, isoindolin-5-yl, isoindolin-6-yl, and isoindolin-7-yl. The term "3H-indolyl" as used herein includes 3H-indol-2-yl, 3H-indol-3-yl, 3H-indol-4-yl, 3H-indol-5-yl, 3H-indol-6-yl, and 3H-indol-7-yl. The term "quinolizinyl" as used herein includes quinolizidin-1-yl, quinolizidin-2-yl, quinolizidin-3-yl and quinolizidin-4-yl. The term "quinolizinyl" as used herein includes quinolizidin-1-yl, quinolizidin-2-yl, quinolizidin-3-yl and quinolizidin-4-yl. The term "tetrahydroquinolinyl" as used herein includes tetrahydroquinolin-1-yl, tetrahydroquinolin-2-yl, tetrahydroquinolin-3-yl, tetrahydroquinolin-4-yl, tetrahydroquinolin-5-yl, tetrahydroquinolin-6-yl, tetrahydroquinolin-7-yl and tetrahydroquinolin-8-yl. The term "tetrahydroisoquinolinyl" as used herein includes tetrahydroisoquinolin-1-yl, tetrahydroisoquinolin-2-yl, tetrahydroisoquinolin-3-yl, tetrahydroisoquinolin-4-yl, tetrahydroisoquinolin-5-yl, tetrahydroisoquinolin-6-yl, tetrahydroisoquinolin-7-yl and tetrahydroisoquinolin-8-yl. The term "chromanyl" as used herein includes chroman-2-yl, chroman-3-yl, chroman-4-yl, chroman-5-yl, chroman-6-yl, chroman-7-yl and chroman-8-yl. The term "1H-pyrrolizine" as used herein includes 1H-pyrrolizin-1-yl, 1H-pyrrolizin-2-yl, 1H-pyrrolizin-3-yl, 1H-pyrrolizin-5-yl, 1H-pyrrolizin-6-yl and 1H-pyrrolizin-7-yl. The term "3H-pyrrolizine" as used herein includes 3H-pyrrolizin-1-yl, 3H-pyrrolizin-2-yl, 3H-pyrrolizin-3-yl, 3H-pyrrolizin-5-yl, 3H-pyrrolizin-6-yl and 3H-pyrrolizin-7-yl.

The term "heteroaryl" refers to an aromatic ring system of 5 to 18 atoms including at least one N, O, S, or P, containing 1 or 2 rings which can be fused together or linked covalently, each ring typically containing 5 to 6 atoms; at least one of said rings is aromatic, where the N and S heteroatoms may optionally be oxidized and the N heteroatoms may optionally be quaternized, and wherein at least one carbon atom of said heteroaryl can be oxidized to form at least one C=O. Fused systems of a heteroaryl ring with a cycloalkyl ring, or a cycloalkenyl ring, or a cycloalkynyl ring, are considered as heteroaryl irrespective of the ring that is bound to the core structure. Fused systems of a heteroaryl ring with a heterocycle are considered as heteroaryl irrespective of the ring that is bound to the core structure. Fused systems of a hetero aryl ring with an aryl ring are considered as heteroaryl irrespective of the ring that is bound to the core structure. Non-limiting examples of such heteroaryl, include: triazol-2-yl, pyridinyl, 1H-pyrazol-5-yl, pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, benzo[d]oxazol-2(3H)-one, 2,3-dihydro-benzofuranyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl; in some embodiments, said heteroaryl group is selected from the group comprising pyridyl, pyrazinyl, pyrimidinyl, pyrazolyl, pyrrolyl, isoxazolyl, thiophenyl, imidazolyl, indolyl, benzimidazolyl, s-triazinyl, oxazolyl, isothiazolyl, furyl, thienyl, triazolyl and thiazolyl; in some embodiments, said heteroaryl group is selected from the group comprising pyridyl, pyrazinyl, pyrimidinyl, indolyl and benzimidazolyl.

The term "pyrrolyl" (also called azolyl) as used herein includes pyrrol-1-yl, pyrrol-2-yl and pyrrol-3-yl. The term "furanyl" (also called "furyl") as used herein includes furan-2-yl and furan-3-yl (also called furan-2-yl and furan-3-yl). The term "thiophenyl" (also called "thienyl") as used herein includes thiophen-2-yl and thiophen-3-yl (also called thien-2-yl and thien-3-yl). The term "pyrazolyl" (also called 1H-pyrazolyl and 1,2-diazolyl) as used herein includes pyrazol-1-yl, pyrazol-3-yl or 1H-pyrazol-5-yl, pyrazol-4-yl and pyrazol-5-yl. The term "imidazolyl" as used herein includes imidazol-1-yl, imidazol-2-yl, imidazol-4-yl and imidazol-5-yl. The term "oxazolyl" (also called 1,3-oxazolyl) as used herein includes oxazol-2-yl, oxazol-4-yl and oxazol-5-yl. The term "isoxazolyl" (also called 1,2-oxazolyl), as used herein includes isoxazol-3-yl, isoxazol-4-yl, and isoxazol-5-yl. The term "thiazolyl" (also called 1,3-thiazolyl), as used herein includes thiazol-2-yl, thiazol-4-yl and thiazol-5-yl (also called 2-thiazolyl, 4-thiazolyl and 5-thiazolyl). The term "isothiazolyl" (also called 1,2-thiazolyl) as used herein includes isothiazol-3-yl, isothiazol-4-yl, and isothiazol-5-yl. The term "triazolyl" as used herein includes triazol-2-yl, 1H-triazolyl and 4H-1,2,4-triazolyl, "1H-triazolyl" includes 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl and 1H-1,2,4-triazol-5-yl. "4H-1,2,4-triazolyl" includes 4H-1,2,4-triazol-4-yl, and 4H-1,2,4-triazol-3-yl. The term "oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl. The term "thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl. The term "tetrazolyl" as used herein includes 1H-tetrazol-1-yl, 1H-tetrazol-5-yl, 2H-tetrazol-2-yl, and 2H-tetrazol-5-yl. The term "oxatriazolyl" as used herein includes 1,2,3,4-oxatriazol-5-yl and 1,2,3,5-oxatriazol-4-yl. The term "thiatriazolyl" as used herein includes 1,2,3,4-thiatriazol-5-yl and 1,2,3,5-thiatriazol-4-yl. The term "pyridinyl" (also called "pyridyl") as used herein includes pyridin-2-yl, pyridin-3-yl and pyridin-4-yl (also called 2-pyridyl, 3-pyridyl and 4-pyridyl). The term "pyrimidyl" as used herein includes pyrimid-2-yl, pyrimid-4-yl, pyrimid-5-yl and pyrimid-6-yl. The term "pyrazinyl" as used herein includes pyrazin-2-yl and pyrazin-3-yl. The term "pyridazinyl as used herein includes pyridazin-3-yl and pyridazin-4-yl. The term "oxazinyl" (also called "1,4-oxazinyl") as used herein includes 1,4-oxazin-4-yl and 1,4-oxazin-5-yl. The term "dioxinyl" (also called "1,4-dioxinyl") as used herein includes 1,4-dioxin-2-yl and 1,4-dioxin-3-yl. The term "thiazinyl" (also called "1,4-thiazinyl") as used herein includes 1,4-thiazin-2-yl, 1,4-thiazin-3-yl, 1,4-thiazin-4-yl, 1,4-thiazin-5-yl and 1,4-thiazin-6-yl. The term "triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl. The term "imidazo[2,1-b][1,3]thiazolyl" as used herein includes imidazo[2,1-b][1,3]thiazoi-2-yl, imidazo[2,1-b][1,3]thiazol-3-yl, imidazo[2,1-b][1,3]thiazol-5-yl and imidazo[2,1-b][1,3]thiazol-6-yl. The term "thieno[3,2-b]furanyl" as used herein includes thieno[3,2-b]furan-2-yl, thieno[3,2-b]furan-3-yl, thieno[3,2-b]furan-4-yl, and thieno[3,2-b]furan-5-yl. The term "thieno[3,2-b]thiophenyl" as used herein includes thieno[3,2-b]thien-2-yl, thieno[3,2-b]thien-3-yl, thieno[3,2-b]thien-5-yl and thieno[3,2-b]thien-6-yl. The term "thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl. The term "thieno[2,3-d]imidazolyl" as used herein includes thieno[2,3-d]imidazol-2-yl, thieno[2,3-d]imidazol-4-yl and thieno[2,3-d]imidazol-5-yl. The term "tetrazolo[1,5-a]pyridinyl" as used herein includes tetrazolo[1,5-a]pyridine-5-yl, tetrazolo[1,5-a]pyridine-6-yl, tetrazolo[1,5-a]pyridine-7-yl, and tetrazolo[1,5-a]pyridine-8-yl. The term "indolyl" as used herein includes indol-1-yl, indol-2-yl, indol-3-yl,-indol-4-yl, indol-5-yl, indol-6-yl and indol-7-yl. The term "indolizinyl" as used herein includes indolizin-1-yl, indolizin-2-yl, indolizin-3-yl, indolizin-5-yl, indolizin-6-yl, indolizin-7-yl, and indolizin-8-yl. The term "isoindolyl" as used herein includes isoindol-1-yl, isoindol-2-yl, isoindol-3-yl, isoindol-4-yl, isoindol-5-yl, isoindol-6-yl and isoindol-7-yl. The term "benzofuranyl" (also called benzo[b]furanyl) as used herein includes benzofuran-2-yl, benzofuran-3-yl, benzofuran-4-yl, benzofuran-5-yl, benzofuran-6-yl and benzofuran-7-yl. The term "isobenzofuranyl" (also called benzo[c]furanyl) as used herein includes isobenzofuran-1-yl, isobenzofuran-3-yl, isobenzofuran-4-yl, isobenzofuran-5-yl, isobenzofuran-6-yl and isobenzofuran-7-yl. The term "benzothiophenyl" (also called benzo[b]thienyl) as used herein includes 2-benzo[b]thiophenyl, 3-benzo[b]thiophenyl, 4-benzo[b]thiophenyl, 5-benzo[b]thiophenyl, 6-benzo[b]thiophenyl and -7-benzo[b]thiophenyl (also called benzothien-2-yl, benzothien-3-yl, benzothien-4-yl, benzothien-5-yl, benzothien-6-yl and benzothien-7-yl). The term "isobenzothiophenyl" (also called benzo[c]thienyl) as used herein includes isobenzothien-1-yl, isobenzothien-3-yl, isobenzothien-4-yl, isobenzothien-5-yl, isobenzothien-6-yl and isobenzothien-7-yl. The term "indazolyl" (also called 1H-indazolyl or 2-azaindolyl) as used herein includes 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, and 2H-indazol-7-yl. The term "benzimidazolyl" as used herein includes benzimidazol-1-yl, benzimidazol-2-yl, benzimidazol-4-yl, benzimidazol-5-yl, benzimidazol-6-yl and benzimidazol-7-yl. The term "1,3-benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl. The term "1,2-benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl. The term "2,1-benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1- benzisoxazol-7-yl. The term "1,3-benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl. The term "1,2-benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl. The term "2,1-benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl. The term "benzotriazolyl" as used herein includes benzotriazol-1-yl, benzotriazol-4-yl, benzotriazol-5-yl, benzotriazol-6-yl and benzotriazol-7-yl. The term "1,2,3-benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl. The term "2,1,3-benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl. The term "1,2,3-benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl. The term "2,1,3-benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl. The term "thienopyridinyl" as used herein includes thieno[2,3-b]pyridinyl, thieno[2,3-c]pyridinyl, thieno[3,2-c]pyridinyl and thieno[3,2-b]pyridinyl. The term "purinyl" as used herein includes purin-2-yl, purin-6-yl, purin-7-yl and purin-8-yl. The term "imidazo[1,2-a]pyridinyl", as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl. The term "1,3-benzodioxolyl", as used herein includes 1,3-benzodioxol-4-yl, 1,3-benzodioxol-5-yl, 1,3-benzodioxol-6-yl, and 1,3-benzodioxol-7-yl. The term "quinolinyl" as used herein includes quinolin-2-yl, quinolin-3-yl, quinolin-4-yl, quinolin-5-yl, quinolin-6-yl, quinolin-7-yl and quinolin-8-yl. The term "isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl. The term "cinnolinyl" as used herein includes cinnolin-3-yl, cinnolin-4-yl, cinnolin-5-yl, cinnolin-6-yl, cinnolin-7-yl and cinnolin-8-yl. The term "quinazolinyl" as used herein includes quinazolin-2-yl, quinazolin-4-yl, quinazolin-5-yl, quinazolin-6-yl, quinazolin-7-yl and quinazolin-8-yl. The term "quinoxalinyl" as used herein includes quinoxalin-2-yl, quinoxalin-5-yl, and quinoxalin-6-yl.

Heteroaryl and heterocycle or heterocyclyl as used herein includes by way of example and not limitation these groups described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; Katritzky, Alan R., Rees, C. W. and Scriven, E. "Comprehensive Heterocyclic Chemistry" (Pergamon Press, 1996); and J. Am. Chem. Soc. (1960) 82:5566.

The term "heterocyclyloxy" or "heterocyleoxy", as a group or part of a group, refers to a group having the formula —O—$R^i$ wherein $R^i$ is heterocyclyl as defined herein above.

The term "heterocyclylalkyloxy" or "heterocyleoxy", as a group or part of a group, refers to a group having the formula —O—$R^a$—$R^i$ wherein $R^i$ is heterocyclyl, and $R^a$ is alkyl as defined herein above.

The term "heteroaryloxy", as a group or part of a group, refers to a group having the formula —O—$R^k$ wherein $R^k$ is heteroaryl as defined herein above.

The term "heteroarylalkyloxy", as a group or part of a group, refers to a group having the formula —O—$R^a$—$R^i$ wherein $R^i$ is heteroaryl, and $R^a$ is alkyl as defined herein above.

The term "heterocyclyl-alkyl" or "heterocycle-alkyl" as a group or part of a group, refers to an alkyl in which one of the hydrogen atoms bonded to a carbon atom, typically a terminal or sp3 carbon atom, is replaced with a heterocyclyl. A non-limiting example of a heterocyclyl-alkyl or heterocycle-alkyl group is 2-piperidinyl-methylene. The heterocyclyl-alkyl or heterocycle-alkyl group can comprise 6 to 20 atoms, e.g. the alkyl moiety is 1 to 6 carbon atoms and the heterocyclyl moiety is 3 to 14 atoms.

The term "heterocyclyl-alkenyl" or "heterocycle-alkenyl" as a group or part of a group refers to an alkenyl in which one of the hydrogen atoms bonded to a carbon atom, is replaced with an heterocyclyl. The heterocyclyl-alkenyl or heterocycle-alkenyl group can comprise 6 to 20 atoms, e.g. the alkenyl moiety is 2 to 6 carbon atoms and the heterocyclyl moiety is 3 to 14 atoms.

The term "heterocyclyl-alkynyl" or "heterocycle-alkynyl" as a group or part of a group refers to an alkynyl in which one of the hydrogen atoms bonded to a carbon atom, is replaced with a heterocyclyl. The heterocyclyl-alkynyl or heterocycle-alkynyl group can comprise 6 to 20 atoms, e.g. the alkynyl moiety can comprise 2 to 6 carbon atoms and the heterocyclyl moiety can comprise 3 to 14 atoms.

The term "heterocyclyl-heteroalkyl" or "heterocycle-heteroalkyl" as a group or part of a group refers to a heteroalkyl in which one of the hydrogen atoms bonded to a carbon atom, typically a terminal or sp3 carbon atom, is replaced with a heterocyclyl. The heterocyclyl-heteroalkyl or heterocycle-heteroalkyl group can comprise 6 to 20 atoms, e.g. the heteroalkyl moiety can comprise 1 to 6 carbon atoms and the heterocyclyl moiety can comprise 3 to 14 atoms. In some embodiments heterocyclyl-heteroalkyl or heterocycle-heteroalkyl is selected from the group comprising heterocyclyl-O-alkyl, heterocyclylalkyl-O-alkyl, heterocyclyl-NH-alkyl, heterocyclyl-N(alkyl)$_2$, heterocyclylalkyl-NH-alkyl, heterocyclylalkyl-N-(alkyl)$_2$, heterocyclyl-S-alkyl, and heterocyclylalkyl-S-alkyl.

The term "heterocyclyl-heteroalkenyl" or "heterocycle-heteroalkenyl" as a group or part of a group refers to a heteroalkenyl in which one of the hydrogen atoms bonded to a carbon atom, is replaced with a heterocyclyl. The heterocyclyl-heteroalkenyl or heterocycle-heteroalkenyl group can comprise 6 to 20 atoms, e.g. the heteroalkenyl moiety can comprise 2 to 6 carbon atoms and the heterocyclyl moiety can comprise 3 to 14 atoms. In some embodiments heterocyclyl-heteroalkenyl or heterocycle-heteroalkenyl is selected from the group comprising heterocyclyl-O-alkenyl, heterocyclylalkyl-O-alkenyl, heterocyclyl-NH-alkenyl, heterocyclyl-N(alkenyl)$_2$, heterocyclylalkyl-NH-alkenyl, heterocyclylalkyl-N-(alkenyl)$_2$, heterocyclyl-S-alkenyl, and heterocyclylalkenyl-S-alkenyl.

The term "heterocyclyl-heteroalkynyl" or "heterocycle-heteroalkynyl" as a group or part of a group refers to a heteroalkynyl in which one of the hydrogen atoms bonded to a carbon atom, is replaced with a heterocyclyl. The heterocyclyl-heteroalkynyl or heterocycle-heteroalkynyl group can comprise 6 to 20 atoms, e.g. the heteroalkynyl moiety can comprise 2 to 6 carbon atoms and the heterocyclyl moiety can comprise 3 to 14 atoms. In some embodiments heterocyclyl-heteroalkynyl is selected from the group comprising heterocyclyl-O-alkynyl, heterocyclylalkynyl-O-alkynyl, heterocyclyl-NH-alkynyl, heterocyclyl-N(alkynyl)$_2$, heterocyclylalkynyl-NH-alkynyl, heterocyclylalkynyl-N-(alkynyl)$_2$, heterocyclyl-S-alkynyl, and heterocyclylalkynyl-S-alkynyl.

The term "heteroaryl-alkyl" as a group or part of a group refers to an alkyl in which one of the hydrogen atoms bonded to a carbon atom, typically a terminal or sp3 carbon atom, is replaced with a heteroaryl. An example of a heteroaryl-alkyl group is 2-pyridyl-methylene. The heteroaryl-alkyl group can comprise 6 to 20 atoms, e.g. the alkyl moiety of the heteroaryl-alkyl group can comprise 1 to 6 carbon atoms and the heteroaryl moiety can comprise 5 to 14 atoms.

The term "heteroaryl-alkenyl" as a group or part of a group refers to an alkenyl in which one of the hydrogen atoms bonded to a carbon atom, is replaced with an heteroaryl. The heteroaryl-alkenyl group can comprise 6 to 20 atoms, e.g. the alkenyl moiety of the heteroaryl-alkenyl group can comprise 2 to 6 carbon atoms and the heteroaryl moiety can comprise 5 to 14 atoms.

The term "heteroaryl-alkynyl" as a group or part of a group as used herein refers to an alkynyl in which one of the hydrogen atoms bonded to a carbon atom, is replaced with a heteroaryl. The heteroaryl-alkynyl group comprises 6 to 20 atoms, e.g. the alkynyl moiety of the heteroaryl-alkynyl group is 2 to 6 carbon atoms and the heteroaryl moiety is 5 to 14 atoms.

The term "heteroaryl-heteroalkyl" as a group or part of a group as used herein refers to a heteroalkyl in which one of the hydrogen atoms bonded to a carbon atom, typically a terminal or sp3 carbon atom, is replaced with a heteroaryl. The heteroaryl-heteroalkyl group comprises 7 to 20 atoms, e.g. the heteroalkyl moiety of the heteroaryl-heteroalkyl group is 2 to 6 carbon atoms and the heteroaryl moiety is 5 to 14 atoms. In some embodiments heteroaryl-heteroalkyl is selected from the group comprising heteroaryl-O-alkyl, heteroarylalkyl-O-alkyl, heteroaryl-NH-alkyl, heteroaryl-N(alkyl)$_2$, heteroarylalkyl-NH-alkyl, heteroarylalkyl-N-(alkyl)$_2$, heteroaryl-S-alkyl, and heteroarylalkyl-S-alkyl.

The term "heteroaryl-heteroalkenyl" as a group or part of a group as used herein refers to a heteroalkenyl in which one of the hydrogen atoms bonded to a carbon atom, is replaced with an heteroaryl. The heteroaryl-heteroalkenyl group comprises 8 to 20 atoms, e.g. the heteroalkenyl moiety of the heteroaryl-heteroalkenyl group is 3 to 6 carbon atoms and the heteroaryl moiety is 5 to 14 atoms. In some embodiments heteroaryl-heteroalkenyl is selected from the group comprising heteroaryl-O-alkenyl, heteroarylalkenyl-O-alkenyl, heteroaryl-NH-alkenyl, heteroaryl-N(alkenyl)$_2$, heteroarylalkenyl-NH-alkenyl, heteroarylalkenyl-N-(alkenyl)$_2$, heteroaryl-S-alkenyl, and heteroarylalkenyl-S-alkenyl.

The term "heteroaryl-heteroalkynyl" as a group or part of a group as used herein refers to a heteroalkynyl in which one of the hydrogen atoms bonded to a carbon atom, is replaced with a heteroaryl. The heteroaryl-heteroalkynyl group comprises 8 to 20 atoms, e.g. the heteroalkynyl moiety of the heteroaryl-heteroalkynyl group is 2 to 6 carbon atoms and the heteroaryl moiety is 5 to 14 atoms. In some embodiments heteroaryl-heteroalkynyl is selected from the group comprising heteroaryl-O-alkynyl, heteroarylalkynyl-O-alkynyl, heteroaryl-NH-alkynyl, heteroaryl-N(alkynyl)$_2$, heteroarylalkynyl-NH-alkynyl, heteroarylalkynyl-N-(alkynyl)$_2$, heteroaryl-S-alkynyl, and heteroarylalkynyl-S-alkynyl.

By way of example, carbon bonded heteroaryl or heterocyclic rings (or heterocycles) can be bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heteroaryls and heterocyclyls include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl. By way of example, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or 8-carboline. Still more typically, nitrogen bonded heteroaryls or heterocyclyls include 1-aziridyl, 1-azetedyl, 1-pyrrolyl, 1-imidazolyl, 1-pyrazolyl, and 1-piperidinyl.

As used herein and unless otherwise stated, the terms "alkoxy", "cyclo-alkoxy", "aryloxy", "arylalkyloxy", "heteroaryloxy" "heterocyclyloxy", "alkylthio", "cycloalkylthio", "arylthio", "arylalkylthio", "heteroarylthio" and "heterocyclylthio" refer to substituents wherein an alkyl group, respectively a cycloalkyl, aryl, arylalkyl heteroaryl, or heterocyclyl (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like. The same definitions will apply for alkenyl and alkynyl instead of alkyl.

The term "alkylthio", as a group or part of a group, refers to a group having the formula —S—$R^b$ wherein $R^b$ is alkyl as defined herein above. Non-limiting examples of alkylthio groups include methylthio (—SCH$_3$), ethylthio (—SCH$_2$CH$_3$), n-propylthio, isopropylthio, n-butylthio, isobutylthio, sec-butylthio, tert-butylthio and the like.

The term "alkenylthio", as a group or part of a group, refers to a group having the formula —S—$R^d$ wherein $R^d$ is alkenyl as defined herein above.

The term "alkynylthio", as a group or part of a group, refers to a group having the formula —S—$R^e$ wherein $R^e$ is alkynyl as defined herein above.

The term "arylthio", as a group or part of a group, refers to a group having the formula —S—$R^g$ wherein $R^g$ is aryl as defined herein above.

The term "arylalkylthio", as a group or part of a group, refers to a group having the formula —S—$R^a$—$R^g$ wherein $R^a$ is alkylene and $R^g$ is aryl as defined herein above.

The term "heterocyclylthio", as a group or part of a group, refers to a group having the formula —S—$R^i$ wherein $R^i$ is heterocyclyl as defined herein above.

The term "heteroarylthio", as a group or part of a group, refers to a group having the formula —S—$R^k$ wherein $R^k$ is heteroaryl as defined herein above.

The term "heterocyclylalkylthio", as a group or part of a group, refers to a group having the formula —S—$R^a$—$R^i$ wherein $R^a$ is alkylene and $R^i$ is heterocyclyl as defined herein above.

The term "heteroarylalkylthio", as a group or part of a group, refers to a group having the formula —S—$R^a$—$R^k$ wherein $R^a$ is alkylene and $R^k$ is heteroaryl as defined herein above.

The term "mono- or di-alkylamino", as a group or part of a group, refers to a group of formula —N($R^o$)($R^b$) wherein $R^o$ is hydrogen, or alkyl, $R^b$ is alkyl. Thus, alkylamino include mono-alkyl amino group (e.g. mono-alkylamino group such as methylamino and ethylamino), and di-alkylamino group (e.g. di-alkylamino group such as dimethylamino and diethylamino). Non-limiting examples of suitable mono- or di-alkylamino groups include n-propylamino, isopropylamino, n-butylamino, i-butylamino, sec-butylamino, t-butylamino, pentylamino, n-hexylamino, di-n-propylamino, di-1-propylamino, ethylmethylamino, methyl-n-propylamino, methyl-1-propylamino, n-butylmethylamino, i-butylmethylamino, t-butylmethylamino, ethyl-n-propylamino, ethyl-i-propylamino, n-butylethylamino, i-butylethylamino, t-butylethylamino, di-n-butylamino, di-1-butylamino, methylpentylamino, methylhexylamino, ethylpentylamino, ethylhexylamino, propylpentylamino, propylhexylamino, and the like.

The term "mono- or di-arylamino", as a group or part of a group, refers to a group of formula —N($R^q$)($R^r$) wherein $R^q$ and $R^r$ are each independently selected from hydrogen, aryl, or alkyl, wherein at least one of $R^q$ or $R^r$ is aryl.

The term "mono- or di-heteroarylamino", as a group or part of a group, refers to a group of formula —N($R^u$)($R^v$) wherein $R^u$ and $R^v$ are each independently selected from hydrogen, heteroaryl, or alkyl, wherein at least one of $R^u$ or R is heteroaryl as defined herein.

The term "mono- or di-heterocyclylamino", as a group or part of a group, refers to a group of formula —N($R^w$)($R^x$) wherein $R^w$ and $R^x$ are each independently selected from hydrogen, heterocyclyl, or alkyl, wherein at least one of $R^w$ or $R^x$ is heterocyclyl as defined herein.

As used herein and unless otherwise stated, the term halogen means any atom selected from the group consisting of fluorine (F), chlorine (Cl), bromine (Br) and iodine (I).

The terminology regarding a chemical group "which optionally includes one or more heteroatoms, said heteroatoms being selected from the atoms consisting of O, S, and N" as used herein, refers to a group where one or more carbon atoms are replaced by an oxygen, nitrogen or sulphur atom and thus includes, depending on the group to which is referred, heteroalkyl, heteroalkenyl, heteroalkynyl, heteroalkyl, heteroalkenyl, heteroalkynyl, cycloheteroalkyl, cycloheteroalkenyl, cycloheteroalkynyl, heteroaryl, arylheteroalkyl, heteroarylalkyl, heteroarylheteroalkyl, arylheteroalkenyl, heteroarylalkenyl, heteroarylheteroalkenyl, heteroarylheteroalkenyl, arylheteroalkynyl, heteroarylalkynyl, heteroarylheteroalkynyl, among others. This term therefore comprises, depending on the group to which is referred, as an example alkoxy, alkenyloxy, alkynyloxy, alkyl-O-alkylene, alkenyl-O-alkylene, arylalkoxy, benzyloxy, heteroaryl-heteroalkyl, heterocyclyl-heteroalkyl, heteroaryl-alkoxy, heterocyclyl-alkoxy, among others. As an example, the terminology "alkyl which optionally includes one or more heteroatoms, said heteroatoms being selected from the atoms consisting of O, S, and N" therefore refers to heteroalkyl, meaning an alkyl which comprises one or more heteroatoms in the hydrocarbon chain, whereas the heteroatoms may be positioned at the beginning of the hydrocarbon chain, in the hydrocarbon chain or at the end of the hydrocarbon chain. Examples of heteroalkyl include methoxy, methylthio, ethoxy, propoxy, $CH_3$—O—$CH_2$—, $CH_3$—S—$CH_2$—, $CH_3$—$CH_2$—O—$CH_2$—, $CH_3$—NH—, ($CH_3$)$_2$—N—, ($CH_3$)$_2$—$CH_2$—NH—$CH_2$—$CH_2$—, among many other examples. As an example, the terminology "arylalkylene which optionally includes one or more heteroatoms in the alkylene chain, said heteroatoms being selected from the atoms consisting of O, S, and N" therefore refers to arylheteroalkylene, meaning an arylalkylene which comprises one or more heteroatoms in the hydrocarbon chain, whereas the heteroatoms may be positioned at the beginning of the hydrocarbon chain, in the hydrocarbon chain or at the end of the hydrocarbon chain. "Arylheteroalkylene" thus includes aryloxy, arylalkoxy, aryl-alkyl-NH— and the like and examples are phenyloxy, benzyloxy, aryl-$CH_2$—S—$CH_2$—, aryl-$CH_2$—O—$CH_2$—, aryl-NH—$CH_2$— among many other examples. The same counts for "heteroalkenylene", "heteroalkynylene", and other terms used herein when referred to "which optionally includes one or more heteroatoms, said heteroatoms being selected from the atoms consisting of O, S, and N".

The terminology regarding a chemical group "wherein optionally two or more hydrogen atoms on a carbon atom or heteroatom of said group can be taken together to form a =O or =S" as used herein, refers to a group where two or more hydrogen atoms on a carbon atom or heteroatom of said group are taken together to form =O or =S. As an example, the terminology refers to "an alkyl wherein optionally two or more hydrogen atoms on a carbon atom or heteroatom of said alkyl can be taken together to form a =O or =S", includes among other examples $CH_3$—C(O)—$CH_2$—, $CH_3$—C(O)—, $CH_3$—C(S)—$CH_2$—, $CH_3$—S(O)$_2$—$CH_2$— and ($CH_3$)$_2$—$CH_2$—C(O)—$CH_2$—$CH_2$—.

The combination for a group "which optionally includes one or more heteroatoms, said heteroatoms being selected from the atoms consisting of O, S, and N" and "wherein optionally two or more hydrogen atoms on a carbon atom or heteroatom of said group can be taken together to form a =O or =S" can combine the two aspects described herein above and includes, if the group referred to is alkyl, among other examples $CH_3$—C(O)O—, $CH_3$—C(O)O—$CH_2$—, $CH_3$—NH—C(O)—, $CH_3$—C(O)—NH— $CH_3$—NH—C(O)—$CH_2$—, $CH_3$—NH—C(S)—$CH_2$—, $CH_3$—NH—C(S)—NH—$CH_2$—, $CH_3$—NH—S(O)$_2$— and $CH_3$—NH—S(O)$_2$—NH—$CH_2$—.

The term "single bond" as used herein for a linking group i.e. in a way that a certain linking group is selected from a single bond, etc. in the formulas herein, refers to a molecule wherein the linking group is not present and therefore refers to compounds with a direct linkage via a single bond between the two moieties being linked by the linking group.

As used herein with respect to a substituting group, and unless otherwise stated, the terms "substituted" such as in "substituted alkyl", "substituted alkenyl", substituted alkynyl", "substituted aryl", "substituted heteroaryl", "substituted heterocyclyl", "substituted arylalkyl", "substituted heteroaryl-alkyl", "substituted heterocyclyl-alkyl" and the like refer to the chemical structures defined herein, and wherein the said alkyl, alkenyl, alkynyl, group and/or the said aryl, heteroaryl, or heterocyclyl may be optionally substituted with one or more substituents (preferable 1, 2, 3, 4, 5 or 6), meaning that one or more hydrogen atoms are each independently replaced with at least one substituent. Typical substituents include, but are not limited to and in a particular embodiment said substituents are being independently selected from the group consisting of halogen, amino, hydroxyl, sulfhydryl, alkyl, alkoxy, alkenyl, alkenyloxy, alkynyl, alkynyloxy, cycloalkyl, cycloalkenyl, cycloalkynyl, heteroalkyl, heteroalkenyl, heteroalkynyl, aryl, heteroaryl, heterocyclyl, arylalkyl, arylalkenyl, arylalkynyl, cycloalkyl-alkyl, cycloalkylalkenyl, cycloalkylalkynyl, heteroaryl-alkyl, heterocyclyl-alkyl, heteroaryl-alkenyl, heterocyclyl-alkenyl and heteroaryl-alkynyl, heterocyclyl-alkynyl, —X, —Z, —O, —OZ, =O, —SZ, —S⁻, =S, —NZ₂, —N⁺Z₃, =NZ, =N—OZ, —CX₃ (e.g. trifluoromethyl), —CN, —OCN, —SCN, —N=C=O, —N=C=S, —NO, —NO₂, =N₂, —N₃, —NZC(O)Z, —NZC(S)Z, —NZC(O)O⁻, —NZC(O)OZ, —NZC(S)OZ, —NZC(O)NZZ, NZC(NZ)Z, NZC(NZ)NZZ, —C(O)NZZ, —C(NZ)Z, —S(O)₂O—, —S(O)₂OZ, —S(O)₂Z, —OS(O)₂OZ, —OS(O)₂Z, —OS(O)₂O—, —S(O)₂NZZ, —S(O)(NZ)Z, —S(O)Z, —OP(O)(OZ)₂, —P(O)(OZ)₂, —P(O)(O⁻)₂, —P(O)(OZ)(O⁻), —P(O)(OH)₂, —C(O)Z, —C(O)X, —C(S)Z, —C(O)OZ, —C(O)O—, —C(S)OZ, —C(O)SZ, —C(S)SZ, —C(O)NZZ, —C(S)NZZ, —C(NZ)NZZ, —OC(O)Z, —OC(S)Z, —OC(O)O—, —OC(O)OZ, —OC(S)OZ, wherein each X is independently a halogen selected from F, Cl, Br, or I; and each Z is independently —H, alkyl, alkenyl, alkynyl, heteroalkyl, heteroalkenyl, heteroalkynyl, aryl, heteroaryl, heterocyclyl, cycloalkyl, protecting group or prodrug moiety, while two Z bonded to a nitrogen atom can be taken together with the nitrogen atom to which they are bonded to form a heteroaryl, or heterocyclyl. Alkyl(ene), alkenyl(ene), and alkynyl(ene) groups may also be similarly substituted.

Any substituent designation that is found in more than one site in a compound of this disclosure shall be independently selected.

Substituents optionally are designated with or without bonds. Regardless of bond indications, if a substituent is polyvalent (based on its position in the structure referred to), then any and all possible orientations of the substituent are intended.

As used herein and unless otherwise stated, the term "solvate" includes any combination which may be formed by a derivative of this disclosure with a suitable inorganic solvent (e.g. hydrates) or organic solvent, such as but not limited to alcohols, ketones, esters, ethers, nitriles and the like.

The term "heteroatom(s)" as used herein means an atom selected from nitrogen, which can be quaternized; oxygen; and sulfur, including sulfoxide and sulfone.

The term "hydroxy" as used herein means —OH.

The term "carbonyl" as used herein means carbon atom bonded to oxygen with a double bond, i.e., C=O.

The term "amino" as used herein means the —NH₂ group.

The present disclosure provides novel compounds which have been shown to possess YAP/TAZ-TEAD transcription inhibitory activity. The present disclosure furthermore demonstrates that these compounds efficiently inhibit TEAD activation and thereby inhibit YAP/TAZ-TEAD transcription activation. Therefore, these compounds constitute a useful class of new potent compounds that can be used in the treatment and/or prevention of YAP/TAZ-TEAD activation mediated diseases in subjects, more specifically for the treatment and/or prevention of cancer and fibrosis, among other diseases.

The present disclosure furthermore relates to the compounds for use as medicines and to their use for the manufacture of medicaments for treating and/or preventing cancer or fibrosis. The present disclosure relates to the compounds for use as medicines for treating and/or preventing YAP/TAZ-TEAD activation mediated diseases such as cancer or fibrosis in animals, mammals, more in particular in humans. The disclosure also relates to methods for the preparation of all such compounds and to pharmaceutical compositions comprising them in an effective amount. The present disclosure also relates to a method of treatment or prevention of cancer or fibrosis in humans by the administration of one or more such compounds, optionally in combination with one or more other medicines, to a patient in need thereof. The present disclosure also relates to the compounds for veterinary use and to their use as medicines for the prevention or treatment of diseases in a non-human mammal, such as cancer and fibrosis in non-human mammals.

In one embodiment, compounds of the disclosure are compounds of Formula I:

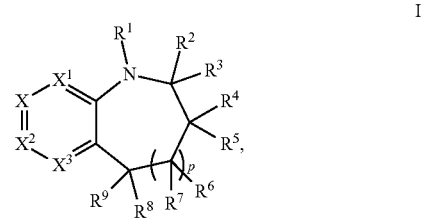

or a stereoisomer, tautomer, pharmaceutically acceptable salt, or solvate thereof, wherein:
p is 0, 1, or 2;
R¹ is selected from the group consisting of:
  (i) hydrogen,
  (ii) unsubstituted or substituted $C_1$-$C_6$ alkyl, wherein one or more substituents are independently selected from the group consisting of:
    (a) unsubstituted or substituted $C_6$-$C_{10}$ aryl, wherein one or more substituents are independently selected from the group consisting of:
      (1) halogen,
      (2) cyano,
      (3) $C_1$-$C_6$ alkyl,
      (4) $C_3$-$C_6$ cycloalkyl,
      (5) $C_1$-$C_6$ haloalkyl,
      (6) —OZ¹,
      (7) $C_2$-$C_6$ alkenyl, and
      (8) $C_2$-$C_6$ alkynyl,
    (b) unsubstituted or substituted $C_3$-$C_6$ cycloalkyl, wherein one or more substituents are independently selected from the group consisting of:
      (1) halogen,
      (2) cyano,
      (3) $C_1$-$C_6$ alkyl,
      (4) $C_3$-$C_6$ cycloalkyl,
      (5) $C_1$-$C_6$ haloalkyl, and
      (6) —OZ¹,
    (c) $C_2$-$C_6$ alkynyl,
  (iii) unsubstituted or substituted $C_6$-$C_{10}$ aryl, wherein one or more substituents are independently selected from the group consisting of:
    (a) halogen,
    (b) cyano,
    (c) $C_1$-$C_6$ alkyl,
    (d) $C_3$-$C_6$ cycloalkyl,
    (e) $C_1$-$C_6$ haloalkyl,
    (f) —OZ¹, and
    (g) unsubstituted or substituted $C_6$-$C_{10}$ aryl, wherein one or more substituents are independently selected from the group consisting of halogen, $C_1$-$C_6$ alkyl, and $C_1$-$C_6$ haloalkyl, and —OZ¹,
  (iv) unsubstituted or substituted 5- to 9-membered heteroaryl, wherein one or more substituents are independently selected from the group consisting of:

(a) halogen,
(b) cyano,
(c) $C_1$-$C_6$ alkyl,
(d) $C_3$-$C_6$ cycloalkyl,
(e) $C_1$-$C_6$ haloalkyl,
(f) —$OZ^1$, and
(g) unsubstituted or substituted $C_6$-$C_{10}$ aryl, wherein one or more substituents are independently selected from the group consisting of halogen, $C_1$-$C_6$ alkyl, and $C_1$-$C_6$ haloalkyl, and —$OZ^1$,
(v) unsubstituted or substituted $C_3$-$C_6$ cycloalkyl, wherein one or more substituents are independently selected from the group consisting of:
(a) halogen,
(b) cyano,
(c) $C_1$-$C_6$ alkyl,
(d) $C_3$-$C_6$ cycloalkyl,
(e) $C_1$-$C_6$ haloalkyl, and
(f) —$OZ^1$,
(vi) unsubstituted or substituted $C_3$-$C_6$ heterocycle, wherein one or more substituents are independently selected from the group consisting of:
(a) halogen,
(b) cyano,
(c) $C_1$-$C_6$ alkyl,
(d) $C_3$-$C_6$ cycloalkyl,
(e) $C_1$-$C_6$ haloalkyl, and
(f) —$OZ^1$,
(vii) —$S(=O)_2Z^2$, and
(viii) —$C(=O)Z^2$;
$R^2$ and $R^3$ are independently selected from the group consisting of hydrogen and $C_1$-$C_6$ alkyl; or
$R^2$ and $R^3$ taken together with the carbon atom to which they are attached form a —$C(=O)$— group;
$R^4$ is selected from the group consisting of hydrogen and —$NR^{10a}R^{10b}$;
$R^5$ is selected from the group consisting of hydrogen and $C_1$-$C_6$ alkyl;
each $R^6$ and $R^7$ is independently selected from the group consisting of hydrogen and $C_1$-$C_6$ alkyl;
$R^8$ and $R^9$ are independently selected from the group consisting of hydrogen and $C_1$-$C_6$ alkyl; or
$R^8$ and $R^9$ taken together with the carbon atom to which they are attached form a —$C(=O)$— group;
$R^{10a}$ is selected from the group consisting of:
(i) —$C(=O)Z^2$
(ii) —$C(=O)OZ^2$,
(iii) —$C(=O)NZ^3Z^4$,
(iv) —$S(=O)_2Z^2$,
(v) —$S(=O)_2NZ^3Z^4$,
(vi) —$S(=O)(=NZ)Z^2$,
(vii) —$S(=NZ^5)(=NZ^6)Z^2$,
(viii) —$S(=O)(=NZ)NZ^3Z^4$, and
(ix) unsubstituted or substituted $C_1$-$C_6$ alkyl, wherein one or more substituents are independently selected from the group consisting of:
(a) cyano,
(b) hydroxy,
(c) —$OZ^1$,
(d) —$C(=O)OH$
(e) —$C(=O)Z^2$
(f) —$C(=O)OZ^2$,
(g) —$C(=O)NZ^3Z^4$,
(h) —$S(=O)_2Z^2$,
(i) —$S(=O)_2NZ^3Z^4$,
(j) —$S(=O)(=NZ^5)Z^2$,
(k) —$S(=NZ^5)(=NZ^6)Z^2$,
(k) —$S(=O)(=NZ^5)NZ^3Z^4$, and
(l) —$NZ^3Z^4$,
$R^{10b}$ is selected from the group consisting of hydrogen and $C_1$-$C_6$ alkyl;
each $Z^1$ is independently selected from the group consisting of:
(i) hydrogen,
(ii) $C_1$-$C_6$ alkyl,
(iii) unsubstituted or substituted $C_2$-$C_6$ alkenyl, wherein one or more substituents are independently selected from the group consisting of cyano, —$S(=O)_2Z^2$, —$S(=O)_2NZ^3Z^4$, halogen, —$NZ^3Z^4$, 4- to 8-membered heterocycle,
(iv) $C_2$-$C_6$ alkynyl,
(v) $C_3$-$C_6$ cycloalkyl,
(vi) $C_3$-$C_6$ cycloalkenyl, and
(vii) $C_1$-$C_6$ haloalkyl;
each $Z^2$ is independently selected from the group consisting of:
(i) unsubstituted or substituted $C_1$-$C_6$ alkyl, wherein one or more substituents are independently selected from the group consisting of cyano and $C_2$-$C_6$ alkynyl;
(ii) unsubstituted or substituted $C_2$-$C_6$ alkenyl, wherein one or more substituents are independently selected from the group consisting of cyano, —$S(=O)_2Z^2$, —$S(=O)_2NZ^3Z^4$, halogen, —$NZ^3Z^4$, 4- to 8-membered heterocycle,
(iii) $C_2$-$C_6$ alkynyl,
(iv) $C_3$-$C_6$ cycloalkyl,
(v) $C_3$-$C_6$ cycloalkenyl,
(vi) $C_1$-$C_6$ haloalkyl,
(vii) unsubstituted or substituted $C_6$-$C_{10}$ aryl, wherein one or more substituents are independently selected from the group consisting of halogen, $C_1$-$C_6$ alkyl, and $C_1$-$C_6$ haloalkyl, and —$OZ^1$, and
(viii) unsubstituted or substituted $C_3$-$C_6$ cycloalkyl, wherein one or more substituents are independently selected from the group consisting of halogen, $C_1$-$C_6$ alkyl, and $C_1$-$C_6$ haloalkyl, and —$OZ^1$;
each $Z^3$ and $Z^4$ are independently selected from the group consisting of:
(i) hydrogen;
(ii) unsubstituted or substituted $C_1$-$C_6$ alkyl, wherein one or more substituents are independently selected from the group consisting of:
(a) unsubstituted or substituted $C_6$-$C_{10}$ aryl, wherein one or more substituents are independently selected from the group consisting of:
(1) halogen,
(2) cyano,
(3) $C_1$-$C_6$ alkyl,
(4) $C_3$-$C_6$ cycloalkyl,
(5) $C_1$-$C_6$ haloalkyl,
(6) —$OZ^1$,
(7) $C_2$-$C_6$ alkenyl, and
(8) $C_2$-$C_6$ alkynyl,
(b) unsubstituted or substituted $C_3$-$C_6$ cycloalkyl, wherein one or more substituents are independently selected from the group consisting of:
(1) halogen,
(2) cyano,
(3) $C_1$-$C_6$ alkyl,
(4) $C_3$-$C_6$ cycloalkyl,
(5) $C_1$-$C_6$ haloalkyl, and
(6) —$OZ^1$, (c) unsubstituted or substituted 5- to 9-membered heteroaryl, wherein one or more substituents are independently selected from the group consisting of:
  (1) halogen,
  (2) cyano,
  (3) $C_1$-$C_6$ alkyl,
  (4) $C_3$-$C_6$ cycloalkyl,
  (5) $C_1$-$C_6$ haloalkyl,
  (6) —$OZ^1$,
  (7) $C_2$-$C_6$ alkenyl, and
  (8) $C_2$-$C_6$ alkynyl,
(d) cyano,
(e) hydroxy,
(f) —$OZ^1$, and
(g) —$NZ^3Z^4$,
(iii) unsubstituted or substituted $C_2$-$C_6$ alkenyl, wherein one or more substituents are independently selected from the group consisting of cyano, —$S(=O)_2Z^2$, —$S(=O)_2NZ^3Z^4$, halogen, —$NZ^3Z^4$, 4- to 8-membered heterocycle,
(iv) $C_2$-$C_6$ alkynyl,
(v) $C_3$-$C_6$ cycloalkyl,
(vi) $C_3$-$C_6$ cycloalkenyl, and
(vii) $C_1$-$C_6$ haloalkyl;

each $Z^5$ and $Z^6$ are independently selected from the group consisting of:
  (i) hydrogen,
  (ii) $C_1$-$C_6$ alkyl, and
  (iii) $C_3$-$C_6$ cycloalkyl;

X is selected from the group consisting of —$CR^{11a}$= and —N=;
$X^1$ is selected from the group consisting of —$CR^{11b}$= and —N=;
$X^2$ is selected from the group consisting of —$CR^{11c}$= and —N=;
$X^3$ is selected from the group consisting of —$CR^{11d}$= and —N=; and
each $R^{11a}$, $R^{11b}$, $R^{11c}$, and $R^{11d}$ is independently selected from the group consisting of hydrogen, halogen, hydroxy, cyano, $C_1$-$C_6$ alkyl, $C_1$-$C_6$ haloalkyl, —OZ, and —$NZ^3Z^4$.

In another embodiment, compounds of the disclosure are compounds of Formula II:

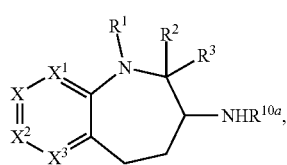

or a stereoisomer, tautomer, pharmaceutically acceptable salt, or solvate thereof, wherein $R^1$, $R^2$, $R^3$, $R^{10a}$, X, $X^1$, $X^2$, and $X^3$ are as defined in connection with Formula I.

In another embodiment, compounds of the disclosure are compounds of Formula I or II, or a stereoisomer, tautomer, pharmaceutically acceptable salt, or solvate thereof, wherein $R^{10a}$ is selected from the group consisting of —$C(=O)Z^2$ and unsubstituted or substituted $C_1$-$C_6$ alkyl; and
$Z^2$ is selected from the group consisting of:
  (i) $C_1$-$C_6$ alkyl; and
  (ii) unsubstituted or substituted $C_2$-$C_6$ alkenyl, wherein one or more substituents are independently selected from the group consisting of cyano, —$S(=O)_2Z^2$, —$S(=O)_2NZ^3Z^4$, halogen, —$NZ^3Z^4$, 4- to 8-membered heterocycle.

In another embodiment, compounds of the disclosure are compounds of Formula I or II, or a stereoisomer, tautomer, pharmaceutically acceptable salt, or solvate thereof, wherein $R^2$ and $R^3$ taken together with the carbon atom to which they are attached form a —C(=O)— group.

In another embodiment, compounds of the disclosure are compounds of Formula I or II, or a stereoisomer, tautomer, pharmaceutically acceptable salt, or solvate thereof, wherein $R^2$ and $R^3$ are hydrogen.

In another embodiment, compounds of the disclosure are compounds of Formula I or II, or a stereoisomer, tautomer, pharmaceutically acceptable salt, or solvate thereof, wherein:
X is —$CR^{11a}$=;
$X^1$ is —$CR^{11b}$=;
$X^2$ is —$CR^{11c}$=; and
$X^3$ is —$CR^{11d}$=.

In another embodiment, compounds of the disclosure are compounds of Formula III:

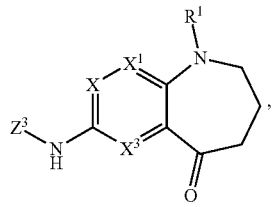

or a stereoisomer, tautomer, pharmaceutically acceptable salt, or solvate thereof, wherein $R^1$, X, $X^1$, $X^3$, and $Z^3$ are as defined in connection with Formula I.

In another embodiment, compounds of the disclosure are compounds of Formula I or III, or a stereoisomer, tautomer, pharmaceutically acceptable salt, or solvate thereof, wherein $Z^3$ is unsubstituted or substituted $C_1$-$C_6$ alkyl.

In another embodiment, compounds of the disclosure are compounds of Formula III, or a stereoisomer, tautomer, pharmaceutically acceptable salt, or solvate thereof, wherein X is —$CR^{11a}$=; $X^1$ is —$CR^{11b}$=; and $X^3$ is —$CR^{11d}$=.

In another embodiment, compounds of the disclosure are compounds of any one of Formulae I-III, or a stereoisomer, tautomer, pharmaceutically acceptable salt, or solvate thereof, wherein $R^1$ is unsubstituted or substituted $C_6$-$C_{10}$ aryl, wherein one or more substituents are independently selected from the group consisting of halogen, hydroxy, cyano, $C_1$-$C_6$ alkyl, $C_1$-$C_6$ haloalkyl, and —$OZ^1$.

In another embodiment, compounds of the disclosure are compounds of Formula I, or a stereoisomer, tautomer, pharmaceutically acceptable salt, or solvate thereof, selected from the group consisting of:
N-(2-oxo-1-(4-(trifluoromethyl)phenyl)-2,3,4,5-tetrahydro-1H-benzo[b]azepin-3-yl)acrylamide;
3-amino-1-(4-(trifluoromethyl)phenyl)-1,3,4,5-tetrahydro-2H-benzo[b]azepin-2-one;
3-((3-hydroxypropyl)amino)-1-(4-(trifluoromethyl)phenyl)-1,3,4,5-tetrahydro-2H-benzo[b]azepin-2-one;
2-((1-(4-(trifluoromethyl)phenyl)-2,3,4,5-tetrahydro-1H-benzo[b]azepin-3-yl)amino)ethan-1-ol;
2-((1-(4-(trifluoromethyl)phenyl)-2,3,4,5-tetrahydro-1H-benzo[b]azepin-3-yl)amino)ethan-1-ol;

2-((1-(4-(trifluoromethyl)phenyl)-2,3,4,5-tetrahydro-1H-benzo[b]azepin-3-yl)amino)ethan-1-ol;
7-((2-hydroxyethyl)amino)-1-(4-(trifluoromethyl)phenyl)-1,2,3,4-tetrahydro-5H-benzo[b]azepin-5-one;
7-((3-hydroxypropyl)amino)-1-(4-(trifluoromethyl)phenyl)-1,2,3,4-tetrahydro-5H-benzo[b]azepin-5-one;
N-(1-(4-(trifluoromethyl)phenyl)-2,3,4,5-tetrahydro-1H-benzo[b]azepin-3-yl)acrylamide
3-((2-hydroxyethyl)amino)-1-(4-(trifluoromethyl)phenyl)-1,3,4,5-tetrahydro-2H-benzo[b]azepin-2-one;
3-((1-(4-(trifluoromethyl)phenyl)-2,3,4,5-tetrahydro-1H-benzo[b]azepin-3-yl)amino)propan-1-ol;
3-((1-(4-(trifluoromethyl)phenyl)-2,3,4,5-tetrahydro-1H-benzo[b]azepin-3-yl)amino)propanoic acid;
1-(4-(trifluoromethyl)phenyl)-2,3,4,5-tetrahydro-1H-benzo[b]azepin-3-amine; and
N-(1-(4-(trifluoromethyl)phenyl)-2,3,4,5-tetrahydro-1H-benzo[b]azepin-3-yl)propionamide.

Preferred or particular statements (features) and embodiments of the compounds of this disclosure are set herein below. Each statement, aspect and embodiment of the disclosure so defined may be combined with any other statement, aspect and/or embodiment, unless clearly indicated to the contrary. In particular, any feature indicated as being preferred, particular or advantageous may be combined with any other features or statements indicated as being preferred, particular or advantageous. Hereto, the present disclosure is in particular captured by any one or any combination of one or more of the below numbered statements and embodiments, with any other statement, aspect and/or embodiment (which are not numbered).

Embodiment 1. A compound of Formula I.

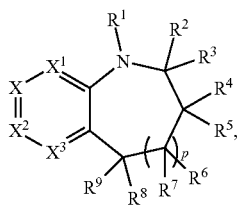

I or a stereoisomer, tautomer, pharmaceutically acceptable salt, or solvate thereof, wherein:
p is 0, 1, or 2;
$R^1$ is selected from the group consisting of:
  (i) hydrogen,
  (ii) unsubstituted or substituted $C_1$-$C_6$ alkyl, wherein one or more substituents are independently selected from the group consisting of:
    (a) unsubstituted or substituted $C_6$-$C_{10}$ aryl, wherein one or more substituents are independently selected from the group consisting of:
      (1) halogen,
      (2) cyano,
      (3) $C_1$-$C_6$ alkyl,
      (4) $C_3$-$C_6$ cycloalkyl,
      (5) $C_1$-$C_6$ haloalkyl,
      (6) —$OZ^1$,
      (7) $C_2$-$C_6$ alkenyl, and
      (8) $C_2$-$C_6$ alkynyl,
    (b) unsubstituted or substituted $C_3$-$C_6$ cycloalkyl, wherein one or more substituents are independently selected from the group consisting of:
      (1) halogen,
      (2) cyano,
      (3) $C_1$-$C_6$ alkyl,
      (4) $C_3$-$C_6$ cycloalkyl,
      (5) $C_1$-$C_6$ haloalkyl, and
      (6) —$OZ^1$,
    (c) $C_2$-$C_6$ alkynyl,
  (iii) unsubstituted or substituted $C_6$-$C_{10}$ aryl, wherein one or more substituents are independently selected from the group consisting of:
    (a) halogen,
    (b) cyano,
    (c) $C_1$-$C_6$ alkyl,
    (d) $C_3$-$C_6$ cycloalkyl,
    (e) $C_1$-$C_6$ haloalkyl,
    (f) —$OZ^1$, and
    (g) unsubstituted or substituted $C_6$-$C_{10}$ aryl, wherein one or more substituents are independently selected from the group consisting of halogen, $C_1$-$C_6$ alkyl, and $C_1$-$C_6$ haloalkyl, and —$OZ^1$,
  (iv) unsubstituted or substituted 5- to 9-membered heteroaryl, wherein one or more substituents are independently selected from the group consisting of:
    (a) halogen,
    (b) cyano,
    (c) $C_1$-$C_6$ alkyl,
    (d) $C_3$-$C_6$ cycloalkyl,
    (e) $C_1$-$C_6$ haloalkyl,
    (f) —$OZ^1$, and
    (g) unsubstituted or substituted $C_6$-$C_{10}$ aryl, wherein one or more substituents are independently selected from the group consisting of halogen, $C_1$-$C_6$ alkyl, and $C_1$-$C_6$ haloalkyl, and —$OZ^1$,
  (v) unsubstituted or substituted $C_3$-$C_6$ cycloalkyl, wherein one or more substituents are independently selected from the group consisting of:
    (a) halogen,
    (b) cyano,
    (c) $C_1$-$C_6$ alkyl,
    (d) $C_3$-$C_6$ cycloalkyl,
    (e) $C_1$-$C_6$ haloalkyl, and
    (f) —$OZ^1$,
  (vi) unsubstituted or substituted $C_3$-$C_6$ heterocycle, wherein one or more substituents are independently selected from the group consisting of:
    (a) halogen,
    (b) cyano,
    (c) $C_1$-$C_6$ alkyl,
    (d) $C_3$-$C_6$ cycloalkyl,
    (e) $C_1$-$C_6$ haloalkyl, and
    (f) —$OZ^1$,
  (vii) —$S(=O)_2Z^2$, and
  (viii) —$C(=O)Z^2$;
$R^2$ and $R^3$ are independently selected from the group consisting of hydrogen and $C_1$-$C_6$ alkyl; or
$R^2$ and $R^3$ taken together with the carbon atom to which they are attached form a —C(=O)— group;
$R^4$ is selected from the group consisting of hydrogen and —$NR^{10a}R^{10b}$;
$R^5$ is selected from the group consisting of hydrogen and $C_1$-$C_6$ alkyl;
each $R^6$ and $R^7$ is independently selected from the group consisting of hydrogen and $C_1$-$C_6$ alkyl;
$R^8$ and $R^9$ are independently selected from the group consisting of hydrogen and $C_1$-$C_6$ alkyl; or
$R^8$ and $R^9$ taken together with the carbon atom to which they are attached form a —C(=O)— group;

$R^{10a}$ is selected from the group consisting of:
- (i) —C(=O)$Z^2$
- (ii) —C(=O)O$Z^2$,
- (iii) —C(=O)N$Z^3Z^4$,
- (iv) —S(=O)$_2Z^2$,
- (v) —S(=O)$_2$N$Z^3Z^4$,
- (vi) —S(=O)(=NZ)$Z^2$,
- (vii) —S(=N$Z^5$)(=N$Z^6$)$Z^2$,
- (viii) —S(=O)(=N$Z^5$)N$Z^3Z^4$, and
- (ix) unsubstituted or substituted $C_1$-$C_6$ alkyl, wherein one or more substituents are independently selected from the group consisting of:
  - (a) cyano,
  - (b) hydroxy,
  - (c) —O$Z^1$,
  - (d) —C(=O)OH
  - (e) —C(=O)$Z^2$
  - (f) —C(=O)O$Z^2$,
  - (g) —C(=O)N$Z^3Z^4$,
  - (h) —S(=O)$_2Z^2$,
  - (i) —S(=O)$_2$N$Z^3Z^4$,
  - (j) —S(=O)(=N$Z^5$)$Z^2$,
  - (k) —S(=N$Z^5$)(=N$Z^6$)$Z^2$,
  - (k) —S(=O)(=N$Z^5$)N$Z^3Z^4$, and
  - (l) —N$Z^3Z^4$, $R^{10b}$ is selected from the group consisting of hydrogen and $C_1$-$C_6$ alkyl;

each $Z^1$ is independently selected from the group consisting of:
- (i) hydrogen,
- (ii) $C_1$-$C_6$ alkyl,
- (iii) unsubstituted or substituted $C_2$-$C_6$ alkenyl, wherein one or more substituents are independently selected from the group consisting of cyano, —S(=O)$_2Z^2$, —S(=O)$_2$N$Z^3Z^4$, halogen, —N$Z^3Z^4$, 4- to 8-membered heterocycle,
- (iv) $C_2$-$C_6$ alkynyl,
- (v) $C_3$-$C_6$ cycloalkyl,
- (vi) $C_3$-$C_6$ cycloalkenyl, and
- (vii) $C_1$-$C_6$ haloalkyl;

each $Z^2$ is independently selected from the group consisting of:
- (i) unsubstituted or substituted $C_1$-$C_6$ alkyl, wherein one or more substituents are independently selected from the group consisting of cyano and $C_2$-$C_6$ alkynyl;
- (ii) unsubstituted or substituted $C_2$-$C_6$ alkenyl, wherein one or more substituents are independently selected from the group consisting of cyano, —S(=O)$_2Z^2$, —S(=O)$_2$N$Z^3Z^4$, halogen, —N$Z^3Z^4$, 4- to 8-membered heterocycle,
- (iii) $C_2$-$C_6$ alkynyl,
- (iv) $C_3$-$C_6$ cycloalkyl,
- (v) $C_3$-$C_6$ cycloalkenyl,
- (vi) $C_1$-$C_6$ haloalkyl,
- (vii) unsubstituted or substituted $C_6$-$C_{10}$ aryl, wherein one or more substituents are independently selected from the group consisting of halogen, $C_1$-$C_6$ alkyl, and $C_1$-$C_6$ haloalkyl, and —O$Z^1$, and
- (viii) unsubstituted or substituted $C_3$-$C_6$ cycloalkyl, wherein one or more substituents are independently selected from the group consisting of halogen, $C_1$-$C_6$ alkyl, and $C_1$-$C_6$ haloalkyl, and —O$Z^1$;

each $Z^3$ and $Z^4$ are independently selected from the group consisting of:
- (i) hydrogen;
- (ii) unsubstituted or substituted $C_1$-$C_6$ alkyl, wherein one or more substituents are independently selected from the group consisting of:
  - (a) unsubstituted or substituted $C_6$-$C_{10}$ aryl, wherein one or more substituents are independently selected from the group consisting of:
    - (1) halogen,
    - (2) cyano,
    - (3) $C_1$-$C_6$ alkyl,
    - (4) $C_3$-$C_6$ cycloalkyl,
    - (5) $C_1$-$C_6$ haloalkyl,
    - (6) —O$Z^1$,
    - (7) $C_2$-$C_6$ alkenyl, and
    - (8) $C_2$-$C_6$ alkynyl,
  - (b) unsubstituted or substituted $C_3$-$C_6$ cycloalkyl, wherein one or more substituents are independently selected from the group consisting of:
    - (1) halogen,
    - (2) cyano,
    - (3) $C_1$-$C_6$ alkyl,
    - (4) $C_3$-$C_6$ cycloalkyl,
    - (5) $C_1$-$C_6$ haloalkyl, and
    - (6) —O$Z^1$,
  - (c) unsubstituted or substituted 5- to 9-membered heteroaryl, wherein one or more substituents are independently selected from the group consisting of:
    - (1) halogen,
    - (2) cyano,
    - (3) $C_1$-$C_6$ alkyl,
    - (4) $C_3$-$C_6$ cycloalkyl,
    - (5) $C_1$-$C_6$ haloalkyl,
    - (6) —O$Z^1$,
    - (7) $C_2$-$C_6$ alkenyl, and
    - (8) $C_2$-$C_6$ alkynyl,
  - (d) cyano,
  - (e) hydroxy,
  - (f) —O$Z^1$, and
  - (g) —N$Z^3Z^4$,
- (iii) unsubstituted or substituted $C_2$-$C_6$ alkenyl, wherein one or more substituents are independently selected from the group consisting of cyano, —S(=O)$_2Z^2$, —S(=O)$_2$N$Z^3Z^4$, halogen, —N$Z^3Z^4$, 4- to 8-membered heterocycle,
- (iv) $C_2$-$C_6$ alkynyl,
- (v) $C_3$-$C_6$ cycloalkyl,
- (vi) $C_3$-$C_6$ cycloalkenyl, and
- (vii) $C_1$-$C_6$ haloalkyl;

each $Z^5$ and $Z^6$ are independently selected from the group consisting of:
- (i) hydrogen,
- (ii) $C_1$-$C_6$ alkyl, and
- (iii) $C_3$-$C_6$ cycloalkyl;

X is selected from the group consisting of —C$R^{11a}$= and —N=;

$X^1$ is selected from the group consisting of —C$R^{11b}$= and —N=;

$X^2$ is selected from the group consisting of —C$R^{11c}$= and —N=;

$X^3$ is selected from the group consisting of —C$R^{11d}$= and —N=;

$X^3$ is selected from the group consisting of —C$R^{11d}$= and —N=; and each $R^{11a}$, $R^{11b}$, $R^{11c}$, and $R^{11d}$ is independently selected from the group consisting of hydrogen, halogen, hydroxy, cyano, $C_1$-$C_6$ alkyl, $C_1$-$C_6$ haloalkyl, —OZ, and —N$Z^3Z^4$.

Embodiment 2. The compound of Embodiment 1 of Formula II:

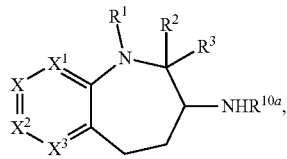

or a stereoisomer, tautomer, pharmaceutically acceptable salt, or solvate thereof.

Embodiment 3. The compound of Embodiment 1 or 2, or a stereoisomer, tautomer, pharmaceutically acceptable salt, or solvate thereof, wherein $R^{10a}$ is selected from the group consisting of —C(=O)$Z^2$ and unsubstituted or substituted $C_1$-$C_6$ alkyl; and $Z^2$ is selected from the group consisting of:
  (i) $C_1$-$C_6$ alkyl; and
  (ii) unsubstituted or substituted $C_2$-$C_6$ alkenyl, wherein one or more substituents are independently selected from the group consisting of cyano, —S(=O)$_2Z^2$, —S(=O)$_2$N$Z^3Z^4$, halogen, —N$Z^3Z^4$, 4- to 8-membered heterocycle.

Embodiment 4. The compound of any one of Embodiments 1-3, or a stereoisomer, tautomer, pharmaceutically acceptable salt, or solvate thereof, wherein $R^2$ and $R^3$ taken together with the carbon atom to which they are attached form a —C(=O)— group.

Embodiment 5. The compound of any one of Embodiments 1-3, or a stereoisomer, tautomer, pharmaceutically acceptable salt, or solvate thereof, wherein $R^2$ and $R^3$ are hydrogen.

Embodiment 6. The compound of any one of Embodiments 1-5, or a stereoisomer, tautomer, pharmaceutically acceptable salt, or solvate thereof, wherein:
  X is —C$R^{11a}$=;
  $X^1$ is —C$R^{11b}$=;
  $X^2$ is —C$R^{11c}$=; and
  $X^3$ is —C$R^{11d}$=.

Embodiment 7. The compound of Embodiment 1 of Formula III:

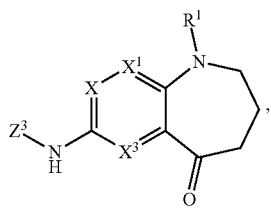

or a stereoisomer, tautomer, pharmaceutically acceptable salt, or solvate thereof.

Embodiment 8. The compound of Embodiment 1 or 7, or a stereoisomer, tautomer, pharmaceutically acceptable salt, or solvate thereof, wherein $Z^3$ is unsubstituted or substituted $C_1$-$C_6$ alkyl.

Embodiment 9. The compound of Embodiment 8, or a stereoisomer, tautomer, pharmaceutically acceptable salt, or solvate thereof, wherein:
  X is —C$R^{11a}$=;
  $X^1$ is —C$R^{11b}$=; and
  $X^3$ is —C$R^{11d}$=;

Embodiment 10. The compound of any one of Embodiments 1-9, or a stereoisomer, tautomer, pharmaceutically acceptable salt, or solvate thereof, wherein $R^1$ is unsubstituted or substituted $C_6$-$C_{10}$ aryl, wherein one or more substituents are independently selected from the group consisting of halogen, hydroxy, cyano, $C_1$-$C_6$ alkyl, $C_1$-$C_6$ haloalkyl, and —O$Z^1$.

Embodiment 11. The compound of Embodiment 1, or a stereoisomer, tautomer, pharmaceutically acceptable salt, or solvate thereof, selected from the group consisting of:
N-(2-oxo-1-(4-(trifluoromethyl)phenyl)-2,3,4,5-tetrahydro-1H-benzo[b]azepin-3-yl)acrylamide;
3-amino-1-(4-(trifluoromethyl)phenyl)-1,3,4,5-tetrahydro-2H-benzo[b]azepin-2-one;
3-((3-hydroxypropyl)amino)-1-(4-(trifluoromethyl)phenyl)-1,3,4,5-tetrahydro-2H-benzo[b]azepin-2-one;
2-((1-(4-(trifluoromethyl)phenyl)-2,3,4,5-tetrahydro-1H-benzo[b]azepin-3-yl)amino)ethan-1-ol;
2-((1-(4-(trifluoromethyl)phenyl)-2,3,4,5-tetrahydro-1H-benzo[b]azepin-3-yl)amino)ethan-1-ol;
2-((1-(4-(trifluoromethyl)phenyl)-2,3,4,5-tetrahydro-1H-benzo[b]azepin-3-yl)amino)ethan-1-ol;
7-((2-hydroxyethyl)amino)-1-(4-(trifluoromethyl)phenyl)-1,2,3,4-tetrahydro-5H-benzo[b]azepin-5-one;
7-((3-hydroxypropyl)amino)-1-(4-(trifluoromethyl)phenyl)-1,2,3,4-tetrahydro-5H-benzo[b]azepin-5-one;
N-(1-(4-(trifluoromethyl)phenyl)-2,3,4,5-tetrahydro-1H-benzo[b]azepin-3-yl)acrylamide
3-((2-hydroxyethyl)amino)-1-(4-(trifluoromethyl)phenyl)-1,3,4,5-tetrahydro-2H-benzo[b]azepin-2-one;
3-((1-(4-(trifluoromethyl)phenyl)-2,3,4,5-tetrahydro-1H-benzo[b]azepin-3-yl)amino)propan-1-ol;
3-((1-(4-(trifluoromethyl)phenyl)-2,3,4,5-tetrahydro-1H-benzo[b]azepin-3-yl)amino)propanoic acid;
1-(4-(trifluoromethyl)phenyl)-2,3,4,5-tetrahydro-1H-benzo[b]azepin-3-amine; and
N-(1-(4-(trifluoromethyl)phenyl)-2,3,4,5-tetrahydro-1H-benzo[b]azepin-3-yl)propionamide.

Embodiment 12. A pharmaceutical composition comprising the compound of any one of Embodiments 1-11, or a stereoisomer, tautomer, pharmaceutically acceptable salt, or solvate thereof, and a pharmaceutically acceptable carrier.

Embodiment 13. The compound of any one of Embodiments 1-11, or the pharmaceutical composition of Embodiment 12, for use as a medicine.

Embodiment 14. The compound of any one of Embodiments 1-11, or the pharmaceutical composition of Embodiment 12, for use in the prevention or treatment of a YAP/TAZ-TEAD activation mediated disorder in an animal, mammal or human.

Embodiment 15. The compound of Embodiment 14, or a pharmaceutical composition of Embodiment 14, wherein the YAP/TAZ-TEAD activation mediated disorders is selected from the group comprising cancer, fibrosis and YAP/TAZ-TEAD activation mediated congenital disorders.

Embodiment 16. The compound of Embodiment 15, or a pharmaceutical composition according to Embodiment 15, wherein the YAP/TAZ-TEAD activation mediated disorders is selected from lung cancer, breast cancer, head and neck cancer, oesophageal cancer, kidney cancer, bladder cancer, colon cancer, ovarian cancer, cervical cancer, endometrial cancer, liver cancer (including but not limited to cholangiocarcinoma), skin cancer, pancreatic cancer, gastric cancer, brain cancer and prostate cancer, mesotheliomas, and/or sarcomas.

Embodiment 17. A method for the prevention or treatment of a YAP/TAZ-TEAD activation mediated disorders in an animal, mammal or human comprising administering to said animal, mammal or human in need for such prevention or treatment an effective dose of the compounds of any one of Embodiments 1-11.

Embodiment 18. A method of treatment or prevention of YAP/TAZ-TEAD activation mediated disorder according to Embodiment 17 to a patient in need thereof in combination with one or more other medicines selected from the group consisting of EGFR inhibitors, MEK inhibitors, AXL inhibitors, B-RAF inhibitors, and RAS inhibitors.

More generally, the disclosure relates to the compounds of the formulae described herein and embodiments, statements and aspects thereof being useful as agents having biological activity or as diagnostic agents. Any of the uses mentioned with respect to the present disclosure may be restricted to a non-medical use, a non-therapeutic use, a non-diagnostic use, or exclusively an in vitro use, or a use related to cells remote from an animal.

Compounds of the present disclosure are small molecule YAP/TAZ-TEAD inhibitors. Small molecule YAP/TAZ-TEAD inhibitors are useful, e.g., for the treatment of cancer, including with no limitations, lung cancer, breast cancer, head and neck cancer, oesophageal cancer, kidney cancer, bladder cancer, colon cancer, ovarian cancer, cervical cancer, endometrial cancer, liver cancer (including but not limited to cholangiocarcinoma), skin cancer, pancreatic cancer, gastric cancer, brain cancer and prostate cancer, mesotheliomas, and/or sarcomas. In other embodiments, small molecule YAP/TAZ-TEAD inhibitors are useful for the treatment of cancers characterized by squamous cell carcinomas of the lung, cervix, ovaries, head and neck, oesophagus, and/or skin. In other embodiments, small molecule YAP/TAZ-TEAD inhibitors are useful for the treatment of cancers that originate from neuroectoderm-derived tissues, such as ependymomas, meningiomas, schwannomas, peripheral nerve-sheet tumors and/or neuroblastomas. In other embodiments, small molecule YAP/TAZ-TEAD inhibitors are useful for the treatment of vascular cancers, such as epithelioid haemangioendotheliomas, or for the treatment of supratentorial ependymomas or porocarcinomas. In some embodiments, the solid tumors have gain-of-function gene amplifications, gene fusions or activating mutations in the YAP1 or WWTR1 (TAZ) genes. In some embodiments the solid tumors have loss-of-function mutations or deletions in the NF2, LATS1/2, BAP1, FAT1, SAV1, and/or MST1/2 genes. In some embodiments solid tumors have gain-of-function mutations in the GNAQ and/or GNA11 genes, e.g. in uveal melanoma. In some embodiments, solid cancer are characterized by constitutive nuclear presence of YAP and/or TAZ. In some embodiments, solid cancers are characterized by the overexpression of YAP/TAZ-TEAD signature genes, including but not limited to CTGF, CYR61, AMOTL2, and/or ANKRD1.

Small molecule YAP/TAZ-TEAD inhibitors may also be useful to treat cancers that have developed resistance to prior treatments. This may include, for instance, the treatment of cancers that have developed resistance to chemotherapy, or to targeted therapy. In some embodiments, this may include the treatment of cancers that have developed resistance to inhibitors of receptor tyrosine kinases, such as EGFR (afatinib, erlotinib hydrochloride, osimertinib, gefitinib, dacomitinib, neratinib, canertinib, cetuximab) or AXL (crizotinib, cabozantinib, gilteritinib, sitravatinib, bemcentinib, dubermatinib), to components of the RAS-MAPK signaling cascade, including inhibitors of RAS itself (such as AMG510, MRTX849, BI1701963, ARS1620), inhibitors of B-RAF (sorafinib tosylate, dabrafenib, vemurafenib, regorafenib), or MEK1/2 (trametinib, selumetinib, cobimetinib, mirdametinib).

Small molecule YAP/TAZ-TEAD inhibitors may also be useful when combined, upon simultaneous administration, or subsequent administration, with other agents used for the treatment of cancer. This may include, for instance, the co-treatment with inhibitors or monoclonal antibodies targeting receptor tyrosine kinases such as EGFR (afatinib, erlotinib hydrochloride, osimertinib, gefitinib, dacomitinib, neratinib, canertinib, cetuximab) or AXL (crizotinib, cabozantinib, gilteritinib, sitravatinib, bemcentinib, dubermatinib), to components of the RAS-MAPK signaling cascade, including inhibitors of RAS itself (such as AMG510, MRTX849, BI1701963, ARS1620), inhibitors of B-RAF (sorafinib tosylate, dabrafenib, vemurafenib, regorafenib), or MEK1/2 (trametinib, selumetinib, cobimetinib, mirdametinib).

Small molecule YAP/TAZ-TEAD inhibitors may also be useful to treat a metastasized cancer. In some instances, the metastasized cancer is selected from metastasized uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma.

In some embodiments, the cancer treated could be malignant pleural mesothelioma or lung cancer.

In some embodiments, the compounds of the disclosure can be used for the treatment of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Malignant Pleural Mesothelioma

Small molecule YAP/TAZ-TEAD inhibitors may also be useful to treat malignant pleural mesothelioma, as a single agent, or in combination with inhibitors such as pemetrexed disodium, raltitrexed, carboplatin, oxaliplatin, gemcitabine, doxorubicin, or monoclonal antibodies such as bevacizumab. Combinations with checkpoint inhibitors such as pembrolizumab, atezolizumab, and/or nivolumab. Combinations with cell therapy, for instance, chimeric antigen receptor (CAR) T therapy or CAR NK therapy, which may, for instance, use mesothelin (MSLN) as an antigen. Combinations with monoclonal antibodies that, for instance, recognize mesothelin as an antigen, for instance BMS-986148, BAY 94-9343, amatuximab, and/or LMB-100.

Lung Cancer

Small molecule YAP/TAZ-TEAD inhibitors may also be useful to treat lung cancer, as a single agent, or in combination with inhibitors such as afatinib, bevacizumab, cabozantinib, ceritinib, crizotinib, erlotinib hydrochloride, osimertinib, ramucirumab, gefitinib, alectinib, trastuzumab, cetuximab, ipilimumab, trametinib, dabrafenib, vemurafenib, dacomitinib, tivantinib, and/or onartuzumab. Combinations with checkpoint inhibitors such as pembrolizumab, atezolizumab, and/or nivolumab. Combinations with cisplatin, carboplatin, paclitaxel, paclitaxel protein bound, docetaxel, gemcitabine, vinorelbine, etoposide, nintedanib, vinblastine, pemetrexed, afatinib, bevacizumab, cabozantinib, ceritinib, crizotinib, erlotinib hydrochloride, osimertinib, ramucirumab, gefitinib, necitumumab, alectinib, trastuzumab, cetuximab, ipilimumab, trametinib, dabrafenib, vemurafenib, dacomitinib, tivantinib, onartuzumab, pembrolizumab, atezolizumab, and/or nivolumab In some embodiments, small molecule YAP/TAZ-TEAD inhibitors are useful, e.g., for the treatment of congenital disorders. In some embodiments, the congenital disease is mediated by activation of transcriptional coactivator with PDZ binding motif/Yes-associated protein transcription coactivator (TAZ/YAP). In some embodiments, the congenital disease is characterized by a mutant Ga-protein. In some embodiments, the mutant Ga-protein is selected from G12, G13, Gq, G11, Gi, Go, and Gs. In some embodiments, the congenital disease is characterized by loss-of-function mutations or deletions in the NF2 gene. Exemplary congenital diseases include, but are not limited to, Sturge-Weber Syndrome, Port-Wine stain, and Neurofibromatosis. In some embodiments the congenital disease is Neurofibromatosis, including but not limited to Neurofibromatosis type 2.

In some embodiments, small molecule YAP/TAZ-TEAD inhibitors are useful, e.g., for the treatment of fibrotic disorders, such as fibrosis of the liver, the lung, the kidney, the heart or the skin. In some embodiments, fibrosis can be treated in the context of non-alcoholic fatty liver disease, primary sclerosing cholangitis, primary biliary cirrhosis, idiopathic pulmonary fibrosis, chronic kidney disease, and/or myocardial infarction injury.

The compounds of the disclosure can inhibit YAP/TAZ-TEAD transcription activation. The compounds have been shown to inhibit YAP/TAZ-TEAD transcription activity in cellular models and in an animal model. The compounds have also been shown to have an inhibitory effect on cancer cell lines that are dependent on YAP/TAZ-TEAD transcription activity and on the growth of cancer in a xenograft cancer model.

The compounds of the disclosure can optionally be bound covalently to an insoluble matrix and used for affinity chromatography (separations, depending on the nature of the groups of the compounds, for example compounds with pendant aryl are useful in hydrophobic affinity separations).

When using one or more derivatives of the formulae as defined herein:

the active ingredients of the compound(s) may be administered to the animal or mammal (including a human) to be treated by any means well known in the art, i.e. orally, intranasally, subcutaneously, intramuscularly, intradermally, intravenously, intra-arterially, parenterally or by catheterization.

the therapeutically effective amount of the preparation of the compound(s), especially for the treatment of diseases mediated by activity of YAP/TAZ-TEAD transcription in humans and other mammals (such as cancer, fibrosis and certain congenital disorders), preferably is a YAP/TAZ-TEAD transcription inhibiting amount of the compounds of the formulae, statements, aspects and embodiments as defined herein and corresponds to an amount which ensures a plasma level that is able to inhibit the YAP/TAZ-TEAD activation and is between 1 µg/ml and 100 mg/ml.

Suitable dosages of the compounds or compositions of the disclosure should be used to treat or prevent the targeted diseases in a subject. Depending upon the pathologic condition to be treated and the patient's condition, the said effective amount may be divided into several sub-units per day or may be administered at more than one day intervals.

According to a particular embodiment of the disclosure, the compounds of the disclosure may be employed in combination with other therapeutic agents for the treatment or prophylaxis of diseases mediated by activity of YAP/TAZ-TEAD transcription in humans and other mammals (such as cancer, fibrosis and certain congenital disorders). The disclosure therefore relates to the use of a composition comprising:

(a) one or more compounds of the formulae and aspects, statements and embodiments herein, and (b) one or more further therapeutic or preventive agents that are used for the prevention or treatment of cancer or fibrosis as biologically active agents in the form of a combined preparation for simultaneous, separate or sequential use.

The compound or composition can be administered concurrently with, prior to, or subsequent to the one or more additional therapeutic agents, which are different from the compound described herein and may be useful as, e.g., combination therapies.

Examples of such further therapeutic agents for use in combinations include agents that are inhibitors of:

EGFR (such as afatinib, erlotinib hydrochloride, osimertinib, gefitinib, dacomitinib, neratinib, canertinib, cetuximab), AXL (such as crizotinib, cabozantinib, gilteritinib, sitravatinib, bemcentinib, dubermatinib), components of the RAS-MAPK signaling cascade, including inhibitors of RAS itself (such as AMG510, MRTX849, BI1701963, ARS1620), B-RAF (such as sorafinib tosylate, dabrafenib, vemurafenib, regorafenib), or MEK1/2 (trametinib, selumetinib, cobimetinib, mirdametinib).

The pharmaceutical composition or combined preparation according to this disclosure may contain the compounds of the present disclosure over a broad content range depending on the contemplated use and the expected effect of the preparation. Generally, the content of the derivatives of the present disclosure of the combined preparation is within the range of 0.1 to 99.9% by weight, preferably from 1 to 99% by weight, more preferably from 5 to 95% by weight.

Those of skill in the art will also recognize that the compounds of the disclosure may exist in many different protonation states, depending on, among other things, the pH of their environment. While the structural formulae provided herein depict the compounds in only one of several possible protonation states, it will be understood that these structures are illustrative only, and that the disclosure is not limited to any particular protonation state—any and all protonated forms of the compounds are intended to fall within the scope of the disclosure.

The term "pharmaceutically acceptable salts" as used herein means the therapeutically active non-toxic salt forms which the compounds of formulae herein are able to form. Therefore, the compounds of this disclosure optionally comprise salts of the compounds herein, especially pharmaceutically acceptable non-toxic salts containing, for example, $Na^+$, $Li^+$, $K^+$, $Ca^{2+}$ and $Mg^{2+}$. Such salts may include those derived by combination of appropriate cations such as alkali and alkaline earth metal ions or ammonium and quaternary amino ions with an acid anion moiety, typically a carboxylic acid. The compounds of the disclosure may bear multiple positive or negative charges. The net charge of the compounds of the disclosure may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the disclosure, and that the disclosure encompasses the compounds in association with any type of counter ion. Moreover, as the compounds can exist in a variety of different forms, the disclosure is intended to encompass not only forms of the compounds that are in association with counter ions (e.g., dry salts), but also forms that are not in association with counter ions (e.g., aqueous or organic solutions). Metal salts typically are prepared by reacting the metal hydroxide with a compound of this disclosure. Examples of metal salts which are prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalogen acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. Furthermore, this term also includes the solvates which the compounds of formulae herein as well as their salts are able to form, such as for example hydrates, alcoholates and the like. Finally, it is to be understood that the compositions herein comprise compounds of the disclosure in their unionized, as well as zwitterionic form, and combinations with stoichiometric amounts of water as in hydrates.

Also included within the scope of this disclosure are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the disclosure also include physiologically acceptable salts thereof. Examples of physiologically acceptable salts of the compounds of the disclosure include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as $Na^+$ and $NX_4^+$ (wherein X typically is independently selected from H or a $C_1$-$C_4$ alkyl group). However, salts of acids or bases which are not physiologically acceptable may also find use, for example, in the preparation or purification of a physiologically acceptable compound. All salts, whether or not derived form a physiologically acceptable acid or base, are within the scope of the present disclosure.

As used herein and unless otherwise stated, the term "enantiomer" means each individual optically active form of a compound of the disclosure, having an optical purity or enantiomeric excess (as determined by methods standard in the art) of at least 80% (e.g. at least 90% of one enantiomer and at most 10% of the other enantiomer), preferably at least 90% and more preferably at least 98%.

The term "isomers" as used herein means all possible isomeric forms, including tautomeric and stereochemical forms, which the compounds of formulae herein may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds of formulae herein may have at least one chiral center) of the basic molecular structure, as well as the stereochemically pure or enriched compounds. More particularly, stereogenic centers may have either the R- or S-configuration, and multiple bonds may have either cis- or trans-configuration.

Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (e.g. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question.

Separation of stereoisomers is accomplished by standard methods known to those in the art. One enantiomer of a compound of the disclosure can be separated substantially free of its opposing enantiomer by a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched compound. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

The terms cis and trans are used herein in accordance with Chemical Abstracts nomenclature and include reference to the position of the substituents on a ring moiety. The absolute stereochemical configuration of the compounds of the formulae described herein may easily be determined by those skilled in the art while using well-known methods such as, for example, X-ray diffraction.

The present disclosure also includes isotopically labelled compounds, which are identical to those recited in the formulas recited herein, but for the fact that one or more atoms are replaced by an atom having an atomic mass or mass number different from the atomic mass or mass number usually found in nature. Examples of isotopes that may be incorporated into compounds of the present disclosure include isotopes of hydrogen, carbon, nitrogen, oxygen, phosphorous, sulfur, fluorine and chlorine, such as $^2$H, $^3$H, $^{13}$C, $^{11}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present disclosure and pharmaceutically acceptable salts of said compounds or which contain the aforementioned isotopes and/or other isotopes of other atoms are within the scope of this disclosure. Certain isotopically labeled compounds of the present disclosure, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, may afford certain therapeutic advantages resulting from greater metabolic stability, for example increased in vivo half-life or reduced dosage requirements and, hence, may be preferred in some circumstances. Isotopically labelled compounds of the formulas of this disclosure may generally be prepared by carrying out the procedures disclosed in the examples and preparations described herein, by substituting a readily available isotopically labelled reagent for a non-isotopically labelled reagent.

Also encompassed within the disclosure are modifications of the compounds of formula (I) or other formulas, embodiments, aspects or parts thereof or metabolites thereof using PROTAC technology (Schapira M. et al, Nat. Rev. Drug Discov. 2019, 18(12), 949-963). Specifically, the PROTAC technology designs a bifunctional small molecule, one end of which is a compound of the general formula (I) or other formulas, embodiments, aspects or parts thereof or metabolites thereof, and the other end of which is connected with a ligand of E3 ubiquitin ligase through a connecting chain, to form a target-induced protein degradation complex. Because this degradation has a catalytic effect, a lower dosage can achieve efficient degradation. The compound of the general formula (I) or other formulas, embodiments, aspects or parts thereof or metabolites thereof can be connected via a linker arm (e.g. long-chain ethylene glycol with the length of 2-10, long-chain propylene glycol with the length of 2-10 and long-chain fatty alkane with the length of 2-10) to a ligand of E3 ubiquitin ligase such as e.g. thalidomide analogs.

The compounds of the disclosure may be formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, e.g. the compositions of this disclosure can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present disclosure. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, e.g. carriers and additives which do not create permanent damage to mammals. The pharmaceutical compositions of the present disclosure may be prepared in any known manner, for instance by homogeneously mixing, coating and/or grinding the active ingredients, in a one-step or multi-steps procedure, with the selected carrier material and, where appropriate, the other additives such as surface-active agents. may also be prepared by micronisation, for instance in view to obtain them in the form of microspheres usually having a diameter of about 1 to 10 gm, namely for the manufacture of microcapsules for controlled or sustained release of the active ingredients.

Suitable surface-active agents, also known as emulgent or emulsifier, to be used in the pharmaceutical compositions of the present disclosure are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable from coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl group having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcohol amine salts of dodecylbenzene sulphonic acid or dibutyl-naphthalene sulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon groups optionally substituted with halo, phenyl, substituted phenyl or hydroxy; for instance quaternary ammonium salts containing as N-substituent at least one $C_{8-22}$alkyl (e.g. cetyl, lauryl, palmityl, myristyl, oleyl and the like) and, as further substituents, unsubstituted or halogenated lower alkyl, benzyl and/or hydroxy-lower alkyl.

A more detailed description of surface-active agents suitable for this purpose may be found for instance in "McCutcheon's Detergents and Emulsifiers Annual" (MC Publishing Crop., Ridgewood, New Jersey, 1981), "Tensid-Taschenbucw", 2 d ed. (Hanser Verlag, Vienna, 1981) and "Encyclopaedia of Surfactants, (Chemical Publishing Co., New York, 1981).

Compounds of the disclosure and their pharmaceutically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferable to present them as pharmaceutical formulations. The formulations, both for veterinary and for human use, of the present disclosure comprise at least one active ingredient, as above described, together with one or more pharmaceutically acceptable carriers therefore and optionally other therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present disclosure suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, e.g. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this disclosure may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, e.g. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this disclosure may include other agents conventional in the art having regard to the type of formulation in question, for example those suitable for oral administration may include flavoring agents.

Compounds of the disclosure can be used to provide controlled release pharmaceutical formulations containing as active ingredient one or more compounds of the disclosure ("controlled release formulations") in which the release of the active ingredient can be controlled and regulated to allow less frequency dosing or to improve the pharmacokinetic or toxicity profile of a given disclosed compound. Controlled release formulations adapted for oral administration in which discrete units comprising one or more compounds of the disclosure can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

Another embodiment of this disclosure relates to various precursor or "pro-drug" forms of the compounds of the present disclosure. It may be desirable to formulate the compounds of the present disclosure in the form of a chemical species which itself is not significantly biologically-active, but which when delivered to the animal, mammal or human will undergo a chemical reaction catalyzed by the normal function of the body of the fish, inter alia, enzymes present in the stomach or in blood serum, said chemical reaction having the effect of releasing a compound as defined herein. The term "pro-drug" thus relates to these species which are converted in vivo into the active pharmaceutical ingredient.

The pro-drugs of the compounds of the present disclosure can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used. The counterpart of the active pharmaceutical ingredient in the pro-drug can have different structures such as an amino acid or peptide structure, alkyl chains, sugar moieties and others as known in the art.

For the purpose of the present disclosure the term "therapeutically suitable pro-drug" is defined herein as "a compound modified in such a way as to be transformed in vivo to the therapeutically active form, whether by way of a single or by multiple biological transformations, when in contact with the tissues of the animal, mammal or human to which the pro-drug has been administered, and without undue toxicity, irritation, or allergic response, and achieving the intended therapeutic outcome".

More specifically the term "prodrug", as used herein, relates to an inactive or significantly less active derivative of a compound such as represented by the structural formulae herein described, which undergoes spontaneous or enzymatic transformation within the body in order to release the pharmacologically active form of the compound. For a comprehensive review, reference is made to Rautio J. et al. ("Prodrugs: design and clinical applications" Nature Reviews Drug Discovery, 2008, doi: 10.1038/nrd2468).

The compounds of the disclosure can be prepared while using a series of chemical reactions well known to those skilled in the art, altogether making up the process for preparing said compounds and exemplified further. The processes described further are only meant as examples and by no means are meant to limit the scope of the present disclosure.

EXAMPLES

General Syntheses

The compounds of the present disclosure may be prepared according to the general procedure outlined in Scheme 1.

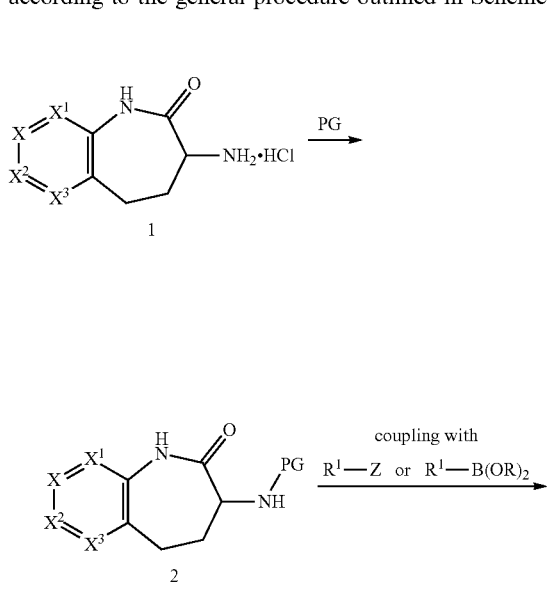

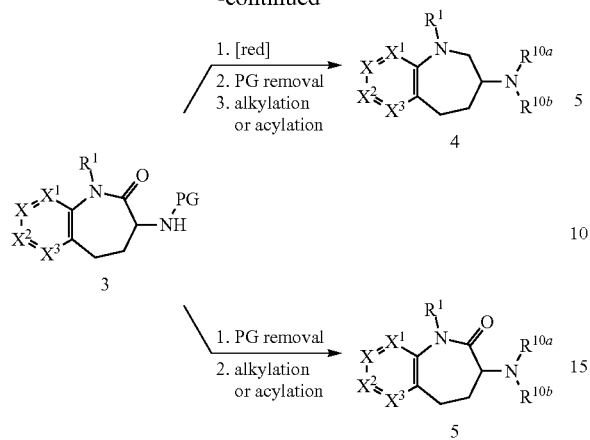

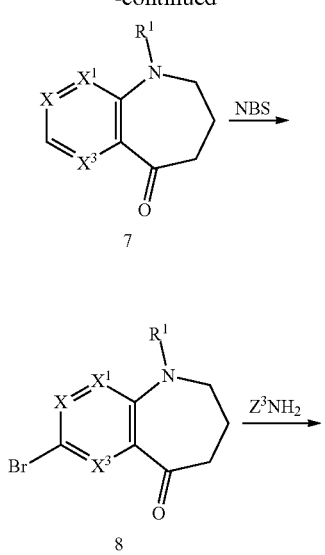

Scheme 1: all $R^1$, $R^{10a}$, $R^{10b}$, X, $X^1$, $X^2$ and $X^3$ are as described for the compounds of the present invention and its embodiments and formulae. Z=Halogen; R=H, alkyl; PG=protecting group.

Substituted 3-amino-1,3,4,5-tetrahydro-2H-benzo[b]azepin-2-one 1 may be N-protected to provide intermediates of general formula 2 following procedures known to the skilled in the art (e.g. PG=Boc or PMB). More information can be found in T. W. Greene and P. G. M. Wuts in Protective Groups in Organic Chemistry, 3$^{rd}$ ed., John Wiley and Sons, 1999. Intermediates of general formula 2 may be reacted with appropriate coupling agents selected from, but not limited to, halo(hetero)aryls, boronic acids, boronic esters, in combination with corresponding Pd or Cu catalysts to afford compounds of general formula 3. Compounds of interest having a general formula 4 may be obtained from derivatives of general formula 3 by reduction (e.g. treatment with BH$_3$·THF, or BH$_3$·SMe$_2$ and the like) and protecting group removal, followed by reaction with acyl chlorides in the presence of a base (e.g. TEA, DIPEA, NaHCO$_3$ and the like) in a suitable solvent (e.g. CH$_2$Cl$_2$, 1,4-dioxane and the like), or by reaction with alkyl halides in the presence of a base (e.g. K$_2$CO$_3$, TEA, DIPEA and the like) in a aprotic solvent (e.g. CH$_2$Cl$_2$, ACN and the like). Compounds of interest having a general formula 5 may be obtained from derivatives of general formula 3 by protecting group removal followed by reaction with acyl chlorides in the presence of a base (e.g. TEA, DIPEA, NaHCO$_3$ and the like) in a suitable solvent (e.g. CH$_2$Cl$_2$, 1,4-dioxane and the like), or by reaction with alkyl halides in the presence of a base (e.g. K$_2$CO$_3$, TEA, DIPEA and the like) in a aprotic solvent (e.g. CH$_2$Cl$_2$, ACN and the like).

In another embodiment, compounds of the present disclosure may also be synthesized according to the general procedure outlined in Scheme 2.

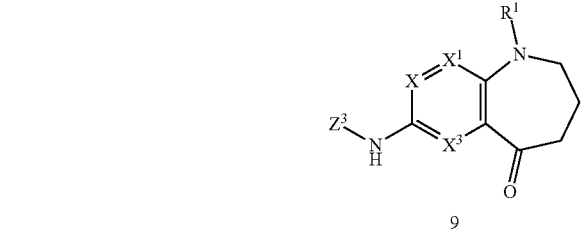

Scheme 2: all $R^1$, X, $X^1$, $X^3$ and $Z^3$ are as described for the compounds of the present invention and its embodiments and formulae. Z=Halogen; R=H, alkyl.

Substituted 1,2,3,4-tetrahydro-5H-benzo[b]azepin-5-one 6 may be reacted with appropriate coupling agents selected from, but not limited to, halo(hetero)aryls, boronic acids, boronic esters, in combination with corresponding Pd or Cu catalysts to afford compounds of general formula 7. Intermediates of general formula 8 may be obtained by bromination of intermediates of general formula 7 (e.g. treatment with NBS and the like). Intermediates of general formula 8 may be reacted with appropriate substituted amines in combination with corresponding Pd or Cu catalysts to afford compounds of interest having a general formula 4.

In another embodiment, compounds of the present disclosure may also be synthesized according to the general procedure outlined in Scheme 3.

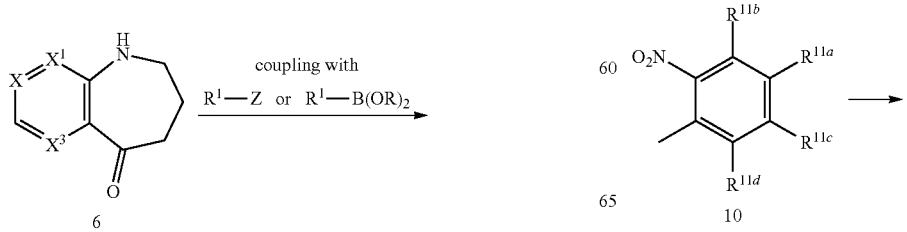

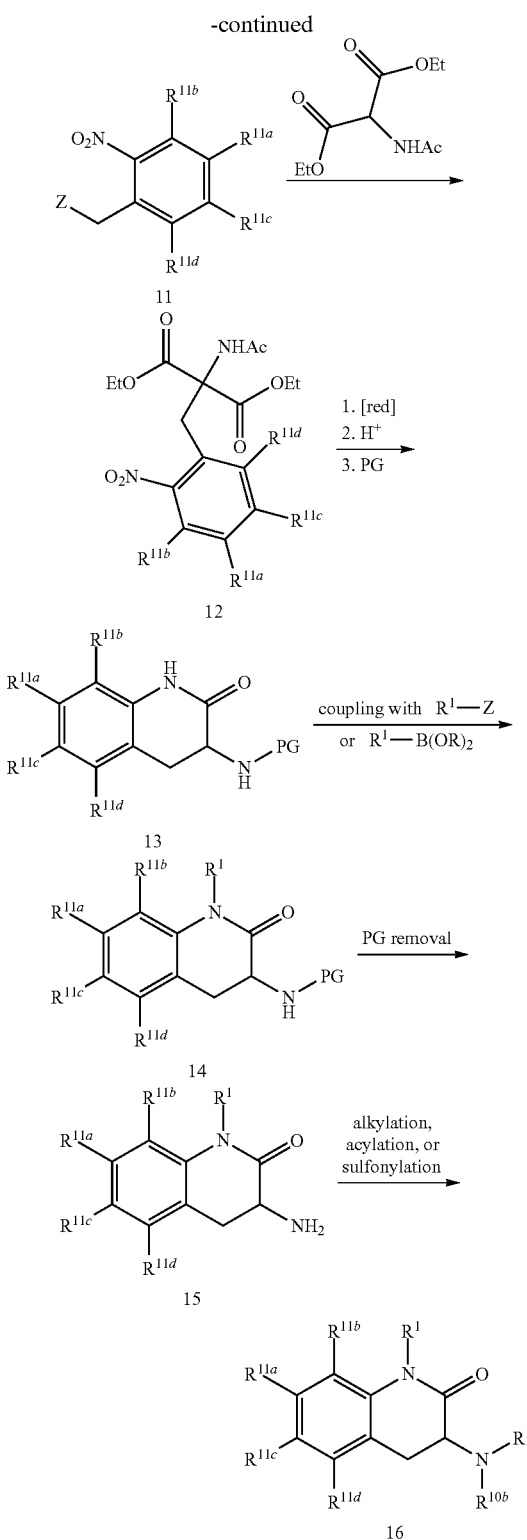

Scheme 3: all $R^{10a}$, $R^{10b}$, $R^{11a}$, $R^{11b}$, $R^{11c}$, $R^{11d}$, and $R^1$ are as described for the compounds of the present invention and its embodiments and formulae. Z=Halogen; R=H, alkyl; PG=protecting group.

Substituted 1-(halomethyl)-2-nitrobenzenes of general formula 11 (Z=Cl, Br), commercially available or synthesized from 1-methyl-2-nitrobenzene 10 by procedures known to the skilled in the art, may be reacted with diethyl 2-acetamidomalonate in the presence of a base (e.g. KOH, NaOEt, NaH, $K_2CO_3$ and the like) in a suitable solvent (e.g. MeOH, EtOH, DMF and the like) at a temperature raising from 50° C. to 100° C. to provide intermediates of general formula 12. Bicycles of general formula 13 may be obtained by reduction of the nitro moiety of intermediates of general formula 3 in a suitable solvent (e.g. MeOH, EtOH and the like) at a temperature raising from 50° C. to 100° C. followed by refluxing in concentrated acid (e.g. HCl and the like). More information can be found in WO2010/116270. Introduction of the N-protecting group to provide intermediates of general formula 13 may be performed following procedures known to the skilled in the art (e.g. PG=Boc or PMB). More information can be found in T. W. Greene and P. G. M. Wuts in Protective Groups in Organic Chemistry, 3$^{rd}$ ed., John Wiley and Sons, 1999. Intermediates of general formula 13 may be reacted further with appropriate coupling agents selected from, but not limited to, halo(hetero)aryls, boronic acids, boronic esters, in combination with corresponding Pd or Cu catalysts to afford compounds of general formula 14. More information can be found in *Synlett* 2008, 614 and *Organic and Biomolecular Chemistry* 2017, 9288. Removal of the N-protecting group to provide intermediates of general formula 15 may be performed following procedures known to the skilled in the art (e.g. PG=Boc or PMB). Compounds of interest having a general formula 16 may be obtained from derivatives of general formula 15 by reaction with acyl chlorides in the presence of a base (e.g. TEA, DIPEA, $NaHCO_3$ and the like) in a suitable solvent (e.g. $CH_2Cl_2$, 1,4-dioxane and the like). Alternatively, compounds of interest having a general formula 16 may be obtained from derivatives of general formula 15 by reaction with alkyl halides in the presence of a base (e.g. $K_2CO_3$, TEA, DIPEA and the like) in a suitable solvent (e.g. $CH_2Cl_2$, ACN and the like). Sulfonamide derivatives of general formula 16 may be obtained from derivatives of general formula 15 by reaction with sulfonyl chlorides in the presence of a base (e.g. TEA, DIPEA and the like) in a suitable solvent (e.g. $CH_2Cl_2$, ACN and the like).

Alternatively, compounds of the present disclosure may also be synthesized according to the general procedure outlined in Scheme 4.

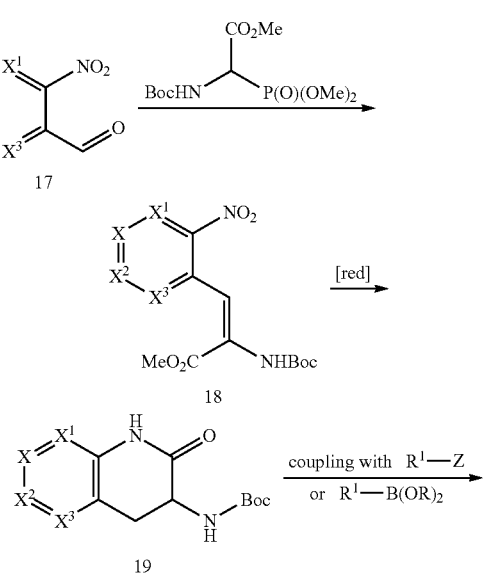

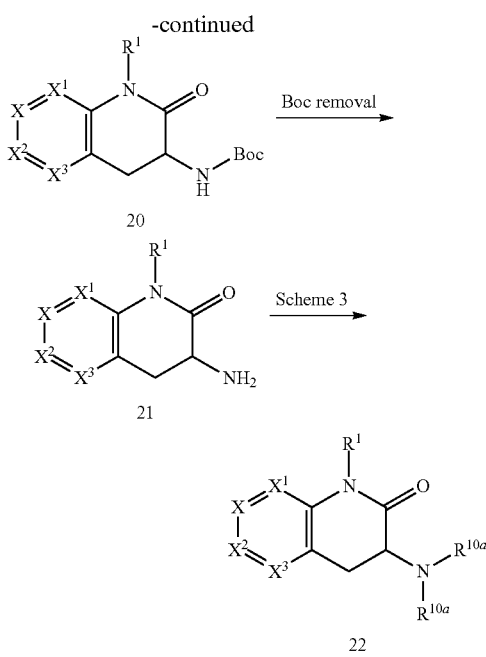

Scheme 4: all $R^1$, $R^{10a}$, $R^{10b}$, X, $X^1$, $X^2$ and $X^3$ are as described for the compounds of the present invention and its embodiments and formulae. Z=Halogen; R=H, alkyl.

Nitro heteroaryl carbaldehydes of general formula 17, commercially available or synthesized by procedures known to the skilled in the art, may be condensed with methyl 2-((tert-butoxycarbonyl)amino)-2-(dimethoxyphosphoryl) acetate in the presence of a tetramethylguanidine and in a suitable solvent (e.g. THF, 1,4-dioxane, and the like) at a temperature raising from −78° C. to room temperature to provide intermediates of general formula 18. More information can be found in WO2005/020987 and WO2006/059164. Bicycles of general formula 19 may be obtained by catalytic (Pd/C) hydrogenation of intermediates of general formula 18 in a suitable solvent (e.g. MeOH, EtOH and the like) at room temperature. Intermediates of general formula 19 may be reacted further with appropriate coupling agents selected from, but not limited to, halo(hetero)aryls, boronic acids, boronic esters, in combination with corresponding Pd or Cu catalysts to afford compounds of general formula 20. Compounds of interest having a general formula 22 may be obtained from derivatives of general formula 20 by removal of the N-protecting group via procedures known to the skilled in the art (e.g. treatment with a an acid (e.g. HCl, TFA and the like)), followed by reactions as described in Scheme 3.

The general schemes depicted above should be considered as non-limiting examples. It will be understood that compounds of the invention may be obtained through other methods which are known to people skilled in the art.

Abbreviations used in the instant specification, particularly in the schemes and examples, are as follows: Ac—Acetyl, ACN—acetonitrile, aq—Aqueous, AIBN—Azobisisobutyronitrile, $BH_3 \cdot SMe$—Borane dimethyl sulfide complex, BINAP—2,2'-Bis(diphenylphosphino)-1,1'-binaphthyl, Boc—tert-butyloxycarbonyl, $Boc_2O$—Di-tert-butyl dicarbonate, BPO—Benzoyl peroxide, $CCl_4$ Carbon tetrachloride, $Cs_2CO_3$—Caesium carbonate, $CDCl_3$—Deuterated chloroform, $CHCl_3$—Chloroform, Conc-Concentrated, CuI—Copper iodide, $Cu(OAc)_2$—Copper(II)acetate, DCM—Dichloromethane, DEA—Diethylamine, DIPEA—N,N-Diisopropylethylamine, DMAP—4-Dimehtylaminopyridine, DMF—N,N-Dimethylformamide, DMF-DMA—N,N-dimethylaminoformamide dimethyl acetale, DMSO—Dimethyl sulfoxide, $DMSO\text{-}d_6$—Deuterated dimethyl sulfoxide, En—Enantiomer, $Et_2O$—Diethyl ether, EtOH—Ethanol, EtOAc—Ethyl acetate, Eq—Equivalent, FA—Formic acid, Fe—Iron, h—Hour, HCl—Hydrogen chloride, $K_2CO_3$—Potassium carbonate, KI—Potassium iodide, LAH—Lithiumaluminiumhydride, $LiOH \cdot H_2O$—Lithium hydroxide monohydrate, MeOH—methanol, min.—Minute, $NaBH_4$—Sodium borohydride, NaOEt—Sodium ethoxide, NaOtBu—Sodium tert-butoxide, $Na_2CO_3$—Sodium carbonate, $NaHCO_3$—Sodium bicarbonate, $NaIO_4$—Sodium periodate, $Na_2SO_4$—Sodium sulfate, NBS—N-Bromosuccinimide, $(NH_4)HCO_3$—Ammonium bicarbonate, $NH_4Cl$—Ammonium chloride, Pd/C—Palladium on carbon, $Pd(OAc)_2$—Palladium(II)acetate, RF—Retention factor, RT—Room temperature, sat—Saturated, SFC—Supercritical fluid chromatography, TEA—Triethylamine, p-Terphenyl—1,4-Diphenylbenzene, THF—Tetrahydrofurane, TFA—Trifluoroacetic acid, TLC—thin layer chromatography.

TABLE 1

Structures of compound of the disclosure and their respective codes.

| Cpd. No. | Structure | Name |
|---|---|---|
| 001 | 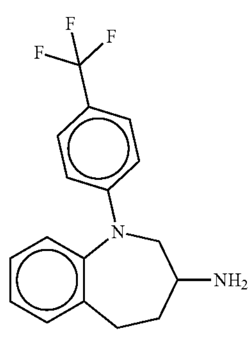 | 1-(4-(trifluoromethyl)phenyl)-2,3,4,5-tetrahydro-1H-benzo[b]azepin-3-amine |

TABLE 1-continued

Structures of compound of the disclosure and their respective codes.

| Cpd. No. | Structure | Name |
|---|---|---|
| 002 | 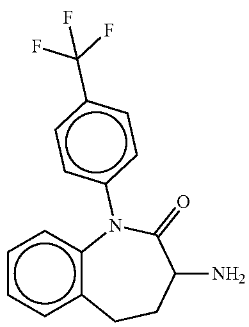 | 3-amino-1-(4-(trifluoromethyl)phenyl)-1,3,4,5-tetrahydro-2H-benzo[b]azepin-2-one |
| 003 | 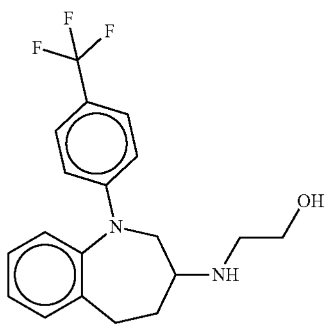 | 2-((1-(4-(trifluoromethyl)phenyl)-2,3,4,5-tetrahydro-1H-benzo[b]azepin-3-yl)amino)ethan-1-ol |
| 003-En1 | 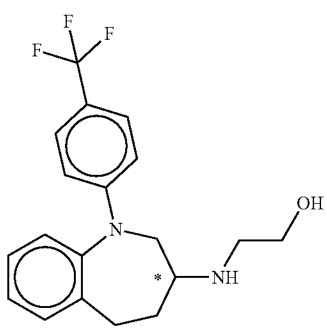 | (R)- or (S)-2-((1-(4-(trifluoromethyl)phenyl)-2,3,4,5-tetrahydro-1H-benzo[b]azepin-3-yl)amino)ethan-1-ol |
| 003-En2 | 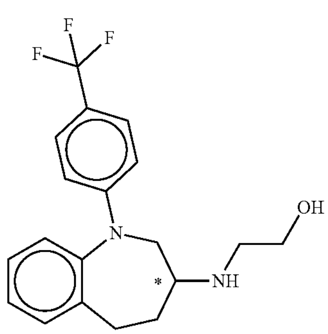 | (R)- or (S)-2-((1-(4-(trifluoromethyl)phenyl)-2,3,4,5-tetrahydro-1H-benzo[b]azepin-3-yl)amino)ethan-1-ol |

TABLE 1-continued

Structures of compound of the disclosure and their respective codes.

| Cpd. No. | Structure | Name |
|---|---|---|
| 004 | 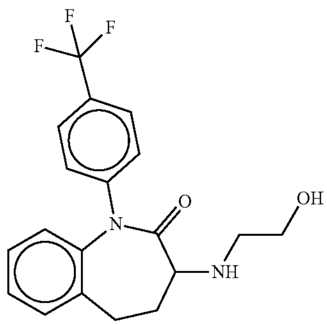 | 3-((2-hydroxyethyl)amino)-1-(4-(trifluoromethyl)phenyl)-1,3,4,5-tetrahydro-2H-benzo[b]azepin-2-one |
| 005 | 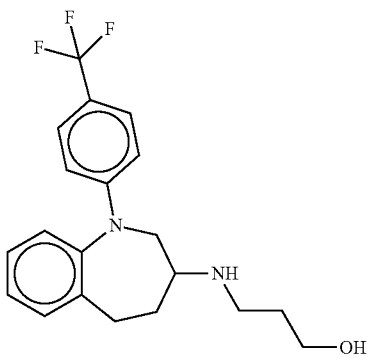 | 3-((1-(4-(trifluoromethyl)phenyl)-2,3,4,5-tetrahydro-1H-benzo[b]azepin-3-yl)amino)propan-1-ol |
| 006 | 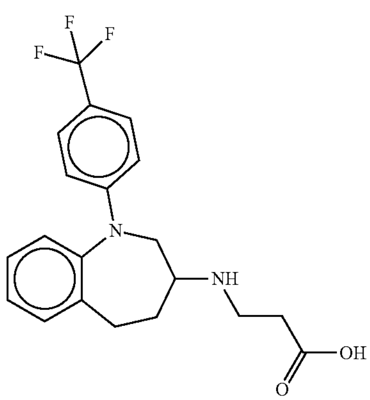 | 3-((1-(4-(trifluoromethyl)phenyl)-2,3,4,5-tetrahydro-1H-benzo[b]azepin-3-yl)amino)propanoic acid |
| 007 | 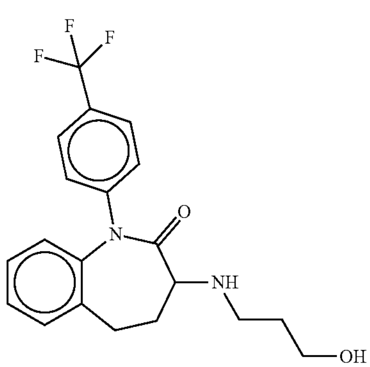 | 3-((3-hydroxypropyl)amino)-1-(4-(trifluoromethyl)phenyl)-1,3,4,5-tetrahydro-2H-benzo[b]azepin-2-one |

TABLE 1-continued

Structures of compound of the disclosure and their respective codes.

| Cpd. No. | Structure | Name |
| --- | --- | --- |
| 008 | 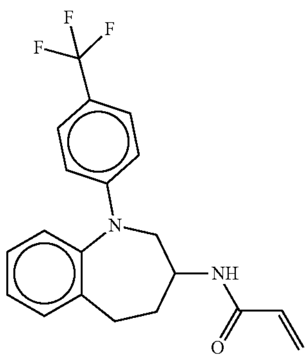 | N-(1-(4-(trifluoromethyl)phenyl)-2,3,4,5-tetrahydro-1H-benzo[b]azepin-3-yl)acrylamide |
| 008-En1 | 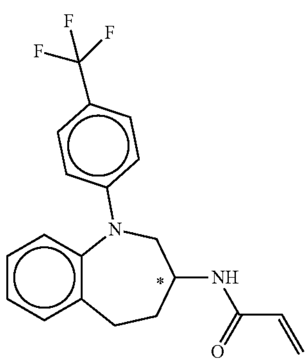 | (R)- or (S)-N-(1-(4-(trifluoromethyl)phenyl)-2,3,4,5-tetrahydro-1H-benzo[b]azepin-3-yl)acrylamide |
| 008-En2 | 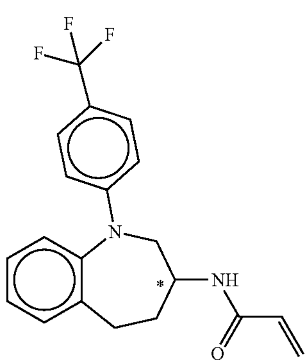 | (R)- or (S)-N-(1-(4-(trifluoromethyl)phenyl)-2,3,4,5-tetrahydro-1H-benzo[b]azepin-3-yl)acrylamide |
| 009 | 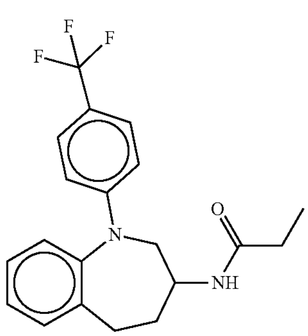 | N-(1-(4-(trifluoromethyl)phenyl)-2,3,4,5-tetrahydro-1H-benzo[b]azepin-3-yl)propionamide |

TABLE 1-continued

Structures of compound of the disclosure and their respective codes.

| Cpd. No. | Structure | Name |
|---|---|---|
| 010 | 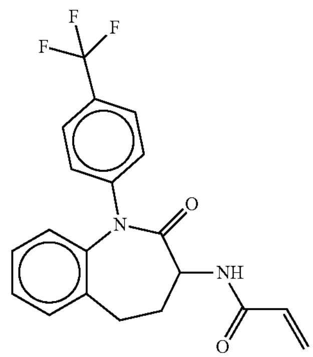 | N-(2-oxo-1-(4-(trifluoromethyl)phenyl)-2,3,4,5-tetrahydro-1H-benzo[b]azepin-3-yl)acrylamide |
| 011 | 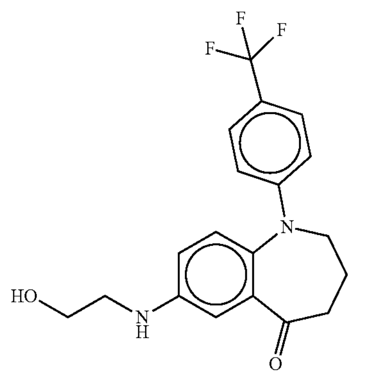 | 7-((2-hydroxyethyl)amino)-1-(4-(trifluoromethyl)phenyl)-1,2,3,4-tetrahydro-5H-benzo[b]azepin-5-one |
| 012 | 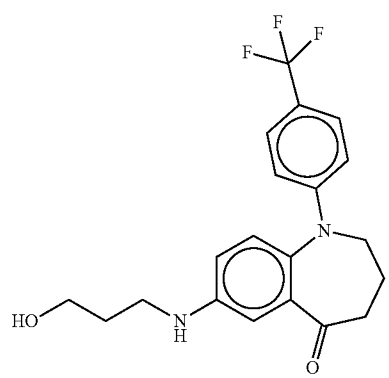 | 7-((3-hydroxypropyl)amino)-1-(4-(trifluoromethyl)phenyl)-1,2,3,4-tetrahydro-5H-benzo[b]azepin-5-one |
| 013 | 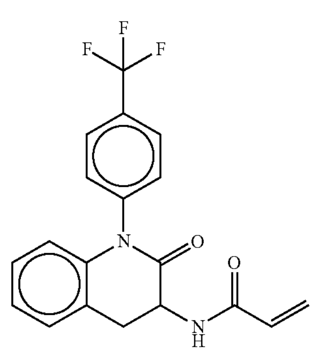 | N-(2-oxo-1-(4-(trifluoromethyl)phenyl)-1,2,3,4-tetrahydroquinolin-3-yl)acrylamide |

TABLE 1-continued

Structures of compound of the disclosure and their respective codes.

| Cpd. No. | Structure | Name |
|---|---|---|
| 014 | 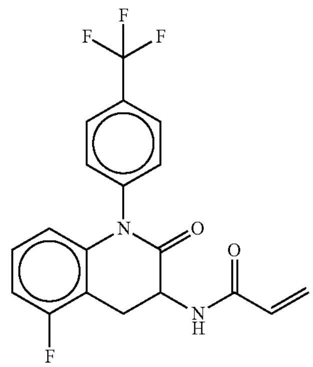 | N-(5-fluoro-2-oxo-1-(4-(trifluoromethyl)phenyl)-1,2,3,4-tetrahydroquinolin-3-yl)acrylamide |
| 015 | 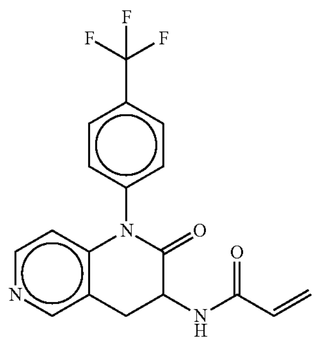 | N-(2-oxo-1-(4-(trifluoromethyl)phenyl)-1,2,3,4-tetrahydro-1,6-naphthyridin-3-yl)acrylamide |

Compounds having an asymmetric carbon atom marked with an "*" were isolated as a single (R)- or (S)-enantiomer, but the absolute stereochemistry of these compounds has not been determined.

These examples are provided for the purpose of illustrating the present disclosure and by no means should be interpreted to limit the scope of the present disclosure.

Part A: Experimental Chemistry Procedures

All starting materials which are not explicitly described were either commercially available (the details of suppliers such as for example Acros, Avocado, Aldrich, Fluka, FluoroChem, MatrixScientific, Maybridge, Merck, Sigma, etc. can be found in the SciFinder® Database for example) or the synthesis thereof has already been described precisely in the specialist literature (experimental guidelines can be found in the Reaxys® Database or the SciFinder® Database respectively, for example) or can be prepared using the conventional methods known to the person skilled in the art.

The reactions were, if necessary, carried out under an inert atmosphere (mostly argon and $N_2$). The number of equivalents of reagents and the amounts of solvents employed as well as the reaction temperatures and times can vary slightly between different reactions carried out by analogous methods. The work-up and purification methods were adapted according to the characteristic properties of each compound and can vary slightly for analogous methods. The yields of the compounds prepared are not optimized.

The indication "equivalents" ("eq." or "eq" or "equiv.") means molar equivalents, "RT" or "rt" means room temperature T (23±7° C.), "M" are indications of concentration in mol/l, "sol." means solution, "conc." means concentrated. The mixing ratios of solvents are usually stated in the volume/volume ratio.

To perform reactions under microwave radiation a CEM Microwave (Discover SP) was employed (Heating rate: 2-6° C./sec; Temperature: 30-300° C. volume-independent infrared (IR) and 80-300° C. Fiber optic (FO) temperature measurement; Pressure: 0-435 psi, ActiVent™ technology; Power: 0-300 W; Magnetron frequency: 2450 MHz; Reaction agitation: electromagnetic stirring; Air Cooling: ≥25 psi (20 L/min flow); System control: Synergy™ software).

Key analytical characterization was carried out by means of $^1$H-NMR spectroscopy and/or mass spectrometry (MS, m/z for [M+H]$^+$ and/or [M−H]$^−$) for all the exemplary compounds and selected intermediate products. In certain cases, where e.g. regioisomers and/or diastereomers could be/were formed during the reaction, additional analytics, such as, e.g. $^{13}$C NMR and NOE (nuclear overhauser effect) NMR experiments were in some cases performed.

Analytical instruments employed were e.g. for NMR analysis a BRUKER AVANCE 400 MHz (Software Topspin) or a VARIAN MR 400 MHz (VNMRJ Sofware) machine was employed. For LC/MS analysis e.g. an Acquity UPLC H-Class, Mass: Acquity SQD2 Detector (ESI), an Acquity UPLC, Mass: Quatro premier XE Detector (ESI), an Acquity UPLC, Mass: Waters Xevo TQ-S Detector (ESI/ESCI), or an Alliance Waters 2695, Mass: Quattromicro™ (ESCI) multimode ionization was employed. Analytical HPLCs were measured e.g. on Alliance Waters 2695). Analytical SFC were performed e.g. on a PIC solution (Software: SFC PIC Lab Online), a WATERS-X5 (Software MASSLYNX), or a WATERS-UPC2 (Empower).

Preparative HPLC were performed e.g. on a Waters 2545 (Software Empower), a Gilson (Software Trilution), or a Shimadzu (Software LC Solution). Preparative SFC were performed e.g. on a Waters Thar SFC-80 (Software Chromscope), Waters Thar SFC-150 (Software Chromscope), Waters Thar SFC-200 (Software Chromscope), or a PIC SFC-175 (Software SFC PIC Lab Online).

Structures of example compounds that contain stereocenters are drawn and named with absolute stereochemistry, if known. In case of unknown absolute stereochemistry the compounds can be either racemic, a mixture of diastereomers, a pure diastereomer of unknown stereochemistry, or a pure enantiomer of unknown stereochemistry. Dia 1 and Dia 2 means that diastereoisomers were separated but the stereochemistry is unknown. En 1 and En 2 means that both enantiomers were separated but the absolute configuration is unknown. No suffix given after the compound code means that a compound containing stereocenters was obtained as a racemic mixture or a mixture of diastereomers, respectively, unless the chemical name of the compound specifies the exact stereochemistry.

The LC/MS analysis mentioned in the experimental part were also performed on a Alliance Waters 2695 HPLC (equipped with a PDA detector) connected to a mass spectrometer mass spectrometer Waters Quattromicro (ESCI, multimode ionization). (Method L in the table below).

Conditions used for the HPLC analysis in the experimental part. The LC/MS analysis mentioned in the experimental part were performed on a Alliance Waters 2695 HPLC (equipped with a PDA detector) connected to a mass spectrometer Waters Quattromicro (ESCI, multimode ionization). The separations were performed with a Acquity BEH C18 (1.7 µm, 2.1×50 mm) column and a X-Bridge C18, (3.5 µm, 4.6×75 mm) column thermostated to 30-35° C. and the PDA acquisition wavelength was set in the range of 210-400 nm (Acquisition Software: MassLynx) (Method L in the table below). Elutions were carried out with the methods described in the following tables. For Methods L1, Solvent A: FA LC-MS grade 0.05% in milliQ water. Solvent B: FA LC-MS grade 0.05% in ACN LC-MS grade. For Method L2, Solvent A: 5 mM NH$_4$HCO$_3$ in milliQ water. Solvent B: ACN LC-MS grade. For Method L3, Solvent A: TFA LC-MS grade 0.05% in milliQ water. Solvent B: MeOH LC-MS grade.

| HPLC Method | System | Time (min) | Solvents A (%) | B (%) | Flow (mL/min) | Column |
|---|---|---|---|---|---|---|
| L1 | Alliance Waters 2695 HPLC | 0 | 97 | 3 | 0.6 | Acquity BEH |
|  |  | 0.4 | 97 | 3 | 0.6 | C18 (1.7 µm, |
|  |  | 3.2 | 2 | 98 | 0.6 | 2.1 × 50 mm) |
|  |  | 3.8 | 2 | 98 | 0.6 | (0.05% FA in |
|  |  | 4.2 | 97 | 3 | 0.6 | solvents A and |
|  |  | 4.5 | 97 | 3 | 0.6 | B) |
| L2 | Alliance Waters 2695 HPLC | 0 | 95 | 5 | 1.3 | X-Bridge C18, |
|  |  | 0.5 | 95 | 5 | 1.3 | (3.5 µm, |
|  |  | 1.0 | 85 | 15 | 1.3 | 4.6 × 75 mm) |
|  |  | 4.0 | 2 | 98 | 1.3 | (5 mM |
|  |  | 7.0 | 2 | 98 | 1.3 | NH$_4$HCO$_3$ in |
|  |  | 7.5 | 95 | 5 | 1.3 | solvents A) |
|  |  | 8.0 | 95 | 5 | 1.3 |  |
| L3 | Alliance Waters 2695 HPLC | 0 | 97 | 3 | 0.45 | Acquity BEH |
|  |  | 0.4 | 97 | 3 | 0.45 | C18 |
|  |  | 12.5 | 0 | 100 | 0.45 | (1.7 µm, |
|  |  | 13.5 | 0 | 100 | 0.45 | 2.1 × 100 mm) |
|  |  | 14 | 97 | 3 | 0.45 | (0.05% TFA in |
|  |  | 15 | 97 | 3 | 0.45 | solvent A) |

Conditions used for the SFC analysis in the experimental part. The SFC analysis mentioned in the experimental part were performed on a WATERS Acquity UPC2 QDa (Empower-3 Sofware) equipped with a Acquity PDA and an Acquity QDa Detector. The separations were performed with a Chiralpak AD-3 (3 µm, 4.6×150 mm) and a Chiralcel OD-3 (3 µm, 4.6×150 mm) column; $C_{O2}$ as the mobile phase and MeOH as the co-solvent. The column was thermostated at 30° C. Elutions were carried out with the methods described in the following table.

| SCF Method | Column and conditions |
|---|---|
| S1 | Column: Chiralpak AD-3 (3 µm, 4.6 × 150 mm); % $CO_2$: 90; co-solvent: 10 (0.5% DEA in MeOH); Flow: 3 g/min; ABPR: 1500 psi; Temperature: 30° C. |
| S2 | Column: Chiralcel OD-3 (3 µm, 4.6 × 150mm); % $CO_2$: 80; co-solvent: 20 (0.5% DEA in MeOH); Flow: 3 g/min; ABPR: 1500 psi; Temperature: 30° C. |

Preparative HPLC purifications mentioned in this experimental part have been carried out with the following system: on a Waters 2545 (Empower software, 2996 PDA detector, 2707 autosampler), a Gilson (Software Trilution, 171 DAD detector, GX-271 autosampler), or a Shimadzu (Software LC Solution, CMB-20A detector, SIL-10AP autosampler). The separations were performed with a Luna C18 (5 µm, 21.2×250 mm), a X-Bridge C18 (5 µm, 29×250 mm or 5 µm, 19×150 mm) and a Primesep (5 µm, 20×120 mm) column. Elutions were carried out with columns and solvents described in the following table. Gradients systems for each individual compound were employed using the solvents mentioned in the table. Detection wavelengths were fixed at 210 and 254 nm.

| HPLC Method | Column and conditions |
|---|---|
| H1 | Luna C18 (5 µm, 21.2 × 250 mm); Solvent A: 10 mM (NH$_4$)HCO$_3$ in water; Solvent B: ACN; Flow: 15 mL/min. |

| HPLC Method | Column and conditions |
|---|---|
| H2 | X-Bridge C18 (5 µm, 19 × 150 mm) or X-Bridge C18 (5 µm, 19 × 250 mm); Solvent A: 10 mM (NH$_4$)HCO$_3$ in water; Solvent B: ACN; Flow: 15 mL/min. |
| H3 | Primesep (5 µm, 20 × 250 mm); Solvent A: 0.1% FA in water; Solvent B: ACN; Flow: 14 mL/min. |

Preparative SFC purifications mentioned in this experimental part have been carried out with the following system: a Waters Thar SFC-80 or a Thar SCF-200 (Software Chromscope) equipped with a UV/PDA detector and a modifier stream injection mode. The separations were performed with a Chiralpak AD-H (5 µm, 30×250 mm) column; CO$_2$ as the mobile phase and MeOH as the co-solvent. The column was thermostated at 30° C. Detection wavelengths were fixed at 214 nm. Elutions were carried out with the methods described in the following table.

| Prep SFC Method | Column and conditions |
|---|---|
| K1 | Chiralpak AD-H (5 µm, 30 × 250 mm); % CO$_2$: 90; % co-solvent: 10 (10% NH$_3$ in MeOH); Flow: 60 g/min; ABPR: 1500 psi; Temperature: 30° C. |

Example 1: Synthesis of 1-(4-(trifluoromethyl)phenyl)-2,3,4,5-tetrahydro-1H-benzo[b]azepin-3-amine (Cpd. No. 001)

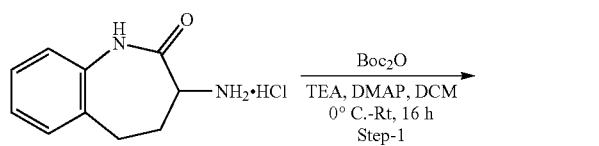

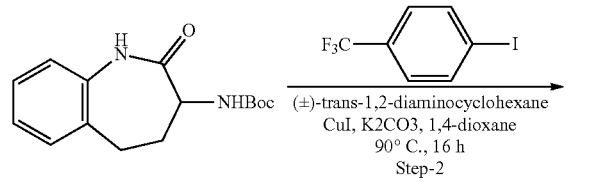

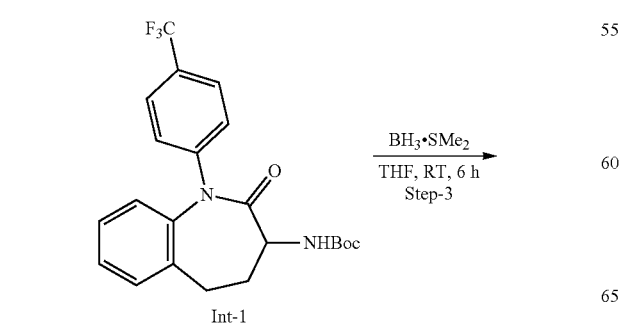

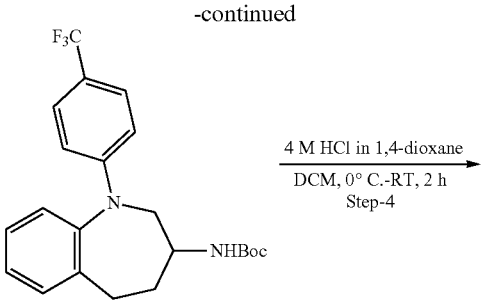

Step 1: A solution of 3-amino-1,3,4,5-tetrahydro-2H-benzo[b]azepin-2-one hydrochloride (5.3 g, 25 mmol), Boc$_2$O (8.18 g, 37.5 mmol), DMAP (10 mg) and TEA (6.37 g, 62.5 mmol) in DCM (50 mL) was stirred at RT for 16 h. Progress of the reaction was monitored by TLC. TLC mobile phase: 5% MeOH in DCM, RF: 0.43, TLC detection: UV. Reaction mixture was diluted with H$_2$O (300 mL) and extracted with DCM (300 mL). The organic layer was washed with brine (300 mL), dried over anhydrous Na$_2$SO$_4$ and concentrated under reduced pressure. The crude product (7.5 g, LC/MS 81%) was purified by normal phase flash column chromatography using a 40 g of column (silica) and a gradient of 0-2% MeOH in DCM as an eluent to afford tert-butyl (2-oxo-2,3,4,5-tetrahydro-1H-benzo[b]azepin-3-yl)carbamate as a white solid (5.3 g, 69%, LC/MS 90%). (LC/MS; m/z 277.0 [M+H]$^+$).

Step 2: A solution of tert-butyl (2-oxo-2,3,4,5-tetrahydro-1H-benzo[b]azepin-3-yl)carbamate (2.3 g, 8.3 mmol), 1-iodo-4-(trifluoromethyl)benzene (4.5 g, 16.6 mmol), K$_2$CO$_3$ (2.4 g, 17.43 mmol), CuI (0.315 g, 1.66 mmol) and (±)-trans-1,2-diaminocyclohexane (0.189 g, 1.66 mmol) in 1,4-dioxane (20 mL) was stirred at 90° C. for 16 h (sealed tube). Progress of the reaction was monitored by TLC. TLC mobile phase: 20% EtOAc in pet ether, RF: 0.52, TLC detection: UV. The reaction mixture diluted with H$_2$O (200 mL) and extracted with EtOAc (200 mL). The organic layer was washed with brine (200 mL), dried over anhydrous Na$_2$SO$_4$ and concentrated under reduced pressure. The crude product (3 g, LC/MS 74%) was purified by normal phase flash column chromatography using a 40 g column (silica) and a gradient of 0-6% EtOAc in pet ether as an eluent to afford tert-butyl (2-oxo-1-(4-(trifluoromethyl)phenyl)-2,3,4, 5-tetrahydro-1H-benzo[b]azepin-3-yl)carbamate (Int-1) as an off-white solid (2 g, 63%, LC/MS 99%). (LC/MS; m/z 421.3 [M+H]$^+$).

Step 3: A solution of Int-1 (1.9 g, 4.5 mmol) in THF (10 mL) was treated with BH$_3$·SMe$_2$ (11.2 mL, 22.5 mmol) at 0° C. under a nitrogen atmosphere and stirred at RT for 6 h. Progress of the reaction was monitored by TLC. TLC mobile phase: 20% EtOAc in pet ether, RF: 0.52, TLC detection: UV. The reaction mixture was cooled to 0° C., quenched with 10% aq Na$_2$CO$_3$ (10 mL) and diluted with EtOAc (100 mL) and H$_2$O (100 mL). The organic layer was washed with brine (100 mL), dried over anhydrous Na$_2$SO$_4$ and concentrated under reduced pressure. The crude product (2 g, LC/MS 30%) was purified by normal phase flash column chromatography using a 24 g column (silica) and a gradient of 0-6% EtOAc in pet ether as an eluent to afford tert-butyl (1-(4-(trifluoromethyl)phenyl)-2,3,4,5-tetrahydro-1H-benzo [b]azepin-3-yl)carbamate as a white solid (750 mg, 38%, LC/MS 94%). (LC/MS; m/z 407.1 [M+H]$^+$).

Step 4: A solution of tert-butyl (1-(4-(trifluoromethyl) phenyl)-2,3,4,5-tetrahydro-1H-benzo[b]azepin-3-yl)carbamate (750 mg, 1.84 mmol) in DCM (10 mL) was cooled to 0° C., treated with 4M HCL in 1,4-dioxane (4.6 mL, 18.4 mmol) and stirred at RT for 2 h. Progress of the reaction was monitored by TLC. TLC mobile phase: 5% MeOH in DCM, RF: 0.09, TLC detection: UV. The reaction mixture was concentrated under reduced pressure to afford 1-(4-(trifluoromethyl)phenyl)-2,3,4,5-tetrahydro-1H-benzo[b]azepin-3-amine hydrochloride (Int-2) as an off-white solid (600 mg, 99%, LC/MS 99%). (LC/MS; m/z 307.1 [M+H]$^+$). Int-2 (100 mg) was dissolved in 2M aq NaOH and extracted with 10% MeOH in DCM (2×20 mL). The combined organic layer was dried over anhydrous Na$_2$SO$_4$ and concentrated under reduced pressure to afford 1-(4-(trifluoromethyl)phenyl)-2,3,4,5-tetrahydro-1H-benzo[b]azepin-3-amine (Cpd. No. 001) as a pale yellow solid (24 mg, LC/MS 95%). (LC/MS; m/z 307.1 [M+H]$^+$).

Example 2: Synthesis of 3-amino-1-(4-(trifluoromethyl)phenyl)-1,3,4,5-tetrahydro-2H-benzo[b]azepin-2-one (Cpd. No. 002)

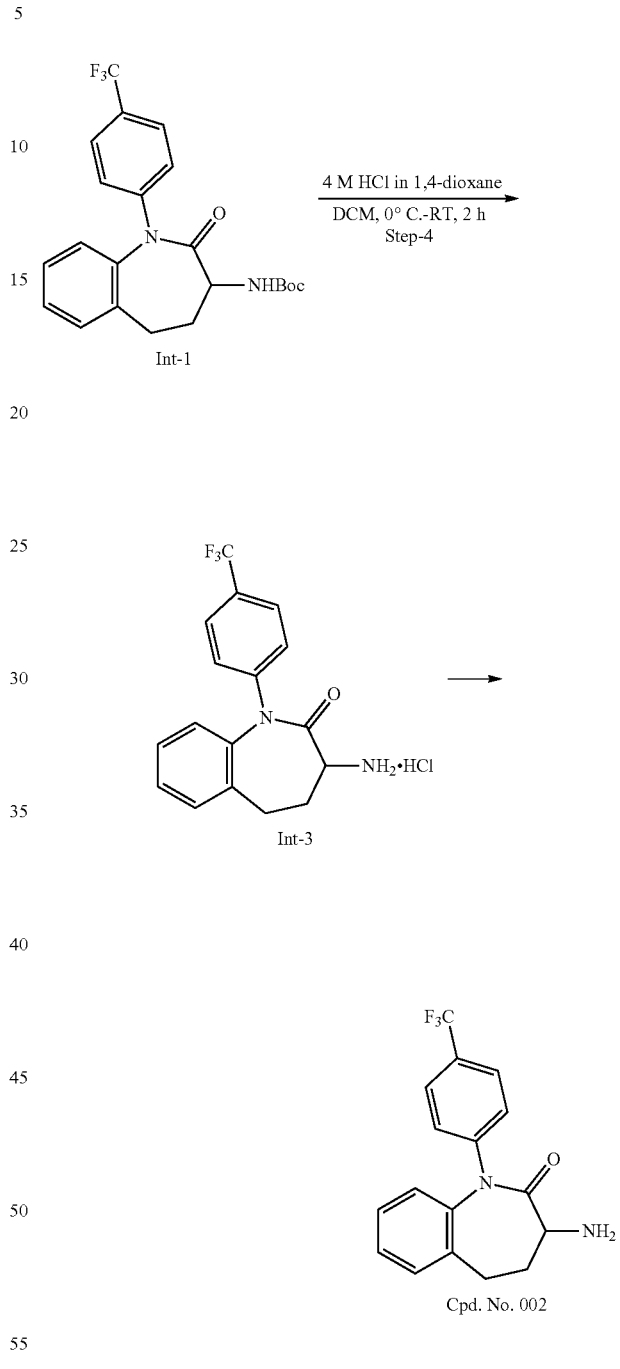

Step 1: This step was executed in a manner similar (use of appropriate reagents and purification methods known to the person skilled in the art) to step 4 towards Cpd. No. 001. Int-1 (850 mg, 2.02 mmol, LC/MS 99%) afforded 3-amino-1-(4-(trifluoromethyl)phenyl)-1,3,4,5-tetrahydro-2H-benzo [b]azepin-2-one hydrochloride (Int-3) (700 mg, 97%, LC/MS 99%). (LC/MS; m/z 321.2 [M+H]$^+$). Int-3 (100 mg) afforded 3-amino-1-(4-(trifluoromethyl)phenyl)-1,3,4,5-tetrahydro-2H-benzo[b]azepin-2-one (Cpd. No. 002) as an off-white solid (14 mg, LC/MS 99%). (LC/MS; m/z 321.2 [M+H]$^+$).

Example 3: Synthesis of 2-((1-(4-(trifluoromethyl)phenyl)-2,3,4,5-tetrahydro-1H-benzo[b]azepin-3-yl)amino)ethan-1-ol (Cpd. No. 003)

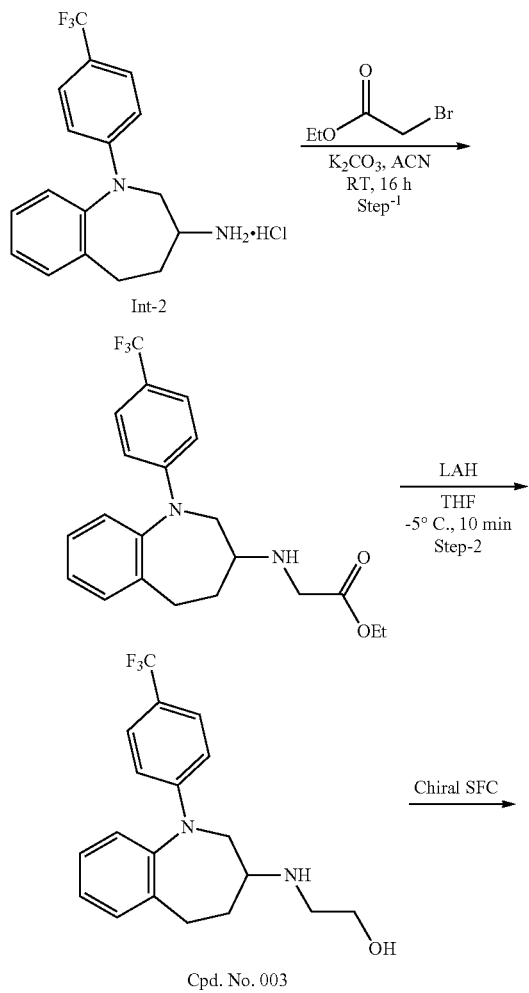

Step 1: A solution of Int-2 (220 mg, 0.64 mmol, LC/MS 99%) and K₂CO₃ (222 mg, 1.60 mmol) in ACN (2 mL) was treated with a solution of ethyl 2-bromoacetate (106 mg, 0.64 mmol) in ACN (1 mL). The reaction mixture was stirred at RT for 16 h. Progress of the reaction was monitored by TLC. TLC mobile phase: 5% MeOH in DCM, RF: 0.56, TLC detection: UV. The reaction mixture was diluted with H₂O (30 mL) and extracted with EtOAc (30 mL). The organic layer was washed with brine (30 mL), dried over anhydrous Na₂SO₄ and concentrated under reduced pressure. The crude product (170 mg, LC/MS 70%) was purified by normal phase flash column chromatography using a 12 g column (silica) and a gradient of 0-2% MeOH in DCM as an eluent to afford ethyl (1-(4-(trifluoromethyl)phenyl)-2,3,4,5-tetrahydro-1H-benzo[b]azepin-3-yl)glycinate as a pale yellow gum (110 mg, 43%, LC/MS 99%). (LC/MS; m/z 393.1 [M+H]⁺).

Step 2: A solution of ethyl (1-(4-(trifluoromethyl)phenyl)-2,3,4,5-tetrahydro-1H-benzo[b]azepin-3-yl)glycinate (100 mg, 0.25 mmol) in THF (2 mL) was cooled to −5° C., treated with LAH (2M in THF) (0.12 mL, 0.25 mmol) and stirred for 10 min under a nitrogen atmosphere. Progress of the reaction was monitored by TLC. TLC mobile phase: 5% MeOH in DCM, RF: 0.33, TLC detection: UV. The reaction mixture was quenched with sat aq NH₄C₁ (1 mL), diluted with H₂O (10 mL) and extracted with EtOAc (10 mL). The organic layer was washed with brine (10 mL), dried over anhydrous Na₂SO₄ and concentrated under reduced pressure. The crude product (65 mg, LC/MS 99%) was purified by preparative HPLC method H2. The collected fractions were lyophilized to afford 2-((1-(4-(trifluoromethyl)phenyl)-2,3,4,5-tetrahydro-1H-benzo[b]azepin-3-yl)amino)ethan-1-ol (Cpd. No. 003) as a pale yellow gum (38 mg, 42%, LC/MS 98%). (LC/MS; m/z 351.1 [M+H]⁺). Chiral SFC purification: 110 mg of Cpd. No. 003 was purified by preparative SFC method K1 to afford Cpd. No. 003-En1 (29 mg) and Cpd. No. 003-En2 (25 mg), both as a pale yellow solid. (LC/MS; m/z 351.1 [M+H]⁺). The chiral purity of both enantiomers was assessed by analytic SFC method S1: Cpd. No. 003-En1, 99.7% ee; Cpd. No. 003, 98.8% ee.

The compound Cpd. No. 004 (from Int-3; employing NaBH₄ in EtOH at step 2) was prepared in a manner similar (use of appropriate reagents and purification methods known to the person skilled in the art) to Cpd. No. 003.

Examples 4-5: Synthesis of 3-((1-(4-(trifluoromethyl)phenyl)-2,3,4,5-tetrahydro-1H-benzo[b]azepin-3-yl)amino)propan-1-ol (Cpd. No. 005) and 3-((1-(4-(trifluoromethyl)phenyl)-2,3,4,5-tetrahydro-1H-benzo[b]azepin-3-yl)amino)propanoic acid (Cpd. No. 006)

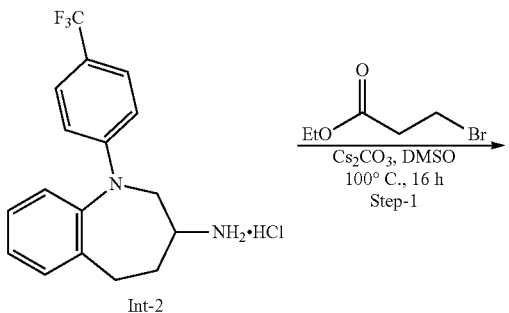

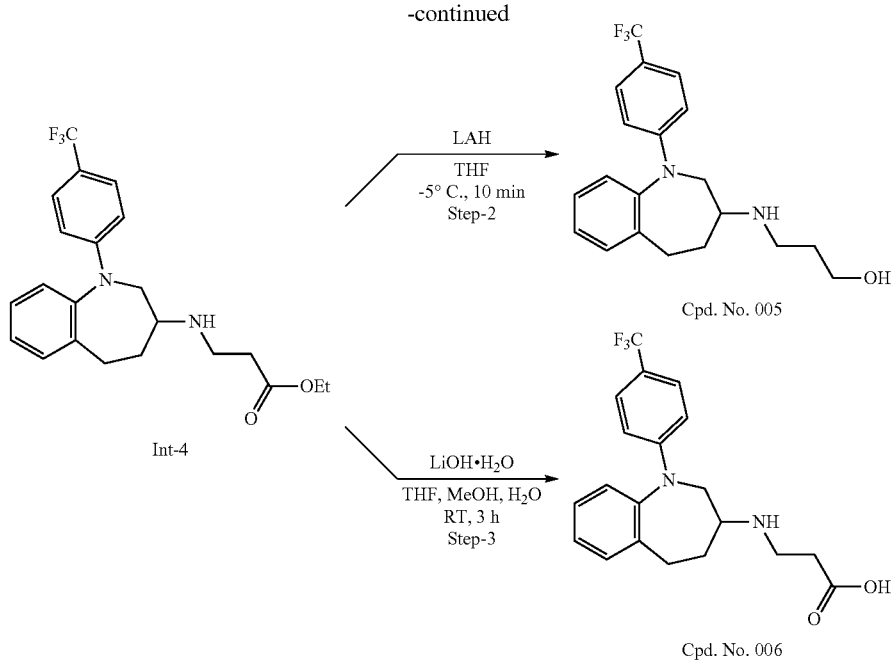

Step 1: This step was executed in a manner similar (use of appropriate reagents and purification methods known to the person skilled in the art) to step 1 towards Cpd. No. 003. Int-2 (120 mg, 0.35 mmol, LC/MS 99%) afforded crude product (120 mg, LC/MS 33%) which was purified by normal phase flash column chromatography using a 12 g column (silica) and a gradient of 0-2% MeOH in DCM as an eluent to afford ethyl 3-((1-(4-(trifluoromethyl)phenyl)-2,3,4,5-tetrahydro-1H-benzo[b]azepin-3-yl)amino)propanoate (Int-4) as a pale brown liquid (40 mg, 24%, LC/MS 85%). (LC/MS; m/z 407.2 [M+H]$^+$).

Step 2: This step was executed in a manner similar (use of appropriate reagents and purification methods known to the person skilled in the art) to step 2 towards Cpd. No. 003. Int-4 (40 mg, 0.098 mmol) afforded crude product (40 mg, LC/MS 73%) which was purified by preparative HPLC method H1 to afford 3-((1-(4-(trifluoromethyl)phenyl)-2,3,4,5-tetrahydro-1H-benzo[b]azepin-3-yl)amino)propan-1-ol (Cpd. No. 005) as a pale yellow gum (11 mg, 34%, LC/MS 94%). (LC/MS; m/z 365.3 [M+H]$^+$).

Step 3: A solution of Int-4 (120 mg, 0.29 mmol) and LiOH·H$_2$O (49 mg, 1.18 mmol) in THF (1 mL), MeOH (1 mL) and H$_2$O (1 mL) was stirred at RT for 3 h. Progress of the reaction was monitored by TLC. TLC mobile phase: 10% MeOH in DCM, RF: 0.01, TLC detection: UV. The reaction mixture was concentrated under reduced pressure, diluted with H$_2$O (10 mL) and acidified with 2M HCl (pH-7). The aq layer was extracted with 10% MeOH in DCM (2×10 mL), dried over Na$_2$SO$_4$ and concentrated under reduced pressure. The crude product (110 mg, LC/MS 77%) was purified by preparative HPLC method H3. The collected fractions were lyophilized to afford 3-((1-(4-(trifluoromethyl)phenyl)-2,3,4,5-tetrahydro-1H-benzo[b]azepin-3-yl)amino)propanoic acid (Cpd. No. 006) as a yellow solid (41 mg, 43%, LC/MS 99%). (LC/MS; m/z 379.3 [M+H]$^+$).

Example 6: Synthesis of 3-((3-hydroxypropyl)amino)-1-(4-(trifluoromethyl)phenyl)-1,3,4,5-tetrahydro-2H-benzo[b]azepin-2-one (Cpd. No. 007)

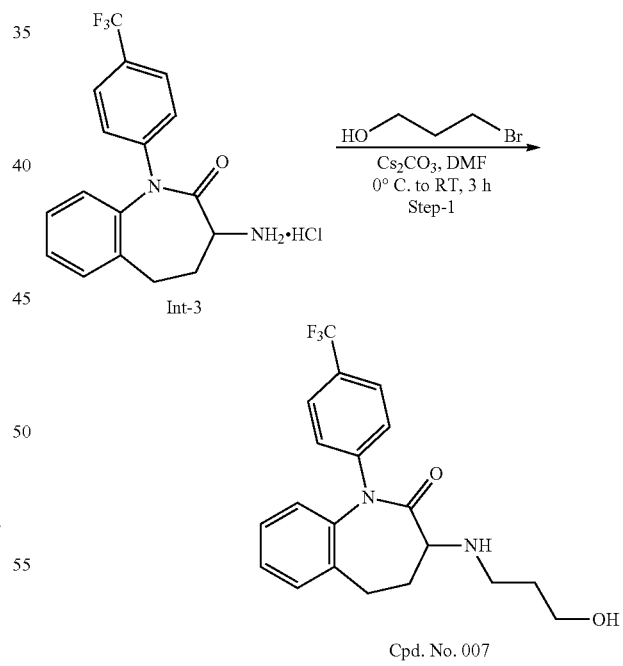

Step 1: A solution of Int-3 (200 mg, 0.56 mmol, LC/MS 99%), Cs$_2$CO$_3$ (365 mg, 1.12 mmol) and 3-bromopropan-1-ol (94 mg, 0.67 mmol) in DMF (2 ml) was stirred at RT for 16 h. Progress of the reaction was monitored by TLC. TLC mobile phase: 10% MeOH in DCM, RF=0.23, TLC detection: UV. The reaction mixture was diluted with H$_2$O (20 mL) and extracted with DCM (50 mL). The organic layer was washed with brine (20 mL), dried over anhydrous Na₂SO₄ and concentrated under reduced pressure. The crude product (310 mg, LC/MS 68%) was purified by preparative HPLC method H2. The collected fractions were lyophilized to afford 3-((3-hydroxypropyl)amino)-1-(4-(trifluoromethyl)phenyl)-1,3,4,5-tetrahydro-2H-benzo[b]azepin-2-one (Cpd. No. 007) as an off-white solid (22 mg, 10%, LC/MS 97%). (LC/MS; m/z 379.5 [M+H]⁺).

Example 7: Synthesis of N-(1-(4-(trifluoromethyl)phenyl)-2,3,4,5-tetrahydro-1H-benzo[b]azepin-3-yl)acrylamide (Cpd. No. 008)

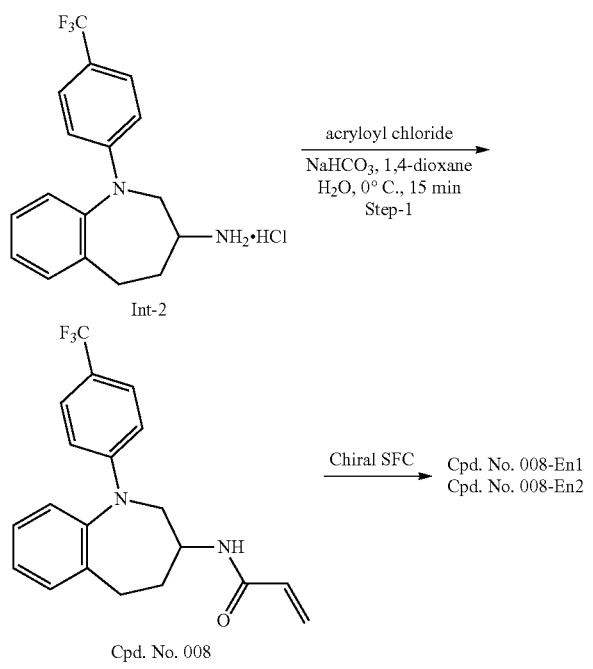

Step 1: A solution of Int-2 (150 mg, 0.43 mmol, LC/MS 99%) and NaHCO₃ (110 mg, 1.31 mmol) in 1,4-dioxane (2 mL) and H₂O (0.2 mL) was cooled to 0° C., treated dropwise with a solution of acryloyl chloride (43 mg, 0.48 mmol) in 1,4-dioxane (1 mL) and stirred at 0° C. for 15 min. Progress of the reaction was monitored by TLC. TLC mobile phase: 5% MeOH in DCM, RF: 0.54, TLC detection: UV. The reaction mixture was diluted H₂O (20 mL) and extracted with EtOAc (20 mL). The organic layer was washed with H₂O (20 mL), dried over anhydrous Na₂SO₄ and concentrated under reduced pressure. The crude product (100 mg, LC/MS 86%) was purified by preparative HPLC method H2. The collected fractions were lyophilized to afford N-(1-(4-(trifluoromethyl)phenyl)-2,3,4,5-tetrahydro-1H-benzo[b]azepin-3-yl)acrylamide (Cpd. No. 008) as an off-white solid (26 mg, 16%, LC/MS 99%). (LC/MS; m/z 361.2 [M+H]⁺). Chiral SFC purification: 110 mg of Cpd. No. 008 was purified by preparative SFC method K₁ to afford Cpd. No. 008-En1 (33 mg) and Cpd. No. 008-En2 (37 mg), both as an off-white solid. (LC/MS; m/z 361.2 [M+H]⁺). The chiral purity of both enantiomers was assessed by analytic SFC method S2: Cpd. No. 008-En1, 99.9% ee; Cpd. No. 008, 99.9% ee.

The following compounds were prepared in a manner similar (use of appropriate reagents and purification methods known to the person skilled in the art) to Cpd. No. 008: Cpd. No. 009 (employing propionyl chloride and TEA in DCM) and Cpd. No. 010 (from Int-3).

Example 8: Synthesis of 7-((2-hydroxyethyl)amino)-1-(4-(trifluoromethyl)phenyl)-1,2,3,4-tetrahydro-5H-benzo[b]azepin-5-one (Cpd. No. 011)

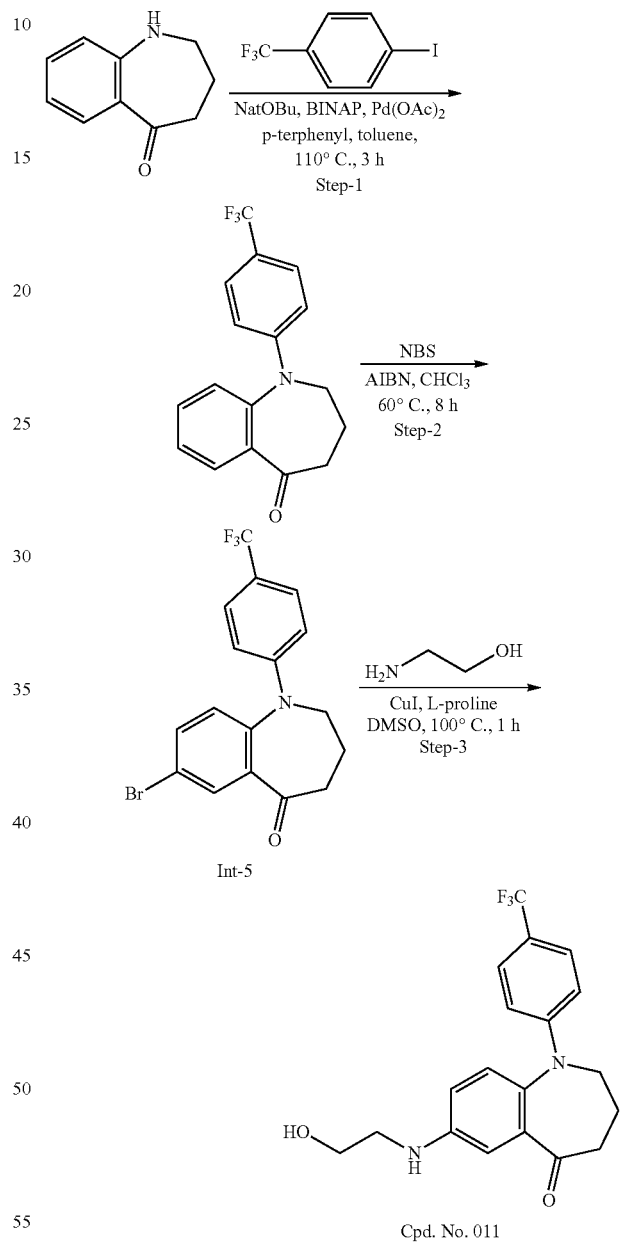

Step 1: A solution of 1,2,3,4-tetrahydro-5H-benzo[b]azepin-5-one (10 g, 62.1 mmol), Pd(OAc)₂ (2.1 g, 3.1 mmol), p-terphenyl (3.3 g, 14.28 mmol) and BINAP (3.87 g, 6.21 mmol) in toluene (80 mL) was stirred at 40° C. for 10 min. To the solution was added 1-iodo-4-(trifluoromethyl)benzene (10.2 g, 37.26 mmol) and NaOtBu (8.35 g, 86.94 mmol) and the reaction mixture was stirred at 110° C. for 3 h. Progress of the reaction was monitored by TLC. TLC mobile phase: 20% EtOAc in pet ether, RF: 0.57, TLC detection: UV. The reaction mixture was diluted with H₂O (100 mL) and extracted with EtOAc (2×100 mL). The combined organic layer was dried over anhydrous Na$_2$SO$_4$ and concentrated under reduced pressure. The crude product was purified by normal phase flash column chromatography using a 48 g column (silica) and a gradient of 0-10% EtOAc in pet ether as an eluent to afford 1-(4-(trifluoromethyl) phenyl)-1,2,3,4-tetrahydro-5H-benzo[b]azepin-5-one (3.4 g, 17%, LC/MS 96%) as a brown solid. (LC/MS; m/z 306.0 [M+H]$^+$).

Step 2: A solution of 1-(4-(trifluoromethyl)phenyl)-1,2,3, 4-tetrahydro-5H-benzo[b]azepin-5-one (1 g, 3.3 mmol), NBS (470 mg, 2.64 mmol) and AIBN (54 mg, 0.33 mmol) in CHCl$_3$ (10 mL) was stirred at 60° C. for 8 h. Progress of the reaction was monitored by TLC. TLC mobile phase: 20% EtOAc in pet ether, RF: 0.63, TLC detection: UV. The reaction mixture was diluted with H$_2$O (20 mL) and extracted with CHCl$_3$ (2×20 mL). The combined organic layer was dried over anhydrous Na$_2$SO$_4$ and concentrated under reduced pressure. The crude product (750 mg) was purified by normal phase flash column chromatography using a 24 g column (silica) and a gradient of 0-10% EtOAc in pet ether as an eluent to afford 7-bromo-1-(4-(trifluoromethyl)phenyl)-1,2,3,4-tetrahydro-5H-benzo[b]azepin-5-one (Int-5) as a pale yellow solid (400 mg, 29%, LC/MS 87%). (LC/MS; m/z 384.2 [M+H]$^+$).

Step 3: A solution of Int-5 (100 mg, 0.26 mmol), 2-aminoethanol (24 mg, 0.39 mmol), CuI (99 mg, 0.52 mmol) and L-proline (120 mg, 1.04 mmol) in DMSO (5 mL) was stirred at 100° C. for 1 h (sealed tube; microwave irradiation). Progress of the reaction was monitored by TLC. TLC mobile phase: 20% EtOAc in pet ether, RF: 0.2, TLC detection: UV. The reaction mixture was diluted with H$_2$O (10 mL) and extracted with EtOAc (2×15 mL). The combined organic layer was dried over anhydrous Na$_2$SO$_4$ and concentrated under reduced pressure. The crude product (100 mg, LC/MS 26%) was purified by preparative HPLC method H1. The collected fractions were lyophilized to afford 7-((2-hydroxyethyl)amino)-1-(4-(trifluoromethyl)phenyl)-1,2,3,4-tetrahydro-5H-benzo[b]azepin-5-one (Cpd. No. 011) as a pale yellow solid (11 mg, 13%, LC/MS 99%). (LC/MS; m/z 365.2 [M+H]$^+$).

The compound Cpd. No. 012 (from Int-5; employing 3-aminopropan-1-ol at step 3) was prepared in a manner similar (use of appropriate reagents and purification methods known to the person skilled in the art) to Cpd. No. 011.

Synthesis of
2-(bromomethyl)-1-fluoro-3-nitrobenzene (R1)

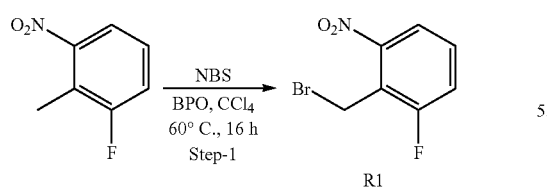

Step 1: A solution of 1-fluoro-2-methyl-3-nitrobenzene (5.0 g, 32.2 mmol), BPO (390 mg, 1.61 mmol) and NBS (5.7 g, 32.2 mmol) in CCl$_4$ (100 mL) was stirred at 60° C. for 16 h. Progress of the reaction was monitored by TLC. TLC mobile phase: 5% EtOAc in pet ether, RF: 0.6, TLC detection: UV. The reaction mixture was cooled to 0° C., filtered and the filter was rinsed with DCM (20 mL). The filtrate was washed with H$_2$O (2×50 mL), brine (50 mL), dried over anhydrous Na$_2$SO$_4$ and concentrated under reduced pressure. The crude product (8.5 g) was purified by normal phase flash column chromatography using silica gel (100-200 mesh) and a gradient of 0-1% EtOAc in pet ether to afford 2-(bromomethyl)-1-fluoro-3-nitrobenzene (R1) as a pale yellow solid (6.0 g, 64%). $^1$H NMR (400 MHz, CDCl3) δ ppm: 7.86 (d, 1H), 7.46-7.54 (m, 1H), 7.38-7.42 (m, 1H), 4.83 (s, 2H). Estimated $^1$H NMR purity: 80%. The product was used as such without further purification.

Synthesis of tert-butyl (2-oxo-1-(4-(trifluoromethyl) phenyl)-1,2,3,4-tetrahydroquinolin-3-yl)carbamate
(Int-6)

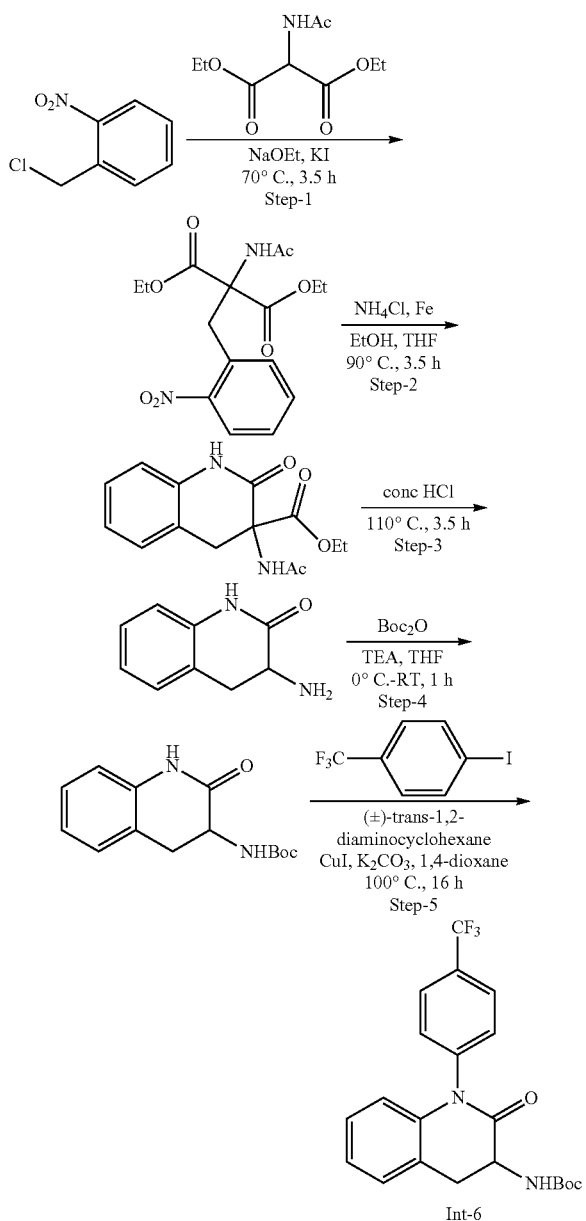

Step 1: Diethyl 2-acetamidomalonate (11.0 g, 50.6 mmol) was treated with a solution of freshly prepared NaOEt (1.2 g of Na metal was dissolved in 50 mL EtOH at 0° C.) and stirred at 50° C. for 1 h. The reaction mixture was treated with 1-(chloromethyl)-2-nitrobenzene (8.6 g, 50.6 mmol) and KI (0.4 g, 2.5 mmol) at 50° C. and stirred at 70° C. for 2.5 h. Progress of the reaction was monitored by TLC. TLC mobile phase: 30% EtOAc in pet ether, RF: 0.2, TLC detection: UV. The reaction mixture was diluted with ice H$_2$O (100 mL) and extracted with EtOAc (3×70 mL). The combined organic layer was dried over anhydrous Na$_2$SO$_4$ and concentrated under reduced pressure. The crude product (13.0 g, LC/MS 79%) was purified by normal phase flash column chromatography using a 80 g column (silica) and a gradient of 0-50% EtOAc in pet ether to afford diethyl 2-acetamido-2-(2-nitrobenzyl)malonate as a pale yellow solid (10 g, 55%, LC/MS 97%). (LC/MS; m/z 352.9 [M+H]$^+$).

Step 2: A solution of diethyl 2-acetamido-2-(2-nitrobenzyl)malonate (10.0 g, 28.4 mmol), sat aq NH$_4$C$_1$ (20 mL) and Fe powder (6.3 g, 113.3 mmol) in EtOH (50 mL) and THF (25 mL) was stirred at 90° C. for 3.5 h. Progress of the reaction was monitored by TLC. TLC mobile phase: 50% EtOAc in pet ether, RF: 0.5, TLC detection: UV. The reaction mixture was filtered through a celite pad and washed with MeOH (100 mL). The filtrate was concentrated under reduced pressure and diluted with EtOAc (100 mL), washed with H$_2$O (2×100 mL), dried over anhydrous Na$_2$SO$_4$ and concentrated under reduced pressure to afford ethyl 3-acetamido-2-oxo-1,2,3,4-tetrahydroquinoline-3-carboxylate as an off-white solid (7.0 g, 86%, LC/MS 97%). (LC/MS; m/z 277.1 [M+H]$^+$).

Step 3: Ethyl 3-acetamido-2-oxo-1,2,3,4-tetrahydroquinoline-3-carboxylate (8 g, 28.98 mmol) was dissolved in conc HCl (40 mL) and stirred at 110° C. for 3.5 h. Progress of the reaction was monitored by TLC. TLC mobile phase: 50% EtOAc in pet ether. The reaction mixture was cooled to RT, diluted with H$_2$O (50 mL) and extracted with 10% MeOH in DCM (2×50 mL). The aq layer was basified with aq NaOH (pH>12) and extracted with 10% MeOH in DCM (3×40 mL). The combined organic layer was washed with brine (100 mL), dried over anhydrous Na$_2$SO$_4$ and concentrated under reduced pressure to afford 3-amino-3,4-dihydroquinolin-2(1H)-one as an off-white solid (1.5 g, 31%, LC/MS 97%). (LC/MS; m/z 163.0 [M+H]$^+$). Along with this compound, 3 g of N-(2-oxo-1,2,3,4-tetrahydroquinolin-3-yl)acetamide was isolated. (LC/MS; m/z 205.1 [M+H]$^+$).

Step 4: A solution of 3-amino-3,4-dihydroquinolin-2(1H)-one (2.0 g, 12.3 mmol) and TEA (3.5 mL, 24.6 mmol) in THF (16 mL) was treated with a solution of Boc$_2$O (2.6 mL, 12.3 mmol) in THF (4 mL). The solution was stirred at RT for 1 h. Progress of the reaction was monitored by TLC. TLC mobile phase: 50% EtOAc in pet ether, RF: 0.53, TLC detection: UV. The reaction mixture was diluted with H$_2$O (20 mL) and extracted with EtOAc (20 mL). The organic layer was dried over anhydrous Na$_2$SO$_4$ and concentrated under reduced pressure. The crude product (1.9 g) was purified by normal phase flash column chromatography using a 40 g column (silica) and a gradient of 0-50% EtOAc in pet ether to afford tert-butyl (2-oxo-1,2,3,4-tetrahydroquinolin-3-yl)carbamate as an off-white solid (1.5 g, 45%, LC/MS 97%). (LC/MS; m/z 263.1 [M+H]$^+$).

Step 5: A solution of tert-butyl (2-oxo-1,2,3,4-tetrahydroquinolin-3-yl)carbamate (2.1 g, 8 mmol), 1-iodo-4-(trifluoromethyl)benzene (4.3 g, 16 mmol), (±)-trans-1,2-diaminocyclohexane (182 mg, 1.62 mmol), CuI (304 mg, 1.6 mmol) and K$_2$CO$_3$ (2.42 g, 17.6 mmol) in 1,4-dioxane (20 mL) was stirred at 100° C. for 16 h (sealed tube). Progress of the reaction was monitored by TLC. TLC mobile phase: 30% EtOAc in pet ether. The reaction mixture was filtered through a celite pad and washed with EtOAc (30 mL). The filtrate was concentrated under reduced pressure. The crude product (2.5 g) was purified by normal phase flash column chromatography using a 40 g column (silica) and a gradient of 0-50% EtOAc in pet ether to afford tert-butyl (2-oxo-1-(4-(trifluoromethyl)phenyl)-1,2,3,4-tetrahydroquinolin-3-yl)carbamate (Int-6) as an off-white solid (1.3 g, 39%, LC/MS 97%). (LC/MS; m/z 407.2 [M+H]$^+$).

Intermediate Int-7 was prepared (employing reagent R1) in a manner similar (use of appropriate reagents and purification methods known to the person skilled in the art) to Int-6:

| Cpd. Nr. | Structure | [M + H]$^+$ (m/z) |
|---|---|---|
| Int-7 | ![structure] | 425.3 |

Structure of Int-7: CF$_3$ group on phenyl attached to N of tetrahydroquinolin-2-one with F substituent; NHBoc at 3-position.

Synthesis of tert-butyl (2-oxo-1-(4-(trifluoromethyl)phenyl)-1,2,3,4-tetrahydro-1,6-naphthyridin-3-yl)carbamate (Int-8)

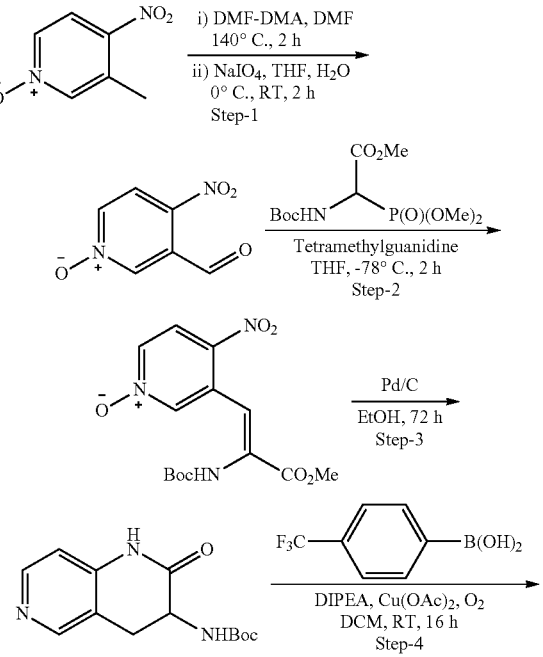

-continued

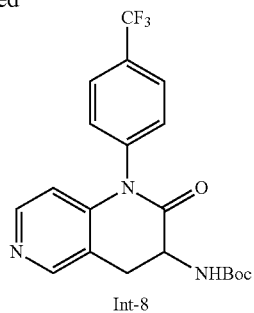

Int-8

Step 1: A solution of 3-methyl-4-nitropyridine 1-oxide (10.0 g, 64.9 mmol) and DMF-DMA (12.5 g, 105.1 mmol) in DMF (35 mL) was stirred at 140° C. for 2 h. The reaction mixture was concentrated under reduced pressure to afford and the residue which was dissolved in THF (50 mL). The solution was added to a stirred solution of NaIO₄ (41.6 g, 194.7 mmol) in THF (300 mL) and H₂O (350 mL) at 0° C. The reaction mixture was stirred at RT for 2 h. Progress of the reaction was monitored by TLC. TLC mobile phase: 5% MeOH in DCM, RF: 0.32, TLC detection: UV. The reaction mixture was diluted with H₂O (500 mL) and extracted with EtOAc (2×150 mL). The combined organic layer was washed with H₂O (2×200 mL), dried over anhydrous Na₂SO₄ and concentrated under reduced pressure. The crude product (10.0 g) was used as such without further purification.

Step 2: A solution of methyl 2-((tert-butoxycarbonyl) amino)-2-(dimethoxyphosphoryl)acetate (17.67 g, 59.5 mmol) in THF (80 mL) was cooled to −78° C., treated with a solution of tetramethylguanidine (7.18 g, 62.47 mmol) in THF (10 mL) and stirred for 30 min. A solution of 3-formyl-4-nitropyridine 1-oxide (10 g, 59.5 mmol) in THF (10 mL) was added at −78° C. The reaction mixture was allowed to slowly warm up and was stirred at RT for 16 h. Progress of the reaction was monitored by TLC. TLC mobile phase: 70% EtOAc in pet ether, RF: 0.29, TLC detection: UV. The reaction mixture was diluted with H₂O (200 mL) and extracted with EtOAc (2×200 mL). The combined organic layer was washed with brine (200 mL), dried over anhydrous Na₂SO₄ and concentrated under reduced pressure. The crude product (14 g, LC/MS 85%) was purified by reverse phase flash column chromatography using a 80 g column (C₁₈) and a gradient of 0-70% ACN in H₂O as an eluent to afford (Z)-3-(2-((tert-butoxycarbonyl)amino)-3-methoxy-3-oxo-prop-1-en-1-yl)-4-nitropyridine 1-oxide as a yellow solid (3.2 g, 13% over 2 steps, LC/MS 89%). (LC/MS; m/z 340.2 [M+H]⁺).

Step 3: A solution of (Z)-3-(2-((tert-butoxycarbonyl) amino)-3-methoxy-3-oxoprop-1-en-1-yl)-4-nitropyridine 1-oxide (3.20 g, 9.40 mmol) and 10% Pd/C (960 mg) in EtOH (35 mL) was stirred under a hydrogen atmosphere (30 psi) at RT for 72 h. Progress of the reaction was monitored by TLC. TLC mobile phase: 10% MeOH in DCM, RF: 0.34, TLC detection: UV. The reaction mixture was filtered through a celite pad, washed with MeOH (50 mL) and the filtrate was concentrated under reduced pressure. The crude product (2.8 g) was purified by normal phase column chromatography using neutral alumina and a gradient of 3% MeOH in DCM as an eluent to afford tert-butyl (2-oxo-1,2,3,4-tetrahydro-1,6-naphthyridin-3-yl)carbamate as an off-white solid (450 mg, 19%, LC/MS 93%). (LC/MS; m/z 264.2 [M+H]⁺).

Step 4: A solution of tert-butyl (2-oxo-1,2,3,4-tetrahydro-1,6-naphthyridin-3-yl)carbamate (450 mg, 1.71 mmol), (4-(trifluoromethyl)phenyl)boronic acid (1.30 g, 6.84 mmol), Cu(OAc)₂ (778 mg, 4.27 mmol) and DIPEA (1.32 g, 10.26 mmol) in DCM (10 mL) was stirred under an oxygen atmosphere at RT for 16 h. Progress of the reaction was monitored by TLC. TLC mobile phase: 10% MeOH in DCM, RF: 0.47, TLC detection: UV. The reaction mixture was filtered through a celite pad and, washed with DCM (500 mL) and the filtrate was concentrated under reduced pressure. The crude product (1.0 g, LC/MS 16%) was purified by normal phase flash column chromatography using a 24 g column (silica) and a gradient of 04% MeOH in DCM as an eluent to afford tert-butyl (2-oxo-1-(4-(trifluoromethyl)phenyl)-1,2,3,4-tetrahydro-1,6-naphthyridin-3-yl)carbamate (Int-8) as a pale brown gum (180 mg, 27%, LC/MS 99%). (LC/MS; m/z 408.3 [M+H]⁺).

Example 9: Synthesis of N-(2-oxo-1-(4-(trifluoromethyl)phenyl)-1,2,3,4-tetrahydroquinolin-3-yl)acrylamide (Cpd. No. 013)

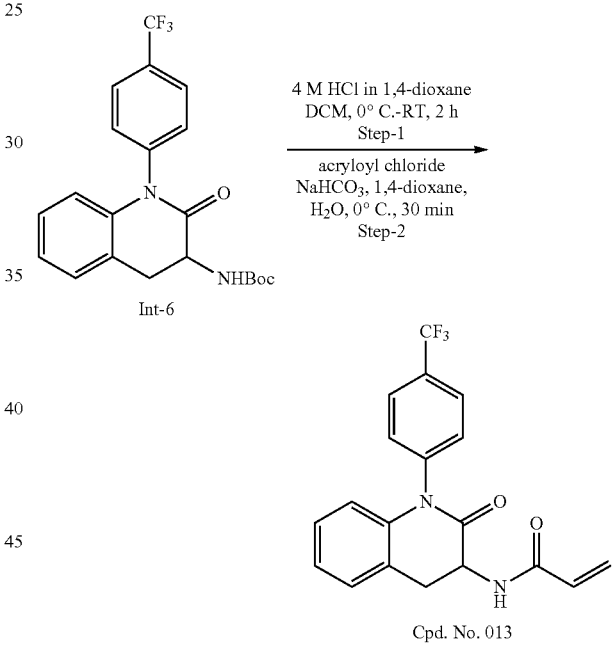

Step 1: A solution of Int-6 (250 mg, 0.615 mmol, LC/MS 97%) in DCM (6 mL) was cooled to 0° C., treated with 4 M HCl in 1,4-dioxane (1.5 mL, 1.23 mmol) and stirred at RT for 2 h. Progress of the reaction was monitored by TLC. TLC mobile phase: 30% EtOAc in pet ether, RF: 0.1, TLC detection: UV. The reaction mixture was concentrated under reduced pressure to afford 3-amino-1-(4-(trifluoromethyl) phenyl)-3,4-dihydroquinolin-2(1H)-one hydrochloride as an off-white solid (200 mg, 96%, LC/MS 98%). (LC/MS; m/z 307.3 [M+H]⁺). The product was used a such without further purification.

Step 2: A solution of 3-amino-1-(4-(trifluoromethyl)phenyl)-3,4-dihydroquinolin-2(1H)-one hydrochloride (200 mg, 0.584 mmol) in 1,4-dioxane (8 mL) and H₂O (2 mL) was cooled to 0° C. and treated with NaHCO₃ (147 mg, 1.75 mmol) and a solution of acryloyl chloride (63 mg, 0.700 mmol) in 1,4-dioxane (1 mL). The reaction mixture was stirred at 0° C. for 30 min. Progress of the reaction was monitored by TLC. TLC mobile phase: 30% EtOAc in pet ether, RF: 0.4, TLC detection: UV. The reaction mixture was diluted with $H_2O$ (20 mL) and extracted with EtOAc (2×20 mL). The combined organic layer was washed with $H_2O$ (20 mL), brine (20 mL), dried over anhydrous $Na_2SO_4$ and concentrated under reduced pressure. The crude product (250 mg, LC/MS 63%) was purified by preparative HPLC method H2. The collected fractions were lyophilized to afford N-(2-oxo-1-(4-(trifluoromethyl) phenyl)-1,2,3,4-tetrahydroquinolin-3-yl)acrylamide (Cpd. No. 013) as an off-white solid (70 mg, 33%, LC/MS 99%). (LC/MS; m/z 361.2 [M+H]$^+$).

The following compounds were prepared in a manner similar (use of appropriate reagents and purification methods known to the person skilled in the art) to Cpd. No. 013: Cpd. No. 014 (from Int-7) and Cpd. No. 015 (from Int-8).

TABLE 2

Analytical data for synthesized compounds of the invention

| Cpd. No. | [M + H]$^+$ (m/z): | LC/MS Method | RT (min.) | $^1$H NMR (δ ppm) |
|---|---|---|---|---|
| 001 | 307.2 | L1 | 2.36 | (DMSO-d$_6$) δ ppm: 7.39-7.45 (m, 3H), 7.26-7.36 (m, 2H), 7.16-7.22 (m, 1H), 6.65-6.72 (m, 2H), 4.12-4.20 (m, 1H), 2.97-3.06 (m, 1H), 2.69-2.80 (m, 1H), 2.62-2.68 (m, 1H), 2.35-2.44 (m, 1H), 1.94-2.04 (m, 1H), 1.62-1.88 (m, 2H), 1.12-1.21 (m, 1H). |
| 002 | 321.2 | L1 | 2.17 | (CDCl$_3$) δ ppm: 7.75-7.77 (d, 2H), 7.63-7.41 (m, 3H), 7.23-7.26 (m, 2H), 6.83-6.86 (m, 1H), 2.78-2.91 (m, 1H), 2.73-2.74 (m, 1H), 2.23-2.28 (m, 1H), 1.80-1.89 (m, 3H). |
| 003 | 351.1 | L1 | 2.33 | (DMSO-d$_6$) δ ppm: 7.39-7.46 (m, 3H), 7.26-7.35 (m, 2H), 7.16-7.21 (m, 1H), 6.63-6.70 (m, 2H), 4.50-4.58 (m, 1H), 4.26-4.34 (m, 1H), 3.43-3.51 (m, 2H), 2.65-2.93 (m, 5H), 2.33-2.46 (m, 1H), 2.04-2.15 (m, 1H), 1.14-1.26 (m, 1H). |
| 003-En1 | 351.1 | S1 | 2.59 | (DMSO-d$_6$) δ ppm: 7.39-7.45 (m, 3H), 7.24-7.35 (m, 2H), 7.17-7.20 (m, 1H), 6.64-6.69 (m, 2H), 4.46-4.52 (m, 1H), 4.22-4.32 (m, 1H), 3.42-3.48 (m, 2H), 2.67-2.88 (m, 5H), 2.36-2.46 (m, 1H), 2.05-2.14 (m, 1H), 1.63-1.78 (m, 1H), 1.13-1.24 (m, 1H). |
| 003-En2 | 351.1 | S1 | 5.04 | (DMSO-d$_6$) δ ppm: 7.38-7.46 (m, 3H), 7.24-7.34 (m, 2H), 7.16-7.21 (m, 1H), 6.63-6.69 (m, 2H), 4.47-4.52 (m, 1H), 4.24-4.33 (m, 1H), 3.42-3.50 (m, 2H), 2.66-2.86 (m, 5H), 2.35-2.45 (m, 1H), 2.03-2.10 (m, 1H), 1.69-1.83 (m, 1H), 1.13-1.25 (m, 1H). |
| 004 | 365.2 | L1 | 2.17 | (DMSO-d$_6$) δ ppm: 7.75-7.77 (d, 2H), 7.35-7.41 (m, 3H), 7.23-7.28 (m, 2H), 6.85-6.89 (m, 1H), 4.41-4.44 (t, 1H), 3.80-3.39 (m, 2H), 3.23-3.37 (m, 1H), 2.84-2.87 (m, 1H), 2.67-2.82 (m, 2H), 2.38-2.49 (m, 3H), 1.81-1.84 (m, 1H). |
| 005 | 365.3 | L2 | 4.38 | (DMSO-d$_6$) δ ppm: 7.40-7.48 (m, 3H), 7.26-7.37 (m, 2H), 7.17-7.21 (m, 1H), 6.61-6.69 (m, 2H), 4.39-4.51 (br s, 1H), 4.21-4.30 (m, 1H), 3.44-3.52 (m, 2H), 2.66-2.84 (m, 5H), 2.32-2.45 (m, 1H), 2.04-2.12 (m, 1H), 1.61-1.74 (m, 1H), 1.51-1.59 (m, 2H), 1.13-1.24 (m, 1H). |
| 006 | 379.3 | L1 | 2.38 | (DMSO-d$_6$) δ ppm: 7.38-7.48 (m, 3H), 7.25-7.37 (m, 2H), 7.16-7.22 (m, 1H), 6.61-6.70 (m, 2H), 4.24-4.33 (m, 1H), 2.81-2.97 (m, 4H), 2.64-2.74 (m, 1H), 2.37-2.46 (m, 1H), 2.27-2.36 (m, 2H), 2.06-2.16 (m, 1H), 1.16-1.28 (m, 1H). |
| 007 | 379.5 | L3 | 6.98 | (DMSO-d$_6$) δ ppm: 7.75-7.77 (d, 2H), 7.41-7.43 (m, 1H), 7.36-7.38 (d, 2H), 7.26-7.30 (m, 2H), 6.87-6.89 (m, 1H), 3.40-3.44 (t, 2H), 3.16-3.21 (dd, 1H), 2.81-2.87 (m, 2H), 2.62-2.79 (m, 1H), 2.29-2.35 (m, 2H), 1.84-1.88 (m, 1H), 1.49-1.55 (m, 1H). |
| 008 | 361.2 | L1 | 3.16 | (DMSO-d$_6$) δ ppm: 8.14-8.20 (d, 1H), 7.41-7.51 (m, 3H), 7.29-7.38 (m, 2H), 7.21-7.26 (m, 1H), 6.79-6.88 (m, 2H), 6.14-6.27 (m, 2H), 5.61-5.68 (m, 1H), 4.21-4.32 (m, 1H), 4.06-4.15 (m, 1H), 2.81-2.97 (br s, 1H), 2.70-2.79 (m, 1H), 2.42-2.49 (m, 1H), 1.97-2.09 (m, 1H), 1.39-1.51 (m, 1H). |
| 008-En1 | 361.2 | S2 | 1.68 | (DMSO-d$_6$) δ ppm: 8.13-8.19 (d, 1H), 7.43-7.49 (m, 3H), 7.29-7.38 (m, 2H), 7.21-7.25 (m, 1H), 6.79-6.88 (m, 2H), 6.14-6.28 (m, 2H), 5.62-5.66 (m, 1H), 4.20-4.32 (m, 1H), 4.07-4.16 (m, 1H), 2.81-2.97 (br s, 1H), 2.70-2.79 (m, 1H), 2.42-2.48 (m, 1H), 1.97-2.06 (m, 1H), 1.39-1.51 (m, 1H). |
| 008-En2 | 361.2 | S2 | 2.38 | (DMSO-d$_6$) δ ppm: 8.13-8.19 (d, 1H), 7.42-7.48 (m, 3H), 7.28-7.38 (m, 2H), 7.20-7.25 (m, 1H), 6.79-6.88 (m, 2H), 6.13-6.29 (m, 2H), 5.62-5.67 (m, 1H), 4.20-4.32 (m, 1H), 4.07-4.17 (m, 1H), 2.81-2.98 (br, s, 1H), 2.70-2.79 (m, 1H), 2.42-2.49 (m, 1H), 1.98-2.07 (m, 1H), 1.39-1.52 (m, 1H). |
| 009 | 363.3 | L1 | 3.13 | (DMSO-d$_6$) δ ppm: 7.76-7.84 (m, 1H), 7.41-7.49 (m, 3H), 7.28-7.39 (m, 2H), 7.19-7.25 (m, 1H), 6.75-6.85 (m, 2H), 4.11-4.27 (m, 1H), 3.96-4.08 (m, 1H), 2.65-2.92 (m, 2H), 2.40-2.48 (m, 1H), 2.06-2.15 (q, 2H), 1.91-2.01 (m, 1H), 1.34-1.49 (m, 1H), 0.98-1.06 (t, 3H). |

TABLE 2-continued

Analytical data for synthesized compounds of the invention

| Cpd. No. | [M + H]+ (m/z): | LC/MS Method | RT (min.) | $^1$H NMR (δ ppm) |
|---|---|---|---|---|
| 010 | 375.2 | L1 | 2.80 | (DMSO-$d_6$) δ ppm: 8.55-8.57 (d, 1H), 7.76-7.78 (d, 2H), 7.43-7.46 (m, 1H), 7.32-7.36 (d, 2H), 7.29-7.31 (m, 2H), 6.89-6.92 (m, 1H), 6.29-6.37 (q, 1H), 6.06-6.11 (dd, 1H), 5.61-5.64 (dd, 1H), 4.40-4.47 (m, 1H), 3.94-2.32 (m, 1H), 2.84-2.89 (m, 1H), 2.35-2.69 (m, 1H), 2.16-2.25 (m, 1H). |
| 011 | 365.2 | L1 | 2.83 | (DMSO-$d_6$) δ ppm: 7.44-7.47 (d, 2H), 6.99-7.02 (d, 1H), 6.89-6.91 (q, 3H), 6.83-6.86 (dd, 1H), 5.92-5.95 (t, 1H), 4.69-4.72 (t, 1H), 3.74-3.77 (t, 2H), 3.53-3.58 (q, 2H), 3.1-3.14 (q, 2H), 2.43-2.51 (m, 2H), 2.04-2.08 (m, 2H). |
| 012 | 379.3 | L1 | 2.85 | (DMSO-$d_6$) δ ppm: 8.41 (s, 1H), 7.44-7.46 (d, 2H), 6.99-7.02 (d, 1H), 6.88-6.91 (m, 3H), 6.79-6.82 (dd, 1H), 5.92-5.95 (t, 1H), 4.48-4.5 (t, 1H), 3.74-3.77 (t, 2H), 3.49-3.53 (m, 2H), 3.05-3.1 (q, 2H), 2.49-2.5 (m, 2H), 2.01-2.07 (m, 2H), 1.68-1.73 (m, 2H), 1.37 (s, 1H), 0.94-0.96 (d, 1H). |
| 013 | 361.2 | L1 | 2.64 | (CDCl$_3$) δ ppm: 7.78-7.80 (d, 2H), 7.38-7.40 (d, 2H), 7.30-3.1 (m, 1H), 7.07-7.13 (m, 1H), 6.73-6.75 (d, 1H), 6.33-6.42 (m, 2H), 6.18-6.25 (m, 1H), 5.70-5.73 (dd, 1H), 4.76-4.82 (m, 1H), 3.67-3.73 (m, 1H), 2.94-3.01 (m 1H). |
| 014 | 379.2 | L1 | 2.82 | (CDCl$_3$) δ ppm: 7.79 (d, 2H), 7.38 (d, 2H), 7.05-7.10 (m, 1H), 6.86 (t, 1H), 6.71 (d, 1H), 6.36 (dd, 1H), 6.19-6.25 (m, 2H), 5.73 (dd, 1H), 4.79-4.84 (m, 1H), 3.97-4.02 (m, 1H), 2.67-2.75 (m, 1H). |
| 015 | 362.2 | L1 | 1.94 | (CDCl$_3$) δ ppm: 8.51 (s, 1H), 8.33 (d, 1H), 7.83 (d, 2H), 7.38 (d, 2H), 6.66 (d, 1H), 6.19-6.40 (m, 3H), 5.75 (dd, 1H), 4.83-4.88 (m, 1H), 3.77-3.83 (m, 1H), 2.93-3.01 (m, 1H). |

Part B: Experimental Biology Procedures

Example 10: Activity of Compounds of the Disclosure in a Reporter Gene Assay for Measuring the Inhibition of YAP/TAZ-TEAD Transcription Hek293T cells are cultured in DMEM supplemented with 10% fetal bovine serum, Sodium pyruvate, Sodium bicarbonate, L-glutamine. The cells are harvested and transiently transfected with TEAD-responsive element luciferase reporter. Transfected cells are plated in 384-wells plate containing pre-diluted compounds. After 24 hours incubation at 37° C./5% CO$_2$, assay plates were cooled down to RT and levelled to an equal volume per well, prior to the addition of 25 uL luciferase substrate SteadyLite (Perkin Elmer)/well. The plate was shaken for 10 min at 600 rpm, centrifuged for 1 min at 500 rpm and measured with an Envision reader (PerkinElmer). The amount of relative light units produced by the TEAD reporter is used to calculated percent of inhibition.

The percent of reporter inhibition was calculated in the presence of a positive control inhibitor (100% inhibition) versus a condition with the presence of the vehicle basal activity of the reporter (0% inhibition). The ability of a test compound to inhibit this activity was determined as:

Percentage inhibition=[1-((RLU determined in the presence of vehicle−RLU determined for sample with test compound present) divided by (RLU determined in the presence of vehicle−RLU determined for sample with positive control inhibitor))]*100

The activities of example compounds tested are depicted in Table 3. The activity ranges A, B and C refer to IC$_{50}$ values in the reporter gene assay as follows: "A": IC$_{50}$<1 μM; "B": 1 μM≤IC$_{50}$≤20 μM and "C": IC$_{50}$>20 μM; NT=not tested.

TABLE 3

Activities of compounds of the disclosure in the gene reporter assay for measuring YAP/TAZ-TEAD transcription activity

| Cpd. No. | IC$_{50}$ |
|---|---|
| 001 | B |
| 002 | C |
| 003 | B |
| 003-En1 | B |
| 003-En2 | B |
| 004 | B |
| 005 | B |
| 006 | C |
| 007 | C |
| 008 | B |
| 008-En1 | A |
| 008-En2 | A |
| 009 | B |
| 010 | C |
| 011 | B |
| 012 | C |
| 013 | A |
| 014 | A |
| 015 | B |

Example 11: Activity of Compounds of the Disclosure in Mesothelioma Cell Line Proliferation Assays Mesothelioma cell lines, NCI-H226 and NCI-H2052 (all sourced from the ATCC cell culture collection) are plated in 96-well plates (Corning® 96 Well White Polystyrene Microplate clear flat bottom, white polystyrene (TC-Treated)), at 1500 cells/well in full medium (RPMI 1640 ATCC modification with L-glutamine, HEPES, Phenol Red, Sodium Pyruvate, High glucose, Low sodium bicarbonate and 10% fetal bovine serum). Cells are incubated overnight at 37° C. in an incubator with 5% CO$_2$. Then compounds, dissolved in DMSO, are added in dose-response. Cells are incubated with compound dilutions for another 6 days at 37° C. in an incubator with 5% $CO_2$. Cell viability is quantitated using the ATPlite kit (Perkin-Elmer) and the luminescence is read-out using an Envision instrument (Perkin-Elmer). The amount of relative light units produced using the ATPlite kit is used to calculated percent of inhibition.

The activities of some example compounds are depicted in Table 4. The activity ranges A, B and C refer to EC50 values in the mesothelioma cell line proliferation assay as described as follows: "A": $EC_{50}$<1 µM; "B": 1 µM≤$EC_{50}$≤10 µM and "C": $EC_{50}$>10 µM; NT: not tested.

TABLE 4

Activities of a selection of compounds in the mesothelioma cell line proliferation assay

| Cpd. No. | $EC_{50}$ | |
|---|---|---|
| | H226 | H2052 |
| 003 | C | C |
| 008 | A | A |
| 013 | A | A |
| 014 | A | A |

The invention claimed is:

1. A compound of Formula I:

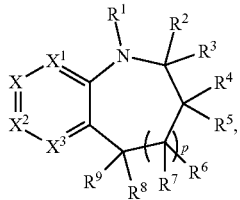

I or a stereoisomer, tautomer, pharmaceutically acceptable salt, or solvate thereof, wherein:

p is 0, 1, or 2;

$R^1$ is selected from the group consisting of:
  (i) unsubstituted or substituted $C_1$-$C_6$ alkyl, wherein one or more substituents are independently selected from the group consisting of:
    (a) substituted $C_6$-$C_{10}$ aryl, wherein one or more substituents are independently selected from the group consisting of:
      (1) halogen,
      (2) cyano,
      (3) $C_1$-$C_6$ alkyl,
      (4) $C_3$-$C_6$ cycloalkyl,
      (5) —$OZ^1$,
      (6) $C_2$-$C_6$ alkenyl, and
      (7) $C_2$-$C_6$ alkynyl,
    (b) unsubstituted or substituted $C_3$-$C_6$ cycloalkyl, wherein one or more substituents are independently selected from the group consisting of:
      (1) halogen,
      (2) cyano,
      (3) $C_1$-$C_6$ alkyl,
      (4) $C_3$-$C_6$ cycloalkyl,
      (5) $C_1$-$C_6$ haloalkyl, and
      (6) —$OZ^1$,
    (c) $C_2$-$C_6$ alkynyl,
  (ii) unsubstituted or substituted $C_6$-$C_{10}$ aryl, wherein one or more substituents are independently selected from the group consisting of:
    (a) halogen,
    (b) cyano,
    (c) $C_1$-$C_6$ alkyl,
    (d) $C_3$-$C_6$ cycloalkyl,
    (e) $C_1$-$C_6$ haloalkyl,
    (f) —$OZ^1$, and
    (g) unsubstituted or substituted $C_6$-$C_{10}$ aryl, wherein one or more substituents are independently selected from the group consisting of halogen, $C_1$-$C_6$ alkyl, and $C_1$-$C_6$ haloalkyl, and —$OZ^1$,
  (iii) unsubstituted or substituted 5- to 9-membered heteroaryl, wherein one or more substituents are independently selected from the group consisting of:
    (a) halogen,
    (b) cyano,
    (c) $C_1$-$C_6$ alkyl,
    (d) $C_3$-$C_6$ cycloalkyl,
    (e) $C_1$-$C_6$ haloalkyl,
    (f) —$OZ^1$, and
    (g) unsubstituted or substituted $C_6$-$C_{10}$ aryl, wherein one or more substituents are independently selected from the group consisting of halogen, $C_1$-$C_6$ alkyl, and $C_1$-$C_6$ haloalkyl, and —$OZ^1$,
  (iv) unsubstituted or substituted $C_3$-$C_6$ cycloalkyl, wherein one or more substituents are independently selected from the group consisting of:
    (a) halogen,
    (b) cyano,
    (c) $C_1$-$C_6$ alkyl,
    (d) $C_3$-$C_6$ cycloalkyl,
    (e) $C_1$-$C_6$ haloalkyl, and
    (f) —$OZ^1$,
  (v) unsubstituted or substituted $C_3$-$C_6$ heterocycle, wherein one or more substituents are independently selected from the group consisting of:
    (a) halogen,
    (b) cyano,
    (c) $C_1$-$C_6$ alkyl,
    (d) $C_3$-$C_6$ cycloalkyl,
    (e) $C_1$-$C_6$ haloalkyl, and
    (f) —$OZ^1$,
  (vi) —S(=O)$_2$$Z^2$, and
  (vii) —C(=O)$Z^2$;

$R^2$ and $R^3$ are independently selected from the group consisting of hydrogen and $C_1$-$C_6$ alkyl; or $R^2$ and $R^3$ taken together with the carbon atom to which they are attached form a —C(=O)— group;

$R^4$ is selected from the group consisting of hydrogen and —$NR^{10a}R^{10b}$;

$R^5$ is selected from the group consisting of hydrogen and $C_1$-$C_6$ alkyl;

each $R^6$ and $R^7$ is independently selected from the group consisting of hydrogen and $C_1$-$C_6$ alkyl;

$R^8$ and $R^9$ are independently selected from the group consisting of hydrogen and $C_1$-$C_6$ alkyl; or $R^8$ and $R^9$ taken together with the carbon atom to which they are attached form a —C(=O)— group;

$R^{10a}$ is selected from the group consisting of:
  (i) —C(=O)$Z^2$
  (ii) —C(=O)O$Z^2$,
  (iii) —C(=O)N$Z^3Z^4$,
  (iv) —S(=O)$_2Z^2$, (v) —S(=O)$_2$NZ$^3$Z$^4$,
(vi) —S(=O)(=NZ)Z$^2$,
(vii) —S(=NZ$^5$)(=NZ$^6$)Z$^2$,
(viii) —S(=O)(=NZ$^5$)NZ$^3$Z$^4$, and
(ix) unsubstituted or substituted C$_1$-C$_6$ alkyl, wherein one or more substituents are independently selected from the group consisting of:
(a) cyano,
(b) hydroxy,
(c) —OZ$^1$,
(d) —C(=O)OH
(e) —C(=O)Z$^2$
(f) —C(=O)OZ$^2$,
(g) —C(=O)NZ$^3$Z$^4$,
(h) —S(=O)$_2$Z$^2$,
(i) —S(=O)$_2$NZ$^3$Z$^4$,
(j) —S(=O)(=NZ$^5$)Z$^2$,
(k) —S(=NZ$^5$)(=NZ$^6$)Z$^2$,
(l) —S(=O)(=NZ$^5$)NZ$^3$Z$^4$, and
(m) —NZ$^3$Z$^4$,
R$^{10b}$ is selected from the group consisting of hydrogen and C$_1$-C$_6$ alkyl;
each Z$^1$ is independently selected from the group consisting of:
(i) hydrogen,
(ii) C$_1$-C$_6$ alkyl,
(iii) unsubstituted or substituted C$_2$-C$_6$ alkenyl, wherein one or more substituents are independently selected from the group consisting of cyano, —S(=O)$_2$Z$^2$, —S(=O)$_2$NZ$^3$Z$^4$, halogen, —NZ$^3$Z$^4$, and 4- to 8-membered heterocycle,
(iv) C$_2$-C$_6$ alkynyl,
(v) C$_3$-C$_6$ cycloalkyl,
(vi) C$_3$-C$_6$ cycloalkenyl, and
(vii) C$_1$-C$_6$ haloalkyl;
each Z$^2$ is independently selected from the group consisting of:
(i) unsubstituted or substituted C$_1$-C$_6$ alkyl, wherein one or more substituents are independently selected from the group consisting of cyano and C$_2$-C$_6$ alkynyl;
(ii) unsubstituted or substituted C$_2$-C$_6$ alkenyl, wherein one or more substituents are independently selected from the group consisting of cyano, —S(=O)$_2$Z$^2$, —S(=O)$_2$NZ$^3$Z$^4$, halogen, —NZ$^3$Z$^4$, 4- to 8-membered heterocycle,
(iii) C$_2$-C$_6$ alkynyl,
(iv) C$_3$-C$_6$ cycloalkyl,
(v) C$_3$-C$_6$ cycloalkenyl,
(vi) C$_1$-C$_6$ haloalkyl,
(vii) unsubstituted or substituted C$_6$-C$_{10}$ aryl, wherein one or more substituents are independently selected from the group consisting of halogen, C$_1$-C$_6$ alkyl, and C$_1$-C$_6$ haloalkyl, and —OZ$^1$, and
(viii) unsubstituted or substituted C$_3$-C$_6$ cycloalkyl, wherein one or more substituents are independently selected from the group consisting of halogen, C$_1$-C$_6$ alkyl, and C$_1$-C$_6$ haloalkyl, and —OZ$^1$;
each Z$^3$ and Z$^4$ are independently selected from the group consisting of:
(i) hydrogen;
(ii) unsubstituted or substituted C$_1$-C$_6$ alkyl, wherein one or more substituents are independently selected from the group consisting of:
(a) unsubstituted or substituted C$_6$-C$_{10}$ aryl, wherein one or more substituents are independently selected from the group consisting of:
(1) halogen,
(2) cyano,
(3) C$_1$-C$_6$ alkyl,
(4) C$_3$-C$_6$ cycloalkyl,
(5) C$_1$-C$_6$ haloalkyl,
(6) —OZ$^1$,
(7) C$_2$-C$_6$ alkenyl, and
(8) C$_2$-C$_6$ alkynyl,
(b) unsubstituted or substituted C$_3$-C$_6$ cycloalkyl, wherein one or more substituents are independently selected from the group consisting of:
(1) halogen,
(2) cyano,
(3) C$_1$-C$_6$ alkyl,
(4) C$_3$-C$_6$ cycloalkyl,
(5) C$_1$-C$_6$ haloalkyl, and
(6) —OZ$^1$,
(c) unsubstituted or substituted 5- to 9-membered heteroaryl, wherein one or more substituents are independently selected from the group consisting of:
(1) halogen,
(2) cyano,
(3) C$_1$-C$_6$ alkyl,
(4) C$_3$-C$_6$ cycloalkyl,
(5) C$_1$-C$_6$ haloalkyl,
(6) —OZ$^1$,
(7) C$_2$-C$_6$ alkenyl, and
(8) C$_2$-C$_6$ alkynyl,
(d) cyano,
(e) hydroxy,
(f) —OZ$^1$, and
(g) —NZ$^3$Z$^4$,
(iii) unsubstituted or substituted C$_2$-C$_6$ alkenyl, wherein one or more substituents are independently selected from the group consisting of cyano, —S(=O)$_2$Z$^2$, —S(=O)$_2$NZ$^3$Z$^4$, halogen, —NZ$^3$Z$^4$, 4- to 8-membered heterocycle,
(iv) C$_2$-C$_6$ alkynyl,
(v) C$_3$-C$_6$ cycloalkyl,
(vi) C$_3$-C$_6$ cycloalkenyl, and
(vii) C$_1$-C$_6$ haloalkyl;
each Z$^5$ and Z$^6$ are independently selected from the group consisting of:
(i) hydrogen,
(ii) C$_1$-C$_6$ alkyl, and
(iii) C$_3$-C$_6$ cycloalkyl;
X is selected from the group consisting of —CR$^{11a}$= and —N=;
X$^1$ is selected from the group consisting of —CR$^{11b}$= and —N=;
X$^2$ is selected from the group consisting of —CR$^{11c}$= and —N=;
X$^3$ is selected from the group consisting of —CR$^{11d}$= and —N=; and
each R$^{11a}$, R$^{11b}$, R$^{11c}$, and R$^{11d}$ is independently selected from the group consisting of hydrogen, halogen, hydroxy, cyano, C$_1$-C$_6$ alkyl, C$_1$-C$_6$ haloalkyl, and —NZ$^3$Z$^4$.

2. The compound of claim 1 of Formula II:

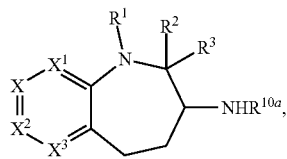

or a stereoisomer, tautomer, pharmaceutically acceptable salt, or solvate thereof.

3. The compound of claim 1, or a stereoisomer, tautomer, pharmaceutically acceptable salt, or solvate thereof, wherein $R^{10a}$ is selected from the group consisting of —C(=O)$Z^2$ and unsubstituted or substituted $C_1$-$C_6$ alkyl; and $Z^2$ is selected from the group consisting of:
(i) $C_1$-$C_6$ alkyl; and
(ii) unsubstituted or substituted $C_2$-$C_6$ alkenyl, wherein one or more substituents are independently selected from the group consisting of cyano, —S(=O)$_2Z^2$, —S(=O)$_2$N$Z^3Z^4$, halogen, —N$Z^3Z^4$, 4- to 8-membered heterocycle.

4. The compound of claim 1, or a stereoisomer, tautomer, pharmaceutically acceptable salt, or solvate thereof, wherein $R^2$ and $R^3$ taken together with the carbon atom to which they are attached form a —C(=O)— group.

5. The compound of claim 1, or a stereoisomer, tautomer, pharmaceutically acceptable salt, or solvate thereof, wherein $R^2$ and $R^3$ are hydrogen.

6. The compound of claim 1, or a stereoisomer, tautomer, pharmaceutically acceptable salt, or solvate thereof, wherein:
X is —$CR^{11a}$=;
$X^1$ is —$CR^{11b}$=;
$X^2$ is —$CR^{11c}$=; and
$X^3$ is —$CR^{11d}$=.

7. The compound of claim 1 of Formula III:

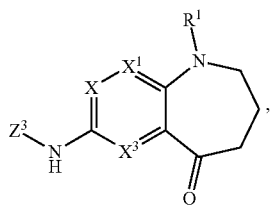

or a stereoisomer, tautomer, pharmaceutically acceptable salt, or solvate thereof.

8. The compound of claim 1, or a stereoisomer, tautomer, pharmaceutically acceptable salt, or solvate thereof, wherein $Z^3$ is unsubstituted or substituted $C_1$-$C_6$ alkyl.

9. The compound of claim 8, or a stereoisomer, tautomer, pharmaceutically acceptable salt, or solvate thereof, wherein:
X is —$CR^{11a}$=;
$X^1$ is —$CR^{11b}$=; and
$X^3$ is —$CR^{11d}$=.

10. The compound of claim 1, or a stereoisomer, tautomer, pharmaceutically acceptable salt, or solvate thereof, wherein R1 is substituted C6-C10 aryl, wherein one or more substituents are independently selected from the group consisting of halogen, hydroxy, cyano, C1-C6 alkyl, and —OZ1.

11. A compound, or a stereoisomer, tautomer, pharmaceutically acceptable salt, or solvate thereof, selected from the group consisting of:
N-(2-oxo-1-(4-(trifluoromethyl)phenyl)-2,3,4,5-tetrahydro-1H-benzo[b]azepin-3-yl)acrylamide;
3-amino-1-(4-(trifluoromethyl)phenyl)-1,3,4,5-tetrahydro-2H-benzo[b]azepin-2-one;
3-((3-hydroxypropyl)amino)-1-(4-(trifluoromethyl)phenyl)-1,3,4,5-tetrahydro-2H-benzo[b]azepin-2-one;
2-((1-(4-(trifluoromethyl)phenyl)-2,3,4,5-tetrahydro-1H-benzo[b]azepin-3-yl)amino)ethan-1-ol;
7-((2-hydroxyethyl)amino)-1-(4-(trifluoromethyl)phenyl)-1,2,3,4-tetrahydro-5H-benzo[b]azepin-5-one;
7-((3-hydroxypropyl)amino)-1-(4-(trifluoromethyl)phenyl)-1,2,3,4-tetrahydro-5H-benzo[b]azepin-5-one;
N-(1-(4-(trifluoromethyl)phenyl)-2,3,4,5-tetrahydro-1H-benzo[b]azepin-3-yl)acrylamide
3-((2-hydroxyethyl)amino)-1-(4-(trifluoromethyl)phenyl)-1,3,4,5-tetrahydro-2H-benzo[b]azepin-2-one;
3-((1-(4-(trifluoromethyl)phenyl)-2,3,4,5-tetrahydro-1H-benzo[b]azepin-3-yl)amino)propan-1-ol;
3-((1-(4-(trifluoromethyl)phenyl)-2,3,4,5-tetrahydro-1H-benzo[b]azepin-3-yl)amino)propanoic acid;
1-(4-(trifluoromethyl)phenyl)-2,3,4,5-tetrahydro-1H-benzo[b]azepin-3-amine;
N-(1-(4-(trifluoromethyl)phenyl)-2,3,4,5-tetrahydro-1H-benzo[b]azepin-3-yl)propionamide;
N-(2-oxo-1-(4-(trifluoromethyl)phenyl)-1,2,3,4-tetrahydroquinolin-3-yl)acrylamide;
N-(5-fluoro-2-oxo-1-(4-(trifluoromethyl)phenyl)-1,2,3,4-tetrahydroquinolin-3-yl)acrylamide; and
N-(2-oxo-1-(4-(trifluoromethyl)phenyl)-1,2,3,4-tetrahydro-1,6-naphthyridin-3-yl)acrylamide.

12. A pharmaceutical composition comprising the compound of claim 1, and a pharmaceutically acceptable carrier.

13. A method for the prevention or treatment of a YAP/TAZ-TEAD activation mediated disorders in an animal, mammal or human comprising administering to said animal, mammal or human in need for such prevention or treatment an effective dose of a compound of claim 1.

14. The method of claim 13, further comprising administering one or more other medicines selected from the group consisting of EGFR inhibitors, MEK inhibitors, AXL inhibitors, B-RAF inhibitors, and RAS inhibitors.

15. A pharmaceutical composition comprising a compound of claim 11, and a pharmaceutically acceptable carrier.

16. A method for the prevention or treatment of a YAP/TAZ-TEAD activation mediated disorders in an animal, mammal or human comprising administering to said animal, mammal or human in need for such prevention or treatment an effective dose of a compound of claim 11.

17. The method of claim 16, further comprising administering one or more other medicines selected from the group consisting of EGFR inhibitors, MEK inhibitors, AXL inhibitors, B-RAF inhibitors, and RAS inhibitors.

18. A compound of Formula I:

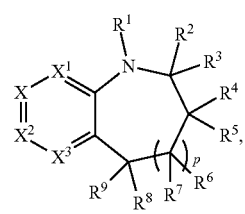

or a stereoisomer, tautomer, pharmaceutically acceptable salt, or solvate thereof, wherein:

p is 1 or 2;

$R^1$ is selected from the group consisting of:
  (i) hydrogen,
  (ii) unsubstituted or substituted $C_1$-$C_6$ alkyl, wherein one or more substituents are independently selected from the group consisting of:
    (a) unsubstituted or substituted $C_6$-$C_{10}$ aryl, wherein one or more substituents are independently selected from the group consisting of:
      (1) halogen,
      (2) cyano,
      (3) $C_1$-$C_6$ alkyl,
      (4) $C_3$-$C_6$ cycloalkyl,
      (5) $C_1$-$C_6$ haloalkyl,
      (6) —$OZ^1$,
      (7) $C_2$-$C_6$ alkenyl, and
      (8) $C_2$-$C_6$ alkynyl,
    (b) unsubstituted or substituted $C_3$-$C_6$ cycloalkyl, wherein one or more substituents are independently selected from the group consisting of:
      (1) halogen,
      (2) cyano,
      (3) $C_1$-$C_6$ alkyl,
      (4) $C_3$-$C_6$ cycloalkyl,
      (5) $C_1$-$C_6$ haloalkyl, and
      (6) —$OZ^1$,
    (c) $C_2$-$C_6$ alkynyl,
  (iii) unsubstituted or substituted $C_6$-$C_{10}$ aryl, wherein one or more substituents are independently selected from the group consisting of:
    (a) halogen,
    (b) cyano,
    (c) $C_1$-$C_6$ alkyl,
    (d) $C_3$-$C_6$ cycloalkyl,
    (e) $C_1$-$C_6$ haloalkyl,
    (f) —$OZ^1$, and
    (g) unsubstituted or substituted $C_6$-$C_{10}$ aryl, wherein one or more substituents are independently selected from the group consisting of halogen, $C_1$-$C_6$ alkyl, and $C_1$-$C_6$ haloalkyl, and —$OZ^1$,
  (iv) unsubstituted or substituted 5- to 9-membered heteroaryl, wherein one or more substituents are independently selected from the group consisting of:
    (a) halogen,
    (b) cyano,
    (c) $C_1$-$C_6$ alkyl,
    (d) $C_3$-$C_6$ cycloalkyl,
    (e) $C_1$-$C_6$ haloalkyl,
    (f) —$OZ^1$, and
    (g) unsubstituted or substituted $C_6$-$C_{10}$ aryl, wherein one or more substituents are independently selected from the group consisting of halogen, $C_1$-$C_6$ alkyl, and $C_1$-$C_6$ haloalkyl, and —$OZ^1$,
  (v) unsubstituted or substituted $C_3$-$C_6$ cycloalkyl, wherein one or more substituents are independently selected from the group consisting of:
    (a) halogen,
    (b) cyano,
    (c) $C_1$-$C_6$ alkyl,
    (d) $C_3$-$C_6$ cycloalkyl,
    (e) $C_1$-$C_6$ haloalkyl, and
    (f) —$OZ^1$,
  (vi) unsubstituted or substituted $C_3$-$C_6$ heterocycle, wherein one or more substituents are independently selected from the group consisting of:
    (a) halogen,
    (b) cyano,
    (c) $C_1$-$C_6$ alkyl,
    (d) $C_3$-$C_6$ cycloalkyl,
    (e) $C_1$-$C_6$ haloalkyl, and
    (f) —$OZ^1$,
  (vii) —$S(=O)_2Z^2$, and
  (viii) —$C(=O)Z^2$;

$R^2$ and $R^3$ are independently selected from the group consisting of hydrogen and $C_1$-$C_6$ alkyl; or $R^2$ and $R^3$ taken together with the carbon atom to which they are attached form a —$C(=O)$— group;

$R^4$ is selected from the group consisting of hydrogen and —$NR^{10a}R^{10b}$;

$R^5$ is selected from the group consisting of hydrogen and $C_1$-$C_6$ alkyl;

each $R^6$ and $R^7$ is independently selected from the group consisting of hydrogen and $C_1$-$C_6$ alkyl;

$R^8$ and $R^9$ are independently selected from the group consisting of hydrogen and $C_1$-$C_6$ alkyl;

$R^{10a}$ is selected from the group consisting of:
  (i) —$C(=O)Z^2$
  (ii) —$C(=O)OZ^2$,
  (iii) —$C(=O)NZ^3Z^4$,
  (iv) —$S(=O)_2Z^2$,
  (v) —$S(=O)_2NZ^3Z^4$,
  (vi) —$S(=O)(=NZ)Z^2$,
  (vii) —$S(=NZ^5)(=NZ^6)Z^2$,
  (viii) —$S(=O)(=NZ^5)NZ^3Z^4$, and
  (ix) unsubstituted or substituted $C_1$-$C_6$ alkyl, wherein one or more substituents are independently selected from the group consisting of:
    (a) cyano,
    (b) hydroxy,
    (c) —$OZ^1$,
    (d) —$C(=O)OH$,
    (e) —$C(=O)Z^2$
    (f) —$C(=O)OZ^2$,
    (g) —$C(=O)NZ^3Z^4$,
    (h) —$S(=O)_2Z^2$,
    (i) —$S(=O)_2NZ^3Z^4$,
    (j) —$S(=O)(=NZ^5)Z^2$,
    (k) —$S(=NZ^5)(=NZ^6)Z^2$,
    (l) —$S(=O)(=NZ^5)NZ^3Z^4$, and
    (m) —$NZ^3Z^4$, $R^{10b}$ is selected from the group consisting of hydrogen and $C_1$-$C_6$ alkyl;

each $Z^1$ is independently selected from the group consisting of:
  (i) hydrogen,
  (ii) $C_1$-$C_6$ alkyl,
  (iii) unsubstituted or substituted $C_2$-$C_6$ alkenyl, wherein one or more substituents are independently selected from the group consisting of cyano, —$S(=O)_2Z^2$, —$S(=O)_2NZ^3Z^4$, halogen, —$NZ^3Z^4$, and 4- to 8-membered heterocycle,
  (iv) $C_2$-$C_6$ alkynyl,
  (v) $C_3$-$C_6$ cycloalkyl,
  (vi) $C_3$-$C_6$ cycloalkenyl, and
  (vii) $C_1$-$C_6$ haloalkyl;

each $Z^2$ is independently selected from the group consisting of:
  (i) unsubstituted or substituted $C_1$-$C_6$ alkyl, wherein one or more substituents are independently selected from the group consisting of cyano and $C_2$-$C_6$ alkynyl;

(ii) unsubstituted or substituted $C_2$-$C_6$ alkenyl, wherein one or more substituents are independently selected from the group consisting of cyano, —S(=O)$_2$Z$^2$, —S(=O)$_2$NZ$^3$Z$^4$, halogen, —NZ$^3$Z$^4$, 4- to 8-membered heterocycle,
(iii) $C_2$-$C_6$ alkynyl,
(iv) $C_3$-$C_6$ cycloalkyl,
(v) $C_3$-$C_6$ cycloalkenyl,
(vi) $C_1$-$C_6$ haloalkyl,
(vii) unsubstituted or substituted $C_6$-$C_{10}$ aryl, wherein one or more substituents are independently selected from the group consisting of halogen, $C_1$-$C_6$ alkyl, and $C_1$-$C_6$ haloalkyl, and —OZ$^1$, and
(viii) unsubstituted or substituted $C_3$-$C_6$ cycloalkyl, wherein one or more substituents are independently selected from the group consisting of halogen, $C_1$-$C_6$ alkyl, and $C_1$-$C_6$ haloalkyl, and —OZ$^1$;

each Z$^3$ and Z$^4$ are independently selected from the group consisting of:
(i) hydrogen;
(ii) unsubstituted or substituted $C_1$-$C_6$ alkyl, wherein one or more substituents are independently selected from the group consisting of:
  (a) unsubstituted or substituted $C_6$-$C_{10}$ aryl, wherein one or more substituents are independently selected from the group consisting of:
    (1) halogen,
    (2) cyano,
    (3) $C_1$-$C_6$ alkyl,
    (4) $C_3$-$C_6$ cycloalkyl,
    (5) $C_1$-$C_6$ haloalkyl,
    (6) —OZ$^1$,
    (7) $C_2$-$C_6$ alkenyl, and
    (8) $C_2$-$C_6$ alkynyl,
  (b) unsubstituted or substituted $C_3$-$C_6$ cycloalkyl, wherein one or more substituents are independently selected from the group consisting of:
    (1) halogen,
    (2) cyano,
    (3) $C_1$-$C_6$ alkyl,
    (4) $C_3$-$C_6$ cycloalkyl,
    (5) $C_1$-$C_6$ haloalkyl, and
    (6) —OZ$^1$,
  (c) unsubstituted or substituted 5- to 9-membered heteroaryl, wherein one or more substituents are independently selected from the group consisting of:
    (1) halogen,
    (2) cyano,
    (3) $C_1$-$C_6$ alkyl,
    (4) $C_3$-$C_6$ cycloalkyl,
    (5) $C_1$-$C_6$ haloalkyl,
    (6) —OZ$^1$,
    (7) $C_2$-$C_6$ alkenyl, and
    (8) $C_2$-$C_6$ alkynyl,
  (d) cyano,
  (e) hydroxy,
  (f) —OZ$^1$, and
  (g) —NZ$^3$Z$^4$,
(iii) unsubstituted or substituted $C_2$-$C_6$ alkenyl, wherein one or more substituents are independently selected from the group consisting of cyano, —S(=O)$_2$Z$^2$, —S(=O)$_2$NZ$^3$Z$^4$, halogen, —NZ$^3$Z$^4$, 4- to 8-membered heterocycle,
(iv) $C_2$-$C_6$ alkynyl,
(v) $C_3$-$C_6$ cycloalkyl,
(vi) $C_3$-$C_6$ cycloalkenyl, and
(vii) $C_1$-$C_6$ haloalkyl;

each Z$^5$ and Z$^6$ are independently selected from the group consisting of:
(i) hydrogen,
(ii) $C_1$-$C_6$ alkyl, and
(iii) $C_3$-$C_6$ cycloalkyl;

X is selected from the group consisting of —CR$^{11a}$= and —N=;
X$^1$ is selected from the group consisting of —CR$^{11b}$= and —N=;
X$^2$ is selected from the group consisting of —CR$^{11d}$= and —N=;
X$^3$ is selected from the group consisting of —CR$^{11d}$= and —N=; and
each R$^{11a}$, R$^{11b}$, R$^{11c}$, and R$^{11d}$ is independently selected from the group consisting of hydrogen, halogen, hydroxy, cyano, $C_1$-$C_6$ alkyl, $C_1$-$C_6$ haloalkyl, and —NZ$^3$Z$^4$.

19. A compound of claim 11, or a pharmaceutically acceptable salt thereof, selected from the group consisting of:
(S)-2-((1-(4-(trifluoromethyl)phenyl)-2,3,4,5-tetrahydro-1H-benzo [b]azepin-3-yl)amino)ethan-1-ol;
(R)-2-((1-(4-(trifluoromethyl)phenyl)-2,3,4,5-tetrahydro-1H-benzo [b]azepin-3-yl)amino)ethan-1-ol;
(S)-N-(1-(4-(trifluoromethyl)phenyl)-2,3,4,5-tetrahydro-1H-benzo [b]azepin-3-yl)acrylamide; and
(R)-N-(1-(4-(trifluoromethyl)phenyl)-2,3,4,5-tetrahydro-1H-benzo [b]azepin-3-yl)acrylamide.

* * * * *